(12) United States Patent
Massimini et al.

(10) Patent No.: US 12,280,223 B2
(45) Date of Patent: Apr. 22, 2025

(54) FOCUSING ELEMENT FOR PLASMA SYSTEM TO DISRUPT VASCULAR LESIONS

(71) Applicant: Boston Scientific Scimed, Inc., Maple Grove, MN (US)

(72) Inventors: Daniel Frank Massimini, Brooklyn Park, MN (US); Daniel Lee Krautkremer, Plymouth, MN (US); Haiping Shao, Plymouth, MN (US); Roger W. McGowan, Otsego, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1267 days.

(21) Appl. No.: 16/904,289

(22) Filed: Jun. 17, 2020

(65) Prior Publication Data

US 2020/0406009 A1 Dec. 31, 2020

Related U.S. Application Data

(60) Provisional application No. 62/867,009, filed on Jun. 26, 2019, provisional application No. 62/867,026, (Continued)

(51) Int. Cl.
*A61M 25/01* (2006.01)
*A61B 17/22* (2006.01)
(Continued)

(52) U.S. Cl.
CPC ......... *A61M 25/0133* (2013.01); *A61B 17/22* (2013.01); *A61B 18/245* (2013.01);
(Continued)

(58) Field of Classification Search
CPC ............ A61B 18/245; A61B 17/22004; A61B 2018/0022; A61B 17/22; A61B 18/26;
(Continued)

(56) References Cited

U.S. PATENT DOCUMENTS 4,649,924 A 3/1987 Taccardi
4,699,147 A 10/1987 Chilson et al.
(Continued)

FOREIGN PATENT DOCUMENTS

AU 2017205323 1/2022
AU 2019452180 1/2022
(Continued)

OTHER PUBLICATIONS

Provisional International Search Report and Written Opinion dated Feb. 19, 2021 in PCT Application Serial No. PCT/US2020/059960.
(Continued)

*Primary Examiner* — Shaun L David
*Assistant Examiner* — Mitchell Brian Hoag
(74) *Attorney, Agent, or Firm* — ROEDER & BRODER LLP; James P. Broder

(57) ABSTRACT

A catheter system for pressure wave and inertial impulse generation for intravascular lesion disruption at a treatment site includes a catheter including an elongate shaft and balloon coupled to the elongate shaft. The catheter system includes a light guide disposed along the elongate shaft and at least partially within the balloon, where the light guide is in optical communication with a light source and a balloon fluid. The catheter can include a first focusing element located at a distal portion of the light guide and in optical communication with the light source. The first focusing element can direct light from within the light guide to a first location at a first distance away from the distal portion of the light guide to initiate plasma formation in the balloon fluid away from the distal portion and to cause rapid bubble formation, thereby imparting pressure waves at the treatment site.

20 Claims, 21 Drawing Sheets

Related U.S. Application Data filed on Jun. 26, 2019, provisional application No. 62/867,034, filed on Jun. 26, 2019, provisional application No. 62/866,981, filed on Jun. 26, 2019.

(51) Int. Cl.

| | | |
|---|---|---|
| *A61B 18/24* | (2006.01) | |
| *A61B 18/26* | (2006.01) | |
| *A61L 27/20* | (2006.01) | |
| *A61M 25/00* | (2006.01) | |
| *A61M 25/09* | (2006.01) | |
| *A61B 18/00* | (2006.01) | |
| *A61B 18/22* | (2006.01) | |
| *A61B 90/30* | (2016.01) | |

(52) U.S. Cl.
CPC .............. *A61B 18/26* (2013.01); *A61L 27/20* (2013.01); *A61M 25/0009* (2013.01); *A61M 25/0155* (2013.01); *A61M 25/09* (2013.01); *A61B 2017/22062* (2013.01); *A61B 2018/0022* (2013.01); *A61B 2018/00285* (2013.01); *A61B 2018/2261* (2013.01); *A61B 2018/2266* (2013.01); *A61B 2018/2277* (2013.01); *A61B 2018/2294* (2013.01); *A61B 2018/263* (2013.01); *A61B 2090/306* (2016.02); *A61L 2400/12* (2013.01); *A61M 2025/09008* (2013.01); *A61M 2025/09183* (2013.01); *A61M 2202/0415* (2013.01); *A61M 2205/3592* (2013.01); *A61M 2205/587* (2013.01)

(58) Field of Classification Search
CPC .. A61B 2017/22062; A61B 2018/2261; A61B 2018/2266; A61B 2018/2277; A61B 2018/266; A61B 2018/263; A61B 2017/2205; A61B 2017/22007; A61B 2017/22008; A61B 2017/22009; A61B 2017/22024; A61B 2017/22025; A61B 2018/00285; A61B 2018/2294
See application file for complete search history.

(56) References Cited

U.S. PATENT DOCUMENTS

| | | | |
|---|---|---|---|
| 4,799,479 A | 1/1989 | Spears | |
| 4,850,351 A | 7/1989 | Herman | |
| 4,913,142 A | 4/1990 | Kittrell et al. | |
| 4,932,954 A | 6/1990 | Wondrazek et al. | |
| 4,955,895 A | 9/1990 | Sugiyama | |
| 4,960,108 A | 10/1990 | Reichel et al. | |
| 4,994,059 A | 2/1991 | Kosa et al. | |
| 4,998,930 A * | 3/1991 | Lundahl | A61N 5/0603 606/15 |
| 5,034,010 A | 7/1991 | Kittrell et al. | |
| 5,041,121 A | 8/1991 | Wondrazek et al. | |
| 5,082,343 A | 1/1992 | Coult et al. | |
| 5,093,877 A | 3/1992 | Aita et al. | |
| 5,104,391 A | 4/1992 | Ingle | |
| 5,104,392 A | 4/1992 | Kittrell et al. | |
| 5,109,452 A | 4/1992 | Selvin et al. | |
| 5,116,227 A | 5/1992 | Levy | |
| 5,126,165 A | 6/1992 | Akihama et al. | |
| 5,152,768 A | 10/1992 | Bhatta | |
| 5,173,049 A | 12/1992 | Levy | |
| 5,176,674 A * | 1/1993 | Hofmann | A61B 18/245 606/7 |
| 5,181,921 A | 1/1993 | Makita et al. | |
| 5,200,838 A | 4/1993 | Nudelman | |
| 5,269,777 A * | 12/1993 | Doiron | A61N 5/062 606/7 |
| 5,290,277 A | 3/1994 | Vercimak et al. | |
| 5,324,282 A | 6/1994 | Dodick | |
| 5,328,472 A | 7/1994 | Steinke et al. | |
| 5,336,184 A | 8/1994 | Teirstein | |
| 5,363,458 A * | 11/1994 | Pan | A61B 18/22 385/128 |
| 5,372,138 A | 12/1994 | Crowley | |
| 5,387,225 A | 2/1995 | Euteneur | |
| 5,400,428 A | 3/1995 | Grace | |
| 5,410,797 A | 5/1995 | Steinke et al. | |
| 5,422,926 A | 6/1995 | Smith | |
| 5,431,647 A * | 7/1995 | Purcell, Jr. | A61B 18/24 606/17 |
| 5,454,809 A | 10/1995 | Janssen | |
| 5,456,680 A | 10/1995 | Taylor | |
| 5,474,537 A | 12/1995 | Solar | |
| 5,509,917 A | 4/1996 | Cecchetti | |
| 5,540,679 A | 7/1996 | Fram | |
| 5,562,657 A | 10/1996 | Griffin | |
| 5,598,494 A | 1/1997 | Behrmann et al. | |
| 5,609,606 A | 3/1997 | O'Boyle | |
| 5,611,807 A | 3/1997 | O'Boyle | |
| 5,637,877 A * | 6/1997 | Sinofsky | A61N 5/0601 606/15 |
| 5,661,829 A | 8/1997 | Zheng | |
| 5,697,377 A | 12/1997 | Wittkampf | |
| 5,718,241 A | 2/1998 | Ben-Haim et al. | |
| 5,729,583 A | 3/1998 | Tang | |
| 5,764,843 A | 6/1998 | Macken et al. | |
| 5,772,609 A | 6/1998 | Nguyen et al. | |
| 5,860,974 A | 1/1999 | Abele | |
| 5,891,135 A | 4/1999 | Jackson et al. | |
| 5,906,611 A | 5/1999 | Dodick et al. | |
| 5,944,687 A | 8/1999 | Benett et al. | |
| 6,015,404 A | 1/2000 | Altshuler | |
| 6,080,119 A | 6/2000 | Schwarze et al. | |
| 6,123,923 A | 9/2000 | Unger | |
| 6,139,510 A | 10/2000 | Palermo | |
| 6,186,963 B1 | 2/2001 | Schwarze et al. | |
| 6,203,537 B1 | 3/2001 | Adrian | |
| 6,210,404 B1 | 4/2001 | Shadduck | |
| 6,339,470 B1 | 1/2002 | Papademetriou et al. | |
| 6,356,575 B1 | 3/2002 | Fukumoto | |
| 6,368,318 B1 | 4/2002 | Visuri et al. | |
| 6,423,055 B1 * | 7/2002 | Farr | A61B 18/245 606/7 |
| 6,500,174 B1 | 12/2002 | Maguire et al. | |
| 6,514,203 B2 | 2/2003 | Bukshpan | |
| 6,514,249 B1 | 2/2003 | Maguire | |
| 6,524,251 B2 | 3/2003 | Rabiner et al. | |
| 6,538,739 B1 | 3/2003 | Visuri et al. | |
| 6,548,010 B1 | 4/2003 | Stivland et al. | |
| 6,560,387 B1 | 5/2003 | Hehlen et al. | |
| 6,607,502 B1 | 8/2003 | Maguire et al. | |
| 6,631,220 B1 | 10/2003 | Liang et al. | |
| 6,652,547 B2 | 11/2003 | Rabiner et al. | |
| 6,666,834 B2 | 12/2003 | Restle et al. | |
| 6,702,781 B1 | 3/2004 | Reifart et al. | |
| 6,773,447 B2 | 8/2004 | Laguna | |
| 6,824,554 B1 | 11/2004 | Jang | |
| 6,849,994 B1 | 2/2005 | White et al. | |
| 6,890,317 B2 | 5/2005 | Gerdts et al. | |
| 6,947,785 B1 | 9/2005 | Beatty et al. | |
| 6,966,890 B2 | 11/2005 | Coyle et al. | |
| 6,978,168 B2 | 12/2005 | Beatty et al. | |
| 6,990,370 B1 | 1/2006 | Beatty et al. | |
| 7,273,470 B2 | 9/2007 | Wantink | |
| 7,309,324 B2 | 12/2007 | Hayes et al. | |
| 7,367,967 B2 | 5/2008 | Eidenschink | |
| 7,470,240 B2 | 12/2008 | Schultheiss et al. | |
| 7,539,231 B1 | 5/2009 | Honea et al. | |
| 7,569,032 B2 | 8/2009 | Naimark et al. | |
| 7,599,588 B2 | 10/2009 | Eberle et al. | |
| 7,641,646 B2 | 1/2010 | Kennedy, II | |
| 7,713,260 B2 | 5/2010 | Lessard | |
| 7,758,572 B2 | 7/2010 | Weber et al. | |
| 7,762,984 B2 | 7/2010 | Kumoyama et al. | |
| 7,810,395 B2 | 10/2010 | Zhou | |
| 7,850,685 B2 | 12/2010 | Kunis et al. | |
| 7,867,178 B2 | 1/2011 | Simnacher | |
| 7,909,797 B2 | 3/2011 | Kennedy, II et al. | |

(56) References Cited

U.S. PATENT DOCUMENTS

| | | |
|---|---|---|
| 7,967,781 B2 | 6/2011 | Simpson et al. |
| 7,972,299 B2 | 7/2011 | Carter |
| 7,985,189 B1 | 7/2011 | Ogden et al. |
| 8,021,328 B2 | 9/2011 | Lee |
| 8,029,473 B2 | 10/2011 | Carter |
| 8,043,256 B2 | 10/2011 | Hansen |
| 8,088,121 B2 | 1/2012 | Nishide |
| 8,162,859 B2 | 4/2012 | Schultheiss et al. |
| 8,166,825 B2 | 5/2012 | Zhou |
| 8,192,368 B2 | 6/2012 | Woodruff |
| 8,267,886 B2 | 9/2012 | Ewing |
| 8,292,913 B2 | 10/2012 | Warnack |
| 8,328,820 B2 | 12/2012 | Diamant |
| 8,364,235 B2 | 1/2013 | Kordis et al. |
| 8,382,738 B2 | 2/2013 | Simpson et al. |
| 8,414,527 B2 | 4/2013 | Mallaby |
| 8,419,613 B2 | 4/2013 | Saadat |
| 8,439,890 B2 | 5/2013 | Beyar |
| 8,556,813 B2 | 10/2013 | Cashman et al. |
| 8,574,247 B2 | 11/2013 | Adams et al. |
| 8,657,814 B2 | 2/2014 | Werneth |
| 8,709,075 B2 | 4/2014 | Adams et al. |
| 8,728,091 B2 | 5/2014 | Hakala et al. |
| 8,734,424 B2 | 5/2014 | Watanabe |
| 8,747,416 B2 | 6/2014 | Hakala et al. |
| 8,784,362 B2 | 7/2014 | Boutilette |
| 8,834,510 B2 | 9/2014 | Wilson et al. |
| 8,888,788 B2 | 11/2014 | Hakala et al. |
| 8,956,371 B2 | 2/2015 | Hawkins et al. |
| 8,956,374 B2 | 2/2015 | Hawkins et al. |
| 8,986,339 B2 | 3/2015 | Warnack |
| 8,992,817 B2 | 3/2015 | Stamberg |
| 9,005,216 B2 | 4/2015 | Hakala et al. |
| 9,011,462 B2 | 4/2015 | Adams et al. |
| 9,011,463 B2 | 4/2015 | Adams et al. |
| 9,011,511 B2 | 4/2015 | Gregorich |
| 9,044,618 B2 | 6/2015 | Hawkins et al. |
| 9,044,619 B2 | 6/2015 | Hawkins et al. |
| 9,072,534 B2 | 7/2015 | Adams et al. |
| 9,089,669 B2 | 7/2015 | Haslinger et al. |
| 9,131,949 B2 | 9/2015 | Coleman et al. |
| 9,138,249 B2 | 9/2015 | Adams et al. |
| 9,138,260 B2 | 9/2015 | Miller et al. |
| 9,180,280 B2 | 11/2015 | Hawkins et al. |
| 9,220,521 B2 | 12/2015 | Hawkins et al. |
| 9,237,984 B2 | 1/2016 | Hawkins et al. |
| 9,289,132 B2 | 3/2016 | Ghaffari et al. |
| 9,289,224 B2 | 3/2016 | Adams et al. |
| 9,320,530 B2 | 4/2016 | Grace |
| 9,333,000 B2 | 5/2016 | Hakala et al. |
| 9,339,632 B2 | 5/2016 | Eidenschink et al. |
| 9,364,645 B2 | 6/2016 | Erikawa |
| 9,375,223 B2 | 6/2016 | Wallace |
| 9,421,025 B2 | 8/2016 | Hawkins et al. |
| 9,433,428 B2 | 9/2016 | Hakala et al. |
| 9,433,745 B2 | 9/2016 | Cully |
| 9,504,809 B2 | 11/2016 | Bo |
| 9,510,887 B2 | 12/2016 | Burnett |
| 9,522,012 B2 | 12/2016 | Adams |
| 9,554,815 B2 | 1/2017 | Adams et al. |
| 9,555,267 B2 | 1/2017 | Ein-Gal |
| 9,566,209 B2 | 2/2017 | Katragadda et al. |
| 9,579,114 B2 | 2/2017 | Mantell et al. |
| 9,585,684 B2 | 3/2017 | Nita et al. |
| 9,592,328 B2 | 3/2017 | Jeevanandam |
| 9,629,567 B2 | 4/2017 | Porath et al. |
| 9,642,673 B2 | 5/2017 | Adams |
| 9,662,069 B2 | 5/2017 | De Graff et al. |
| 9,687,166 B2 | 6/2017 | Subramaniam |
| 9,730,715 B2 | 8/2017 | Adams |
| 9,737,361 B2 | 8/2017 | Magana |
| 9,764,142 B2 | 9/2017 | Imran |
| 9,782,570 B2 | 10/2017 | Hirszowicz |
| 9,814,476 B2 | 11/2017 | Adams et al. |
| 9,833,348 B2 | 12/2017 | Jordan et al. |
| 9,839,764 B2 | 12/2017 | Chouinard |
| 9,861,377 B2 | 1/2018 | Mantell et al. |
| 9,867,629 B2 | 1/2018 | Hawkins et al. |
| 9,878,135 B2 | 1/2018 | Holzapfel et al. |
| 9,894,756 B2 | 2/2018 | Weinkam et al. |
| 9,901,704 B2 | 2/2018 | Appling |
| 9,955,946 B2 | 5/2018 | Miller et al. |
| 9,974,963 B2 | 5/2018 | Imran |
| 9,974,970 B2 | 5/2018 | Nuta et al. |
| 9,993,292 B2 | 6/2018 | Adams et al. |
| 10,039,561 B2 | 8/2018 | Adams et al. |
| 10,086,175 B2 | 10/2018 | Torres et al. |
| 10,124,153 B2 | 11/2018 | Feig |
| 10,136,829 B2 | 11/2018 | Deno et al. |
| 10,149,690 B2 | 12/2018 | Hawkins et al. |
| 10,159,505 B2 | 12/2018 | Hakala et al. |
| 10,194,994 B2 | 2/2019 | Deno et al. |
| 10,201,387 B2 | 2/2019 | Grace et al. |
| 10,206,698 B2 | 2/2019 | Hakala et al. |
| 10,226,265 B2 | 3/2019 | Ku et al. |
| 10,245,410 B2 | 4/2019 | Aggerholm |
| 10,357,264 B2 | 7/2019 | Kat-Kuoy |
| 10,405,923 B2 | 9/2019 | Yu et al. |
| 10,406,031 B2 | 9/2019 | Thyzel |
| 10,406,318 B2 | 9/2019 | Williams |
| 10,420,569 B2 | 9/2019 | Adams |
| 10,439,791 B2 | 10/2019 | Kalhan |
| 10,441,300 B2 | 10/2019 | Hawkins |
| 10,449,339 B2 | 10/2019 | Wilson et al. |
| 10,463,430 B2 | 11/2019 | Dick |
| 10,478,202 B2 | 11/2019 | Adams et al. |
| 10,517,620 B2 | 12/2019 | Adams |
| 10,517,621 B1 | 12/2019 | Hakala et al. |
| 10,537,287 B2 | 1/2020 | Braido et al. |
| 10,555,744 B2 | 2/2020 | Nguyen et al. |
| 10,561,428 B2 | 2/2020 | Eggert et al. |
| 10,583,277 B2 | 3/2020 | Rundquist |
| 10,589,073 B2 | 3/2020 | Mallaby |
| 10,617,850 B2 | 4/2020 | Tal |
| 10,646,240 B2 | 5/2020 | Betelia et al. |
| 10,668,245 B2 | 6/2020 | Kanae |
| 10,682,178 B2 | 6/2020 | Adams et al. |
| 10,695,531 B2 | 6/2020 | Suzuki |
| 10,702,293 B2 | 7/2020 | Adams et al. |
| 10,709,462 B2 | 7/2020 | Nguyen et al. |
| 10,709,872 B2 | 7/2020 | Alvarez et al. |
| 10,758,255 B2 | 9/2020 | Adams |
| 10,797,684 B1 | 10/2020 | Benz et al. |
| 10,799,688 B2 | 10/2020 | Calhoun |
| 10,842,567 B2 | 11/2020 | Grace et al. |
| 10,850,075 B2 | 12/2020 | Tarunaga |
| 10,857,329 B2 | 12/2020 | Davies |
| 10,933,225 B2 | 3/2021 | Campbell |
| 10,959,743 B2 | 3/2021 | Adams et al. |
| 10,966,737 B2 | 4/2021 | Nguyen |
| 10,967,156 B2 | 4/2021 | Gulachenski |
| 10,973,538 B2 | 4/2021 | Hakala et al. |
| 10,980,987 B2 | 4/2021 | Tarunaga |
| 11,000,299 B2 | 5/2021 | Hawkins et al. |
| 11,020,135 B1 | 6/2021 | Hawkins |
| 11,026,707 B2 | 6/2021 | Ku et al. |
| 11,058,492 B2 | 7/2021 | Grace et al. |
| 11,076,874 B2 | 8/2021 | Hakala et al. |
| 11,116,939 B2 | 9/2021 | Jamous et al. |
| 11,141,131 B2 | 10/2021 | Stigall |
| 11,207,493 B2 | 12/2021 | Suzuki et al. |
| 11,213,661 B2 | 1/2022 | Spindler |
| 11,229,772 B2 | 1/2022 | Nita |
| 11,229,776 B2 | 1/2022 | Kugler et al. |
| 11,246,659 B2 | 2/2022 | Grace et al. |
| 11,253,681 B2 | 2/2022 | Williams |
| 11,484,327 B2 | 11/2022 | Anderson et al. |
| 11,633,200 B2 | 4/2023 | Anderson et al. |
| 11,779,363 B2 | 10/2023 | Vo |
| 11,826,530 B2 | 11/2023 | Suzuki |
| 11,911,054 B2 | 2/2024 | Singla |
| 11,911,056 B2 | 2/2024 | Anderson et al. |
| 11,918,285 B2 | 3/2024 | Sun et al. |
| 11,944,331 B2 | 4/2024 | Anderson et al. |

(56) References Cited

U.S. PATENT DOCUMENTS

| | | |
|---|---|---|
| 2001/0016761 A1 | 8/2001 | Rudie |
| 2001/0049464 A1* | 12/2001 | Ganz ..................... H01J 35/32 600/3 |
| 2001/0051784 A1 | 12/2001 | Brisken |
| 2002/0045811 A1 | 4/2002 | Kittrell et al. |
| 2002/0052621 A1* | 5/2002 | Fried ..................... A61B 18/24 606/192 |
| 2002/0065512 A1 | 5/2002 | Fjield et al. |
| 2002/0082553 A1 | 6/2002 | Duchamp |
| 2002/0183620 A1 | 12/2002 | Tearney |
| 2002/0183729 A1 | 12/2002 | Farr et al. |
| 2002/0188204 A1 | 12/2002 | McNamara et al. |
| 2003/0009157 A1 | 1/2003 | Levine et al. |
| 2003/0050632 A1 | 3/2003 | Fjield et al. |
| 2003/0065316 A1 | 4/2003 | Levine et al. |
| 2003/0114901 A1 | 6/2003 | Loeb et al. |
| 2003/0125719 A1 | 7/2003 | Furnish |
| 2003/0144654 A1 | 7/2003 | Hilal |
| 2003/0176873 A1 | 9/2003 | Chernenko et al. |
| 2004/0002677 A1 | 1/2004 | Gentsler |
| 2004/0024349 A1 | 2/2004 | Flock et al. |
| 2004/0073251 A1 | 4/2004 | Weber |
| 2004/0097996 A1 | 5/2004 | Rabiner |
| 2004/0133254 A1 | 7/2004 | Sterzer et al. |
| 2004/0162508 A1 | 8/2004 | Uebelacker |
| 2004/0210278 A1 | 10/2004 | Boll |
| 2004/0243119 A1 | 12/2004 | Lane et al. |
| 2004/0249401 A1 | 12/2004 | Rabiner |
| 2004/0254570 A1 | 12/2004 | Hadsjicostis |
| 2005/0010095 A1 | 1/2005 | Stewart et al. |
| 2005/0021013 A1 | 1/2005 | Visuri |
| 2005/0080396 A1 | 4/2005 | Rontal |
| 2005/0113722 A1 | 5/2005 | Schultheiss |
| 2005/0171437 A1 | 8/2005 | Carberry |
| 2005/0171527 A1 | 8/2005 | Bhola |
| 2005/0251131 A1 | 11/2005 | Lesh |
| 2005/0259319 A1 | 11/2005 | Brooker |
| 2005/0273014 A1 | 12/2005 | Gianchandani et al. |
| 2005/0277839 A1 | 12/2005 | Alderman et al. |
| 2006/0033241 A1 | 2/2006 | Schewe et al. |
| 2006/0084966 A1 | 4/2006 | Maguire et al. |
| 2006/0098921 A1 | 5/2006 | Benaron et al. |
| 2006/0190022 A1 | 8/2006 | Beyar et al. |
| 2006/0200039 A1 | 9/2006 | Brockway et al. |
| 2006/0221528 A1 | 10/2006 | Li et al. |
| 2006/0241524 A1 | 10/2006 | Lee et al. |
| 2006/0241572 A1 | 10/2006 | Zhou |
| 2006/0241733 A1 | 10/2006 | Zhang et al. |
| 2006/0270976 A1 | 11/2006 | Savage et al. |
| 2007/0027524 A1 | 2/2007 | Johnson |
| 2007/0043340 A1 | 2/2007 | Thyzel |
| 2007/0060990 A1 | 3/2007 | Satake |
| 2007/0088380 A1 | 4/2007 | Hirszowicz et al. |
| 2007/0118057 A1 | 5/2007 | Ein-gal |
| 2007/0142819 A1 | 6/2007 | El-Nounou et al. |
| 2007/0142821 A1 | 6/2007 | Hennessy et al. |
| 2007/0179496 A1 | 8/2007 | Swoyer |
| 2007/0239082 A1 | 10/2007 | Schultheiss et al. |
| 2007/0255270 A1 | 11/2007 | Carney |
| 2007/0264353 A1 | 11/2007 | Myntti et al. |
| 2007/0270897 A1 | 11/2007 | Skerven |
| 2007/0280311 A1 | 12/2007 | Hofmann |
| 2007/0299392 A1 | 12/2007 | Beyar et al. |
| 2008/0033519 A1 | 2/2008 | Burwell |
| 2008/0081950 A1 | 4/2008 | Koenig et al. |
| 2008/0086118 A1 | 4/2008 | Lai |
| 2008/0095714 A1 | 4/2008 | Castella et al. |
| 2008/0097251 A1 | 4/2008 | Babaev |
| 2008/0108867 A1 | 5/2008 | Zhou |
| 2008/0114341 A1 | 5/2008 | Thyzel |
| 2008/0132810 A1 | 6/2008 | Scoseria et al. |
| 2008/0175539 A1 | 7/2008 | Brown |
| 2008/0195088 A1* | 8/2008 | Farr ..................... A61B 18/245 606/15 |
| 2008/0214891 A1 | 9/2008 | Slenker et al. |
| 2008/0221550 A1 | 9/2008 | Lee |
| 2008/0281157 A1 | 11/2008 | Miyagi et al. |
| 2008/0296152 A1 | 12/2008 | Voss |
| 2008/0319356 A1 | 12/2008 | Cain et al. |
| 2009/0036803 A1 | 2/2009 | Warlick et al. |
| 2009/0043300 A1 | 2/2009 | Reitmajer et al. |
| 2009/0054881 A1 | 2/2009 | Krespi |
| 2009/0097806 A1 | 4/2009 | Viellerobe et al. |
| 2009/0125007 A1 | 5/2009 | Splinter |
| 2009/0131921 A1 | 5/2009 | Kurtz et al. |
| 2009/0192495 A1 | 7/2009 | Ostrovsky et al. |
| 2009/0240242 A1 | 9/2009 | Neuberger |
| 2009/0247945 A1 | 10/2009 | Levit |
| 2009/0281531 A1 | 11/2009 | Rizoiu |
| 2009/0292296 A1 | 11/2009 | Pansky |
| 2009/0296751 A1 | 12/2009 | Kewitsch et al. |
| 2009/0299327 A1 | 12/2009 | Tilson et al. |
| 2009/0306533 A1 | 12/2009 | Rousche |
| 2009/0312768 A1 | 12/2009 | Hawkins et al. |
| 2010/0016862 A1 | 1/2010 | Hawkins et al. |
| 2010/0036294 A1 | 2/2010 | Mantell et al. |
| 2010/0063491 A1 | 3/2010 | Verhagen |
| 2010/0094209 A1 | 4/2010 | Drasler et al. |
| 2010/0114020 A1 | 5/2010 | Hawkins et al. |
| 2010/0114065 A1 | 5/2010 | Hawkins et al. |
| 2010/0125268 A1 | 5/2010 | Gustus et al. |
| 2010/0160838 A1* | 6/2010 | Krespi ..................... A61B 18/26 604/20 |
| 2010/0160903 A1 | 6/2010 | Krespi |
| 2010/0168572 A1 | 7/2010 | Sliwa |
| 2010/0168836 A1 | 7/2010 | Kassab |
| 2010/0168862 A1 | 7/2010 | Edie et al. |
| 2010/0179632 A1 | 7/2010 | Bruszewski et al. |
| 2010/0191089 A1 | 7/2010 | Stebler et al. |
| 2010/0198114 A1 | 8/2010 | Novak et al. |
| 2010/0199773 A1 | 8/2010 | Zhou |
| 2010/0222786 A1 | 9/2010 | Kassab |
| 2010/0234875 A1 | 9/2010 | Allex et al. |
| 2010/0256535 A1 | 10/2010 | Novak et al. |
| 2010/0265733 A1 | 10/2010 | O'Leary |
| 2010/0316333 A1 | 12/2010 | Luther |
| 2011/0034832 A1 | 2/2011 | Cioanta et al. |
| 2011/0059415 A1 | 3/2011 | Kasenbacher |
| 2011/0082452 A1 | 4/2011 | Melsky |
| 2011/0082534 A1 | 4/2011 | Wallace |
| 2011/0118634 A1 | 5/2011 | Golan |
| 2011/0144502 A1 | 6/2011 | Zhou et al. |
| 2011/0184244 A1 | 7/2011 | Kagaya et al. |
| 2011/0208185 A1 | 8/2011 | Diamant et al. |
| 2011/0213349 A1 | 9/2011 | Brown |
| 2011/0245740 A1 | 10/2011 | Novak et al. |
| 2011/0257641 A1* | 10/2011 | Hastings ..................... A61B 18/24 606/15 |
| 2011/0263921 A1 | 10/2011 | Vrba et al. |
| 2011/0275990 A1 | 11/2011 | Besser et al. |
| 2011/0306956 A1 | 12/2011 | Islam |
| 2012/0064141 A1 | 3/2012 | Andreacchi et al. |
| 2012/0071715 A1 | 3/2012 | Beyar et al. |
| 2012/0071867 A1 | 3/2012 | Ryan |
| 2012/0071889 A1 | 3/2012 | Mantell et al. |
| 2012/0089132 A1 | 4/2012 | Dick et al. |
| 2012/0095335 A1 | 4/2012 | Sverdlik et al. |
| 2012/0095461 A1 | 4/2012 | Herscher et al. |
| 2012/0116289 A1 | 5/2012 | Hawkins et al. |
| 2012/0116486 A1 | 5/2012 | Naga et al. |
| 2012/0123331 A1 | 5/2012 | Satake |
| 2012/0123399 A1 | 5/2012 | Belikov |
| 2012/0143131 A1 | 6/2012 | Tun |
| 2012/0157892 A1 | 6/2012 | Reitmajer et al. |
| 2012/0197245 A1 | 8/2012 | Burnett |
| 2012/0203255 A1 | 8/2012 | Hawkins et al. |
| 2012/0221013 A1 | 8/2012 | Hawkins et al. |
| 2012/0232409 A1* | 9/2012 | Stahmann ..................... A61B 5/201 600/483 |
| 2012/0296367 A1 | 11/2012 | Grovender et al. |
| 2012/0330293 A1 | 12/2012 | Arai |
| 2013/0030431 A1 | 1/2013 | Adams |
| 2013/0030447 A1 | 1/2013 | Adams |
| 2013/0041355 A1 | 2/2013 | Heeren et al. |

(56) References Cited

U.S. PATENT DOCUMENTS

| | | |
|---|---|---|
| 2013/0046207 A1 | 2/2013 | Capelli |
| 2013/0046293 A1 | 2/2013 | Arai et al. |
| 2013/0053762 A1 | 2/2013 | Rontal et al. |
| 2013/0110003 A1 | 5/2013 | Surti |
| 2013/0116714 A1 | 5/2013 | Adams et al. |
| 2013/0165764 A1* | 6/2013 | Scheuermann ........ A61B 18/24 |
| | | 600/407 |
| 2013/0190803 A1 | 7/2013 | Angel et al. |
| 2013/0197614 A1 | 8/2013 | Gustus |
| 2013/0218054 A1 | 8/2013 | Sverdlik et al. |
| 2013/0226131 A1 | 8/2013 | Bacino et al. |
| 2013/0253466 A1 | 9/2013 | Campbell |
| 2013/0274726 A1 | 10/2013 | Takayama |
| 2013/0345617 A1 | 12/2013 | Wallace |
| 2014/0005576 A1 | 1/2014 | Adams |
| 2014/0005706 A1 | 1/2014 | Gelfand et al. |
| 2014/0012186 A1 | 1/2014 | Thyzel |
| 2014/0039002 A1 | 1/2014 | Adams et al. |
| 2014/0039358 A1 | 2/2014 | Zhou et al. |
| 2014/0039513 A1 | 2/2014 | Hakala |
| 2014/0046229 A1 | 2/2014 | Hawkins et al. |
| 2014/0046353 A1 | 2/2014 | Adams |
| 2014/0052146 A1 | 2/2014 | Curtis et al. |
| 2014/0052147 A1 | 2/2014 | Hakala et al. |
| 2014/0058294 A1 | 2/2014 | Gross et al. |
| 2014/0074111 A1 | 3/2014 | Hakala |
| 2014/0114198 A1 | 4/2014 | Samada et al. |
| 2014/0153087 A1 | 6/2014 | Hutchings et al. |
| 2014/0155990 A1 | 6/2014 | Nyuli |
| 2014/0180069 A1 | 6/2014 | Millett |
| 2014/0180126 A1 | 6/2014 | Millett |
| 2014/0180134 A1 | 6/2014 | Hoseit |
| 2014/0188094 A1 | 7/2014 | Islam |
| 2014/0228829 A1 | 8/2014 | Schmitt |
| 2014/0257144 A1 | 9/2014 | Capelli et al. |
| 2014/0257148 A1 | 9/2014 | Jie |
| 2014/0276573 A1 | 9/2014 | Miesel |
| 2014/0288570 A1 | 9/2014 | Adams |
| 2014/0309536 A1 | 10/2014 | Douk et al. |
| 2014/0336632 A1 | 11/2014 | Toth |
| 2014/0336637 A1 | 11/2014 | Agrawal |
| 2014/0357997 A1 | 12/2014 | Hartmann |
| 2015/0003900 A1 | 1/2015 | Ullrich et al. |
| 2015/0005576 A1 | 1/2015 | Diodone et al. |
| 2015/0039002 A1 | 2/2015 | Hawkins |
| 2015/0057648 A1* | 2/2015 | Swift ................ A61B 18/245 |
| | | 606/15 |
| 2015/0073430 A1 | 3/2015 | Hakala et al. |
| 2015/0080875 A1 | 3/2015 | Kasprzyk et al. |
| 2015/0105715 A1 | 4/2015 | Pikus et al. |
| 2015/0119870 A1 | 4/2015 | Rudie |
| 2015/0126990 A1 | 5/2015 | Sharma |
| 2015/0141764 A1 | 5/2015 | Harks et al. |
| 2015/0250542 A1 | 9/2015 | Islam |
| 2015/0276689 A1 | 10/2015 | Watanabe |
| 2015/0313732 A1 | 11/2015 | Fulton, III |
| 2015/0320432 A1 | 11/2015 | Adams |
| 2015/0342678 A1 | 12/2015 | Deladurantaye et al. |
| 2015/0359432 A1 | 12/2015 | Ehrenreich |
| 2015/0359557 A1 | 12/2015 | Shimokawa |
| 2016/0008016 A1 | 1/2016 | Cioanta et al. |
| 2016/0016016 A1 | 1/2016 | Taylor et al. |
| 2016/0018602 A1 | 1/2016 | Govari et al. |
| 2016/0022294 A1 | 1/2016 | Cioanta et al. |
| 2016/0038087 A1 | 2/2016 | Hunter |
| 2016/0095610 A1 | 4/2016 | Lipowski et al. |
| 2016/0135828 A1 | 5/2016 | Hawkins et al. |
| 2016/0135891 A1 | 5/2016 | Feldman |
| 2016/0143522 A1 | 5/2016 | Ransbury |
| 2016/0151639 A1 | 6/2016 | Scharf et al. |
| 2016/0183819 A1 | 6/2016 | Burnett |
| 2016/0183957 A1 | 6/2016 | Hakala et al. |
| 2016/0184020 A1 | 6/2016 | Kowalewski et al. |
| 2016/0184022 A1 | 6/2016 | Grace et al. |
| 2016/0184023 A1 | 6/2016 | Grace et al. |
| 2016/0184526 A1 | 6/2016 | Beyar |
| 2016/0184570 A1 | 6/2016 | Grace et al. |
| 2016/0228187 A1 | 8/2016 | Gross |
| 2016/0262784 A1 | 9/2016 | Grace et al. |
| 2016/0270806 A1 | 9/2016 | Wallace |
| 2016/0302762 A1 | 10/2016 | Stigall et al. |
| 2016/0234534 A1 | 11/2016 | Hawkins et al. |
| 2016/0324564 A1 | 11/2016 | Gerlach et al. |
| 2016/0331389 A1 | 11/2016 | Hakala et al. |
| 2016/0367274 A1 | 12/2016 | Wallace |
| 2016/0367275 A1 | 12/2016 | Wallace |
| 2017/0049463 A1 | 2/2017 | Popovic et al. |
| 2017/0056035 A1 | 3/2017 | Adams |
| 2017/0056087 A1 | 3/2017 | Buckley |
| 2017/0086867 A1 | 3/2017 | Adams |
| 2017/0119469 A1 | 5/2017 | Shimizu et al. |
| 2017/0119470 A1 | 5/2017 | Diamant et al. |
| 2017/0135709 A1 | 5/2017 | Nguyen et al. |
| 2017/0151421 A1 | 6/2017 | Asher |
| 2017/0192242 A1 | 7/2017 | Laycock |
| 2017/0209050 A1 | 7/2017 | Fengler et al. |
| 2017/0265942 A1 | 9/2017 | Grace et al. |
| 2017/0303946 A1 | 10/2017 | Ku et al. |
| 2017/0311965 A1 | 11/2017 | Adams |
| 2018/0008348 A1 | 1/2018 | Grace et al. |
| 2018/0042661 A1 | 2/2018 | Long |
| 2018/0042677 A1 | 2/2018 | Yu et al. |
| 2018/0045897 A1 | 2/2018 | Chia |
| 2018/0049877 A1 | 2/2018 | Venkatasubramanian |
| 2018/0085174 A1 | 3/2018 | Radtke et al. |
| 2018/0092763 A1 | 4/2018 | Dagan et al. |
| 2018/0095287 A1 | 4/2018 | Jeng et al. |
| 2018/0098779 A1 | 4/2018 | Betelia et al. |
| 2018/0152568 A1 | 6/2018 | Kat-kuoy |
| 2018/0214677 A1 | 8/2018 | Tarunaga |
| 2018/0238675 A1 | 8/2018 | Wan |
| 2018/0256250 A1 | 9/2018 | Adams et al. |
| 2018/0280005 A1 | 10/2018 | Parmentier |
| 2018/0303501 A1 | 10/2018 | Hawkins |
| 2018/0303503 A1 | 10/2018 | Eggert et al. |
| 2018/0303504 A1 | 10/2018 | Eggert et al. |
| 2018/0304053 A1 | 10/2018 | Eggert et al. |
| 2018/0323571 A1 | 11/2018 | Brown et al. |
| 2018/0333043 A1 | 11/2018 | Teriluc |
| 2018/0360482 A1 | 12/2018 | Nguyen |
| 2019/0029702 A1 | 1/2019 | De Cicco |
| 2019/0029703 A1 | 1/2019 | Wasdyke et al. |
| 2019/0069916 A1 | 3/2019 | Hawkins et al. |
| 2019/0072378 A1 | 3/2019 | Hane et al. |
| 2019/0097380 A1 | 3/2019 | Luft et al. |
| 2019/0099588 A1* | 4/2019 | Ramanath ......... A61M 25/1029 |
| 2019/0104933 A1 | 4/2019 | Stern |
| 2019/0117242 A1* | 4/2019 | Lawinger ............... A61B 18/26 |
| 2019/0150960 A1* | 5/2019 | Nguyen ........... A61B 17/22022 |
| 2019/0150961 A1 | 5/2019 | Tozzi |
| 2019/0167349 A1 | 6/2019 | Shamay |
| 2019/0175111 A1 | 6/2019 | Genereux et al. |
| 2019/0175300 A1 | 6/2019 | Hom |
| 2019/0175372 A1 | 6/2019 | Boydan et al. |
| 2019/0175407 A1 | 6/2019 | Bacher |
| 2019/0209368 A1 | 7/2019 | Park et al. |
| 2019/0232066 A1 | 8/2019 | Lim et al. |
| 2019/0247680 A1 | 8/2019 | Mayer |
| 2019/0262594 A1 | 8/2019 | Ogata et al. |
| 2019/0265419 A1 | 8/2019 | Tayebati |
| 2019/0282249 A1 | 9/2019 | Tran et al. |
| 2019/0282250 A1 | 9/2019 | Tran et al. |
| 2019/0321100 A1* | 10/2019 | Masotti .................. A61B 18/24 |
| 2019/0321101 A1* | 10/2019 | Masotti .................. A61B 18/24 |
| 2019/0328259 A1 | 10/2019 | Deno et al. |
| 2019/0365400 A1 | 12/2019 | Adams et al. |
| 2019/0380589 A1 | 12/2019 | Lloret |
| 2019/0388002 A1 | 12/2019 | Bozsak et al. |
| 2019/0388110 A1 | 12/2019 | Nguyen et al. |
| 2019/0388133 A1 | 12/2019 | Sharma |
| 2019/0388151 A1 | 12/2019 | Bhawalkar |
| 2020/0000484 A1 | 1/2020 | Hawkins |
| 2020/0008856 A1 | 1/2020 | Harmouche |
| 2020/0022754 A1 | 1/2020 | Cottone |

(56) References Cited

U.S. PATENT DOCUMENTS

| | | |
|---|---|---|
| 2020/0038087 A1 | 2/2020 | Harmouche |
| 2020/0046429 A1 | 2/2020 | Tschida et al. |
| 2020/0046949 A1 | 2/2020 | Chisena et al. |
| 2020/0054352 A1 | 2/2020 | Brouillette et al. |
| 2020/0060814 A1 | 2/2020 | Murphy |
| 2020/0061931 A1 | 2/2020 | Brown et al. |
| 2020/0069371 A1 | 3/2020 | Brown et al. |
| 2020/0085458 A1 | 3/2020 | Nguyen et al. |
| 2020/0085459 A1 | 3/2020 | Adams |
| 2020/0101269 A1 | 4/2020 | Hayes |
| 2020/0107960 A1 | 4/2020 | Bacher |
| 2020/0108236 A1 | 4/2020 | Salazar et al. |
| 2020/0129195 A1 | 4/2020 | McGowan et al. |
| 2020/0129741 A1 | 4/2020 | Kawwas |
| 2020/0155812 A1 | 5/2020 | Zhang et al. |
| 2020/0197019 A1 | 6/2020 | Harper |
| 2020/0205890 A1 | 7/2020 | Harlev |
| 2020/0246032 A1 | 8/2020 | Betelia et al. |
| 2020/0289202 A1 | 9/2020 | Miyagawa et al. |
| 2020/0297366 A1 | 9/2020 | Nguyen et al. |
| 2020/0337717 A1 | 10/2020 | Walzman |
| 2020/0383724 A1 | 12/2020 | Adams et al. |
| 2020/0397230 A1 | 12/2020 | Massimini et al. |
| 2020/0397453 A1* | 12/2020 | McGowan ....... A61B 17/22012 |
| 2020/0398033 A1 | 12/2020 | McGowan et al. |
| 2020/0405333 A1 | 12/2020 | Massimini et al. |
| 2020/0405391 A1 | 12/2020 | Massimini et al. |
| 2020/0406009 A1 | 12/2020 | Massimini |
| 2020/0406010 A1 | 12/2020 | Massimini et al. |
| 2021/0038237 A1 | 2/2021 | Adams |
| 2021/0085347 A1 | 3/2021 | Phan et al. |
| 2021/0085348 A1 | 3/2021 | Nguyen |
| 2021/0085383 A1 | 3/2021 | Vo et al. |
| 2021/0116302 A1 | 4/2021 | Jean-Ruel |
| 2021/0128241 A1 | 5/2021 | Schultheis |
| 2021/0137598 A1 | 5/2021 | Cook et al. |
| 2021/0153939 A1 | 5/2021 | Cook |
| 2021/0177442 A1 | 6/2021 | Girdhar et al. |
| 2021/0177445 A1 | 6/2021 | Nguyen |
| 2021/0186613 A1 | 6/2021 | Cook |
| 2021/0212765 A1 | 7/2021 | Verhagen |
| 2021/0220052 A1 | 7/2021 | Cook |
| 2021/0220053 A1 | 7/2021 | Cook |
| 2021/0244473 A1 | 8/2021 | Cook et al. |
| 2021/0267685 A1 | 9/2021 | Schultheis |
| 2021/0275247 A1 | 9/2021 | Schultheis |
| 2021/0275249 A1 | 9/2021 | Massimini et al. |
| 2021/0282792 A1 | 9/2021 | Adams et al. |
| 2021/0290259 A1 | 9/2021 | Hakala et al. |
| 2021/0290286 A1 | 9/2021 | Cook |
| 2021/0290305 A1 | 9/2021 | Cook |
| 2021/0298603 A1 | 9/2021 | Feldman |
| 2021/0307828 A1 | 10/2021 | Schultheis |
| 2021/0330384 A1 | 10/2021 | Cook |
| 2021/0338258 A1 | 11/2021 | Hawkins et al. |
| 2021/0353359 A1 | 11/2021 | Cook |
| 2021/0369348 A1 | 12/2021 | Cook |
| 2021/0378743 A1 | 12/2021 | Massimini et al. |
| 2021/0378744 A1 | 12/2021 | Fanier et al. |
| 2021/0386479 A1 | 12/2021 | Massimini et al. |
| 2022/0000505 A1 | 1/2022 | Hauser |
| 2022/0000506 A1 | 1/2022 | Hauser |
| 2022/0000507 A1 | 1/2022 | Hauser |
| 2022/0000508 A1 | 1/2022 | Schmitt et al. |
| 2022/0000509 A1 | 1/2022 | Laser et al. |
| 2022/0000551 A1 | 1/2022 | Govari et al. |
| 2022/0008130 A1 | 1/2022 | Massimini et al. |
| 2022/0008693 A1 | 1/2022 | Humbert et al. |
| 2022/0015785 A1 | 1/2022 | Hakala et al. |
| 2022/0021190 A1 | 1/2022 | Pecquois |
| 2022/0022902 A1 | 1/2022 | Spano |
| 2022/0022912 A1 | 1/2022 | Efremkin |
| 2022/0023528 A1 | 1/2022 | Long et al. |
| 2022/0071704 A1 | 3/2022 | Le |
| 2022/0168594 A1 | 6/2022 | Mayer |
| 2022/0183738 A1 | 6/2022 | Flores et al. |
| 2022/0218402 A1 | 7/2022 | Schultheis |
| 2022/0249165 A1 | 8/2022 | Cook |
| 2022/0273324 A1 | 9/2022 | Schultheis |
| 2022/0287732 A1 | 9/2022 | Anderson et al. |
| 2022/0313293 A1 | 10/2022 | Singh |
| 2022/0338890 A1 | 10/2022 | Anderson et al. |
| 2022/0354578 A1 | 11/2022 | Cook |
| 2022/0387106 A1 | 12/2022 | Cook |
| 2023/0013920 A1 | 1/2023 | Massimini |
| 2023/0248376 A1 | 8/2023 | Anderson et al. |
| 2023/0310073 A1 | 10/2023 | Adams et al. |
| 2023/0414234 A1 | 12/2023 | Anderson et al. |
| 2024/0058060 A1 | 2/2024 | Cook |
| 2024/0065712 A1 | 2/2024 | Schultheis |
| 2024/0122648 A1 | 4/2024 | Cook |
| 2024/0189543 A1 | 6/2024 | Salinas |
| 2024/0216062 A1 | 7/2024 | Cook |
| 2024/0277410 A1 | 8/2024 | Cook |
| 2024/0285296 A1 | 8/2024 | Vo |
| 2024/0382258 A1 | 11/2024 | Schultheis |

FOREIGN PATENT DOCUMENTS

| | | |
|---|---|---|
| AU | 2022227829 | 9/2022 |
| CA | 2229806 | 3/1997 |
| CA | 2281519 | 8/1998 |
| CA | 2983655 | 10/2016 |
| CA | 3209797 | 9/2022 |
| CN | 102057422 | 5/2011 |
| CN | 109223100 | 1/2019 |
| CN | 110638501 | 1/2020 |
| CN | 110638501 A | 1/2020 |
| CN | 106794043 | 3/2020 |
| CN | 11399346 | 1/2022 |
| CN | 107411805 | 1/2022 |
| CN | 107899126 | 1/2022 |
| CN | 109475378 | 1/2022 |
| CN | 113876388 | 1/2022 |
| CN | 113877044 | 1/2022 |
| CN | 113907838 | 1/2022 |
| CN | 113951972 A | 1/2022 |
| CN | 113951973 A | 1/2022 |
| CN | 113974765 | 1/2022 |
| CN | 113974826 A | 1/2022 |
| CN | 215384399 | 1/2022 |
| CN | 215386905 | 1/2022 |
| CN | 215458400 | 1/2022 |
| CN | 215458401 | 1/2022 |
| CN | 215505065 | 1/2022 |
| CN | 215534803 | 1/2022 |
| CN | 215537694 | 1/2022 |
| CN | 215584286 | 1/2022 |
| CN | 215606068 | 1/2022 |
| CN | 215651393 | 1/2022 |
| CN | 215651394 | 1/2022 |
| CN | 215651484 | 1/2022 |
| CN | 215653328 | 1/2022 |
| CN | 114053552 | 2/2022 |
| CN | 115175625 | 10/2022 |
| DE | 3038445 A1 | 5/1982 |
| DE | 3836337 A | 4/1990 |
| DE | 3913027 A1 | 10/1990 |
| DE | 69431758 | 1/2003 |
| DE | 10230626 | 1/2004 |
| DE | 202008016760 | 3/2009 |
| DE | 102007046902 | 4/2009 |
| DE | 102008034702 | 1/2010 |
| DE | 102009007129 | 8/2010 |
| DE | 202010009899 | 11/2010 |
| DE | 102013201928 | 8/2014 |
| DE | 102020117713 | 1/2022 |
| EP | 0119296 | 9/1984 |
| EP | 0261831 B1 | 6/1992 |
| EP | 558297 A2 | 9/1993 |
| EP | 0571306 A1 | 11/1993 |
| EP | 1179993 A1 | 2/2002 |
| EP | 1946712 | 7/2008 |
| EP | 1946712 A1 | 7/2008 |

(56) References Cited

FOREIGN PATENT DOCUMENTS

| | | |
|---|---|---|
| EP | 1453566 | 9/2008 |
| EP | 2157569 | 2/2010 |
| EP | 2879595 | 6/2015 |
| EP | 2879595 A1 | 6/2015 |
| EP | 2944264 A1 | 6/2015 |
| EP | 3226795 A1 | 10/2017 |
| EP | 3266487 | 1/2018 |
| EP | 3318204 | 5/2018 |
| EP | 2879607 | 2/2019 |
| EP | 3461438 A1 | 4/2019 |
| EP | 3473195 A1 | 4/2019 |
| EP | 3643260 A1 | 4/2020 |
| EP | 3076881 B1 | 1/2022 |
| EP | 3932342 | 1/2022 |
| EP | 3936140 | 1/2022 |
| EP | 3960099 | 3/2022 |
| EP | 4051154 | 9/2022 |
| EP | 4129213 | 2/2023 |
| EP | 4277537 | 11/2023 |
| EP | 4297669 | 1/2024 |
| EP | 3182931 | 6/2024 |
| EP | 3950036 | 8/2024 |
| GB | 1082397 | 9/1967 |
| JP | S62275446 A | 11/1987 |
| JP | 1996089511 | 4/1996 |
| JP | H09117407 | 5/1997 |
| JP | 2004519296 | 7/2004 |
| JP | 2008506447 | 3/2008 |
| JP | 2008083273 | 4/2008 |
| JP | 2009519777 | 5/2009 |
| JP | 2009213589 | 9/2009 |
| JP | 2011524203 | 9/2011 |
| JP | 4805208 | 11/2011 |
| JP | 4808620 | 11/2011 |
| JP | 2014123147 | 7/2014 |
| JP | 2015217215 | 12/2015 |
| JP | 2018538077 | 12/2018 |
| JP | 2024511710 | 3/2024 |
| KR | 20050098932 | 10/2005 |
| KR | 20080040111 | 5/2008 |
| KR | 20160090877 A | 8/2016 |
| KR | 20180054041 | 5/2018 |
| WO | WO9007904 A1 | 7/1990 |
| WO | WO9105332 A1 | 4/1991 |
| WO | 9203095 A1 | 3/1992 |
| WO | 1992008515 A2 | 5/1992 |
| WO | WO9208515 | 5/1992 |
| WO | WO9524867 | 9/1995 |
| WO | WO-9524867 A1 * | 9/1995 ............. A61B 18/26 |
| WO | 9902095 A1 | 1/1999 |
| WO | 9920189 A1 | 4/1999 |
| WO | WO200067648 | 11/2000 |
| WO | WO2000067648 A1 | 11/2000 |
| WO | 2001003599 A1 | 1/2001 |
| WO | WO0103599 | 1/2001 |
| WO | 2006006169 A2 | 1/2006 |
| WO | WO2006006169 | 1/2006 |
| WO | WO2009121017 | 10/2009 |
| WO | WO2009149321 A1 | 12/2009 |
| WO | WO2009152352 A2 | 12/2009 |
| WO | 2010042653 A1 | 4/2010 |
| WO | WO2011094379 | 8/2011 |
| WO | 2011126580 A2 | 10/2011 |
| WO | WO2011126580 A3 | 10/2011 |
| WO | WO2012025833 | 3/2012 |
| WO | WO2012042619 | 4/2012 |
| WO | WO20120052924 A1 | 4/2012 |
| WO | WO2012058156 | 5/2012 |
| WO | WO2012099974 A2 | 7/2012 |
| WO | WO20120120495 A2 | 9/2012 |
| WO | WO2013119662 | 8/2013 |
| WO | 20130169807 A1 | 11/2013 |
| WO | WO2013169807 | 11/2013 |
| WO | WO2014022436 A1 | 2/2014 |
| WO | WO2014025397 A1 | 2/2014 |
| WO | WO20140022867 A1 | 2/2014 |
| WO | WO2014138582 | 9/2014 |
| WO | WO2015056662 | 4/2015 |
| WO | WO2015097251 A2 | 7/2015 |
| WO | 2015177790 A1 | 11/2015 |
| WO | WO2016014999 | 1/2016 |
| WO | WO2016089683 A1 | 6/2016 |
| WO | WO2016090175 | 6/2016 |
| WO | WO2016098670 | 6/2016 |
| WO | WO2016109739 | 7/2016 |
| WO | WO2016143556 | 9/2016 |
| WO | WO2016151595 A1 | 9/2016 |
| WO | WO2017004432 A1 | 1/2017 |
| WO | WO20170192869 A1 | 11/2017 |
| WO | 20180022641 A1 | 2/2018 |
| WO | WO2018022593 A1 | 2/2018 |
| WO | WO2018083666 | 5/2018 |
| WO | 2018175322 A1 | 9/2018 |
| WO | WO2018175322 | 9/2018 |
| WO | WO2018191013 | 10/2018 |
| WO | WO2019200201 A1 | 10/2019 |
| WO | WO2019215869 A1 | 11/2019 |
| WO | WO2019222843 | 11/2019 |
| WO | WO2020056031 | 3/2020 |
| WO | WO20200086361 A1 | 4/2020 |
| WO | WO2020089876 A1 | 5/2020 |
| WO | WO2020157648 | 8/2020 |
| WO | WO2020256898 | 12/2020 |
| WO | WO2020256898 A1 | 12/2020 |
| WO | WO2020256949 | 12/2020 |
| WO | WO2020256949 A1 | 12/2020 |
| WO | WO2020263469 A1 | 12/2020 |
| WO | WO2020263685 A1 | 12/2020 |
| WO | WO2020263687 A1 | 12/2020 |
| WO | WO2020263688 A1 | 12/2020 |
| WO | WO2020263689 A1 | 12/2020 |
| WO | WO2021061451 | 4/2021 |
| WO | WO2021067563 | 4/2021 |
| WO | 2021086571 A1 | 5/2021 |
| WO | 2021101766 A1 | 5/2021 |
| WO | WO2021096922 A1 | 5/2021 |
| WO | WO2021101766 | 5/2021 |
| WO | WO2021126762 A1 | 6/2021 |
| WO | WO2021162855 A1 | 8/2021 |
| WO | WO2021173417 A1 | 9/2021 |
| WO | WO2021183367 A1 | 9/2021 |
| WO | WO2021183401 A1 | 9/2021 |
| WO | WO2021188233 A1 | 9/2021 |
| WO | WO2021202248 A1 | 10/2021 |
| WO | WO2021231178 A1 | 11/2021 |
| WO | WO2021247685 A1 | 12/2021 |
| WO | WO2021257425 A1 | 12/2021 |
| WO | WO2022007490 | 1/2022 |
| WO | WO2022008440 | 1/2022 |
| WO | WO2022010767 A1 | 1/2022 |
| WO | WO2022055784 | 3/2022 |
| WO | WO2022125525 | 6/2022 |
| WO | WO2022154954 | 7/2022 |
| WO | WO2022173719 | 8/2022 |
| WO | WO2022183075 | 9/2022 |
| WO | WO2022187058 | 9/2022 |
| WO | WO2022216488 | 10/2022 |
| WO | WO2022240674 | 11/2022 |
| WO | WO2022260932 | 12/2022 |
| WO | WO2023107334 | 6/2023 |

OTHER PUBLICATIONS

Shariat, Mohammad H., et al. "Localization of the ectopic spiral electrical source using intracardiac electrograms during atrial fibrillation." 2015 IEEE 28th Canadian Conference on Electrical and Computer Engineering (CCECE). IEEE, 2015.

Nademanee, Koonlawee, et al. "A new approach for catheter ablation of atrial fibrillation: mapping of the electrophysiologic substrate." Journal of the American College of Cardiology 43.11 (2004): 2044-2053.

Calkins, Hugh. "Three dimensional mapping of atrial fibrillation:

(56) References Cited

OTHER PUBLICATIONS techniques and necessity." Journal of interventional cardiac electrophysiology 13.1 (2005): 53-59.
Shariat, Mohammad Hassan. Processing the intracardiac electrogram for atrial fibrillation ablation. Diss. Queen's University (Canada), 2016.
Meng et al., "Accurate Recovery of Atrial Endocardial Potential Maps From Non-contact Electrode Data." Auckland Bioengineering Institute. (ID 1421).
Jiang et al., "Multielectrode Catheter for Substrate Mapping for Scar-related VT Ablation: A Comparison Between Grid Versus Linear Configurations." UChicago Medicine, Center for Arrhythmia Care, Chicago IL (ID 1368).
Sacher et al., "Comparison of Manual Vs Automatic Annotation to Identify Abnormal Substrate for Scar Related VT Ablation." LIRYC Institute, Bordeaux University Hospital, France (ID 1336).
Oriel Instruments, "Introduction to Beam Splitters for Optical Research Applications", Apr. 2014, pp. 1-9, https://www.azoptics.com/Article.aspx?ArticaID=871.
International Search Report and Written Opinion dated Apr. 12, 2021 in PCT Application Serial No. PCT/US2020/059960.
International Search Report and Written Opinion dated Apr. 13, 2021 in PCT Application Serial No. PCT/US2020/064846.
International Search Report and Written Opinion dated Apr. 13, 2021 in PCT Application Serial No. PCT/US2021/013944.
International Search Report and Written Opinion dated May 25, 2021 in PCT Application Serial No. PCT/US2021/017604.
International Search Report and Written Opinion, PCT Application Serial No. PCT/US2022/047751 issued Feb. 10, 2023, by the European Patent Office. (56PCT).
International Search Report and Written Opinion dated Nov. 8, 2022 in PCT Application Serial No. PCT US/2022/039678.
International Search Report and Written Opinion, issued by the EP/ISA, in PCT/US2021/048819, dated Jan. 14, 2022.
International Search Report and Written Opinion dated Sep. 11, 2020 in PCT Application Serial No. PCT/US2020038517.
International Search Report and Written Opinion dated Sep. 9, 2020 in PCT Application Serial No. PCT/US2020038530.
International Search Report and Written Opinion dated Sep. 11, 2020 in PCT Application Serial No. PCT/US2020038521.
International Search Report and Written Opinion dated Sep. 7, 2020 in PCT Application Serial No. PCT/US2020034642.
International Preliminary Report on Patentability dated Sep. 15, 2020 in PCT Application Serial No. PCT/US2019/022009.
International Search Report and Written Opinion dated Jul. 29, 2020 in PCT Application Serial No. PCT/US2020/034005.
International Search Report and Written Opinion dated Jun. 2, 2021 in PCT Application Serial No. PCT/US2021/018522.
International Search Report and Written Opinion dated Jun. 2, 2021 in PCT Application Serial No. PCT/US2021/015204.
International Search Report and Written Opinion dated Jun. 17, 2021 in PCT Application Serial No. PCT/US2021/020934.
International Search Report and Written Opinion dated Jul. 13, 2021 in PCT Application Serial No. PCT/US2021/024216.
International Search Report and Written Opinion dated Jun. 22, 2021 in PCT Application Serial No. PCT/US2021/020937.
International Search Report and Written Opinion dated Jun. 24, 2021 in PCT Application Serial No. PCT/US2021/021272.
International Search Report and Written Opinion dated Sep. 14, 2020 in PCT Application Serial No. PCT/US2020/038523.
International Search Report and Written Opinion dated Oct. 2, 2020 in PCT Application Serial No. PCT/US2020/036107.
International Search Report and Written Opinion dated Aug. 25, 2022 in PCT Application Serial No. PCT US/2022/028035.
International Search Report and Written Opinion dated Sep. 15, 2022 in PCT Application Serial No. PCT US/2022/032045.
International Search Report and Written Opinion dated Apr. 4, 2022 in PCT Application Serial No. PCT/US2021/062170.
International Search Report and Written Opinion dated Apr. 4, 2022 in PCT Application Serial No. PCT/US2021/065073.
Partial Search Report and Provisional Opinion dated May 3, 2022 in PCT Application No. PCT/US2022/015577.
International Search Report and Written Opinion dated May 13, 2022 in PCT Application Serial No. PCT/US2022/017562.
PathFinder Digital, "Free Space Optics vs. Fiber Optics", 2023.
International Search Report and Written Opinion, issued in Application Serial No. PCT/US2023/016152, dated Jul. 12, 2023.
Schafter+Kirchhoff, Laser Beam Couplers series 60SMS for coupling into single-mode and polarization-maintaining fiber cables, Schafter+Kirchhoff, pp. 1-5, Germany.
International Search Report and Written Opinion dated Jan. 29, 2020 in PCT Application Serial No. PCT/US2020/059961.
International Search Report and Written Opinion dated Jan. 20, 2020 in PCT Application Serial No. PCT/US2020/054792.
Davletshin, Yevgeniy R., "A Computational Analysis of Nanoparticle-Mediated Optical Breakdown", A dissertation presented to Ryerson University in Partial Fulfillment of the requirements for the degree of Doctor of Philosophy in the Program of Physics, Toronto, Ontario, CA 2017.
Vogel, A., et al. "Acoustic transient generation by laser-produced cavitation bubbles near solid boundaries", Journal Acoustical Society of America, 1988, pp. 719-731, vol. 84.
Asshauer, T., et al. "Acoustic transient generation by holmium-laser-induced cavitation bubbles", Journal of Applied Physics, Nov. 1, 1994, pp. 5007-5013, vol. 76, No. 9, American Institute of Physics.
Zheng, W., "Optic Lenses Manufactured on Fiber Ends", 2015, Splicer Engineering AFL, Duncan, SC USA.
Ali, Ziad A., et al. "Optical Coherence Tomography Characterization of Coronary Lithoplasty for Treatment of Calcified Lesions", JACC: Cardiovascular Imaging, 2017, pp. 897-906, vol. 109, No. 8, Elsevier.
Ali, Ziad A., et al. "Intravascular lithotripsy for treatment of stent underexpansion secondary to severe coronary calcification" 2018, European Society of Cardiology.
Ashok, Praveen C., et al. "Raman spectroscopy bio-sensor for tissue discrimination in surgical robotics—full article", Journal of Biophotonics, 2014, pp. 103-109, vol. 7, No. 1-2.
Ashok, Praveen C., et al. "Raman spectroscopy bio-sensor for tissue discrimination in surgical robotics—proof" Journal of Biophotonics 7, 2014, No. 1-2.
Bian, D. C., et al. "Experimental Study of Pulsed Discharge Underwater Shock-Related Properties in Pressurized Liquid Water", Hindawi Advances in Materials Science and Engineering, Jan. 2018, 12 pages, vol. 2018, Article ID 8025708.
Bian, D. C., et al. "Study on Breakdown Delay Characteristics Based on High-voltage Pulse Discharge in Water with Hydrostatic Pressure", Journal of Power Technologies 97(2), 2017, pp. 89-102.
Doukas, A. G., et al. "Biological effects of laser induced shock waves: Structural and functional cell damage in vitro", Ultrasound in Medicine and Biology, 1993, pp. 137-146, vol. 19, Issue 2, Pergamon Press, USA.
Brodmann, Marianne et al. "Safety and Performance of Lithoplasty for Treatment of Calcified Peripheral Artery Lesions", JACC, 2017, vol. 70, No. 7.
Brouillette, M., "Shock Waves at Microscales", 2003, pp. 3-12, Springer-Verlag.
Mirshekari, G., et al. "Shock Waves in Microchannels", 2013, pp. 259-283, vol. 724, Cambridge University Press.
"Bubble Dynamics and Shock Waves", Springer, 2013, Springer-Verlag, Berlin Heildelberg.
Hardy, Luke A., et al. "Cavitation Bubble Dynamics During Thulium Fiber Laser Lithotripsy", SPIE, Feb. 29, 2016, vol. 9689, San Francisco, California, USA.
Claverie, A., et al. "Experimental characterization of plasma formation and shockwave propagation induced by high power pulsed underwater electrical discharge", Review of Scientific Instruments, 2014, American Institute of Physics.
Blackmon, Richard L., et al. "Comparison of holmium: YAG and thulium fiber laser lithotripsy ablation thresholds, ablation rates, and retropulsion effects", Journal of Biomedical Optics, 2011, vol. 16(7), SPIE.

(56) References Cited

OTHER PUBLICATIONS

Debasis, P., et al. "Continuous-wave and quasi-continuous wave thulium-doped all-fiber laser: implementation on kidney stone fragmentations", Applied Optics, Aug. 10, 2016, vol. 55, No. 23, Optical Society of America.

Cook, Jason R., et al. "Tissue mimicking phantoms for photoacoustic and ultrasonic imaging", Biomedical Optics Express, 2011, vol. 2, No. 11, Optical Society of America.

Deckelbaum, Lawrence I., "Coronary Laser Angioplasty", Lasers in Surgery and Medicine, 1994, pp. 101-110, Wiley-Liss Inc.

Costanzo, F., "Underwater Explosion Phenomena and Shock Physics", Research Gate, 2011.

Mizeret, J. C., et al. "Cylindrical fiber optic light diffuser for medical applications", Lasers in Surgery and Medicine, 1996, pp. 159-167, vol. 19, Issue 2, Wiley-Liss Inc., Lausanne, Switzerland.

De Silva, K., et al. "A Calcific, Undilatable Stenosis Lithoplasty, a New Tool in the Box?", JACC: Cardiovascular Interventions, 2017, vol. 10, No. 3, Elsevier.

Vesselov, L., et al. "Design and performance of thin cylindrical diffusers created in Ge-doped multimode optical fibers", Applied Optics, 2005, pp. 2754-2758, vol. 44, Issue 14, Optical Society of America.

Hutchens, Thomas C., et al. "Detachable fiber optic tips for use in thulium fiber laser lithotripsy", Journal of Biomedical Optics, Mar. 2013, vol. 18(3), SPIE.

Kostanski, Kris L., et al. "Development of Novel Tunable Light Scattering Coating Materials for Fiber Optic Diffusers in Photodynamic Cancer Therapy", Journal of Applied Polymer Science, 2009, pp. 1516-1523, vol. 112, Wiley InterScience.

Kristiansen, M., et al. "High Voltage Water Breakdown Studies", DoD, 1998, Alexandria, VA, USA.

Dwyer, J. R., et al. "A study of X-ray emission from laboratory sparks in air at atmospheric pressure", Journal of Geophysical Research, 2008, vol. 113, American Geophysical Union.

Jansen, Duco E., et al. "Effect of Pulse Duration on Bubble Formation and Laser-Induced Pressure Waves During Holmium Laser Ablation", Lasers in Surgery and Medicine 18, 1996, pp. 278-293, Wiley-Liss Inc., Austin, TX, USA.

Shangguan, HanQun et al. "Effects of Material Properties on Laser-induced Bubble Formation in Absorbing Liquids and on Submerged Targets", SPIE, 1997, pp. 783-791, vol. 2869.

Varghese, B., et al. "Effects of polarization and absorption on laser induced optical breakdown threshold for skin rejuvenation", SPIE, Mar. 9, 2016, vol. 9740, SPIE, San Francisco, USA.

Varghese, B., et al. "Effects of polarization and apodization on laser induced optical breakdown threshold", Optics Express, Jul. 29, 2013, vol. 21, No. 15, Optical Society of America.

Bonito, Valentina, "Effects of polarization, plasma and thermal initiation pathway on irradiance threshold of laser induced optical breakdown", Philips Research, 2013, The Netherlands.

Vogel, A. et al. "Energy balance of optical breakdown in water at nanosecond to femtosecond time scales", Applied Physics B 68, 1999, pp. 271-280, Springer-Verlag.

Kang, Hyun W., et al. "Enhanced photocoagulation with catheter based diffusing optical device", Journal of Biomedical Optics, Nov. 2012, vol. 17(11), SPIE.

Esch, E., et al. "A Simple Method for Fabricating Artificial Kidney Stones of Different Physical Properties", National Institute of Health Public Access Author Manuscript, Aug. 2010.

Isner, Jeffrey M., et al. "Excimer Laser Atherectomy", Circulation, Jun. 1990, vol. 81, No. 6, American Heart Association, Dallas, TX, USA.

Israel, Douglas H., et al. "Excimer Laser-Facilitated Balloon Angioplasty of a Nondilateable Lesion", JACC, Oct. 1991, vol. 18, No. 4, American College of Cardiology, New York, USA.

Van Leeuwen, Ton G., et al. "Excimer Laser Induced Bubble: Dimensions, Theory, and Implications for Laser Angioplasty", Lasers in Surgery and Medicine 18, 1996, pp. 381-390, Wiley-Liss Inc., Utrecht, The Netherlands.

Nguyen, H., et al. "Fabrication of multipoint side-firing optical fiber by laser micro-ablation", Optics Letters, May 1, 2017, vol. 42, No. 9, Optical Society of America.

Zheng, W., "Optic Lenses Manufactured on Fiber Ends", 2015, IEEE, Duncan, SC, USA.

Whitesides, George M., et al. "Fluidic Optics", 2006, vol. 6329, SPIE, Cambridge, MA, USA.

Forero, M., et al. "Coronary lithoplasty: a novel treatment for stent underexpansion", Cardiovascular Flashlight, 2018, European Society of Cardiology.

Ghanate, A. D., et al. "Comparative evaluation of spectroscopic models using different multivariate statistical tools in a multicancer scenario", Journal of Biomedical Optics, Feb. 2011, pp. 1-9, vol. 16(2), SPIE.

Roberts, Randy M., et al. "The Energy Partition of Underwater Sparks", The Journal of the Acoustical Society of America, Jun. 1996, pp. 3465-3474, Acoustical Society of America, Austin, TX, USA.

Blackmon, Richard L., et al. "Holmium: YAG Versus Thulium Fiber Laser Lithotripsy", Lasers in Surgery and Medicine, 2010, pp. 232-236, Wiley-Liss Inc.

Varghese, B., "Influence of absorption induced thermal initiation pathway on irradiance threshold for laser induced breakdown", Biomedical Optics Express, 2015, vol. 6, No. 4, Optical Society of America.

Noack, J., "Influence of pulse duration on mechanical effects after laser-induced breakdown in water", Journal of Applied Physics, 1998, pp. 7488-EOA, vol. 83, American Institute of Physics.

Van Leeuwen, Ton G., et al. "Intraluminal Vapor Bubble Induced by Excimer Laser Pulse Causes Microsecond Arterial Dilation and Invagination Leading to Extensive Wall Damage in the Rabbit", Circulation, Apr. 1993, vol. 87, No. 4, American Heart Association, Dallas, TX, USA.

International Search Report and Written Opinion, issued by the European Patent Office for PCT/2021/XXX, dated Sep. 30, 2021.

International Search Report and Written Opinion dated Jun. 28, 2022, in PCT Application Serial No. PCT/US2022/015577.

International Search Report and Written Opinion dated Jun. 27, 2022, in PCT Application Serial No. PCT/US2022/022460.

Medlight, "Cylindrical light diffuser Model RD-ML", Medlight S.A., Switzerland. 2015. (This reference was cited in a prior Information Disclosure Statement. However, the relevant date was missing. The date has now been added.).

Medlight, "Cylindircal light diffuser Model RD", Medlight S.A., Switzerland. 2015. (This reference was cited in a prior Information Disclosure Statement. However, the relevant date was missing. The date has now been added.).

Ohl, Siew-Wan, et al. "Bubbles with shock waves and ultrasound: a review", Interface Focus, pp. 1-15, vol. 5, The Royal Society Publishing. Oct. 2015. This reference was cited in a prior Information Disclosure Statement. However, the relevant date was missing. The date has now been added.).

Schafter+Kirchhoff, Laser Beam Couplers series 60SMS for coupling into single-mode and polarization-maintaining fiber cables, Schafter+Kirchhoff, pp. 1-5, Germany. Dec. 2, 2021. (This reference was cited in a prior Information Disclosure Statement. However, the relevant date was missing. The date has now been added.).

Meng et al., "Accurate Recovery of Atrial Endocardial Potential Maps From Non-contact Electrode Data." Auckland Bioengineering Institute. (ID 1421). May 2019. (This reference was cited in a prior Information Disclosure Statement. However, the relevant date was missing. The date has now been added.).

Jiang et al., "Multielectrode Catheter for Substrate Mapping for Scar-related VT Ablation: A Comparison Between Grid Versus Linear Configurations." UChicago Medicine, Center for Arrhythmia Care, Chicago IL (Id 1368). Poster for conference in San Francisco, May 8-11, 2019. (This reference was cited in a prior Information Disclosure Statement. However, the relevant date was missing. The date has now been added.).

Sacher et al., "Comparison of Manual Vs Automatic Annotation to Identify Abnormal Substrate for Scar Related VT Ablation." LIRYC Institute, Bordeaux University Hospital, France (ID 1336). Poster for conference in San Francisco, May 8-11, 2019. (This reference

(56) References Cited

OTHER PUBLICATIONS was cited in a prior Information Disclosure Statement. However, the relevant date was missing. The date has now been added.).
International Search Report and Written Opinion dated Aug. 20, 2021 in PCT Application Serial No. PCT/US2021/031130.
AccuCoat, "Beamsplitter: Divide, combine & conquer"; 2023.
Lin et al., "Photoacoustic imaging", Science Direct; 2021.
Zhou et al., "Photoacoustic Imaging with fiber optic technology: A review", Science Direct; 2020.
International Search Report and Written Opinion issued by the European Patent Office, for Serial No. PCT/US2022/053775, dated Apr. 21, 2023. (Re 45PCT).
International Search Report and Written Opinion issued by the European Patent Office, for Serial No. PCT/US2023/011497, dated Apr. 28, 2023. (Re 54PCT).
International Search Report and Written Opinion issued by the European Patent Office, for Serial No. PCT/US2023/012599, dated May 19, 2023. (Re 57PCT).
International Search Report and Written Opinion dated Feb. 19, 2021 in PCT Application Serial No. PCT/US2020/059960.
Shen, Yajie et al. "High-peak-power and narrow-linewidth Q-switched Ho: YAG laser in-band pumped at 1931 nm." Applied Physics Express 13.5 (2020): 052006. (Year 2020).
Vogel, A., et al. "Intraocular Photodisruption With Picosecond and Nanosecond Laser Pulses: Tissue Effects in Cornea, Lens, and Retina", Investigative Ophthalmology & Visual Science, Jun. 1994, pp. 3032-3044, vol. 35, No. 7, Association for Research in Vision and Ophthalmology.
Jones, H. M., et al. "Pulsed dielectric breakdown of pressurized water and salt solutions", Journal of Applied Physics, Jun. 1998, pp. 795-805, vol. 77, No. 2, American Institute of Physics.
Kozulin, I., et al. "The dynamic of the water explosive vaporization on the flat microheater", Journal of Physics: Conference Series, 2018, pp. 1-4, IOP Publishing, Russia.
Cross, F., "Laser Angioplasty", Vascular Medicine Review, 1992, pp. 21-30, Edward Arnold.
Doukas, A. G., et al. "Laser-generated stress waves and their effects on the cell membrane", IEEE Journal of Selected Topics in Quantum Electronics, 1999, pp. 997-1003, vol. 5, Issue 4, IEEE.
Noack, J., et al. "Laser-Induced Plasma Formation in Water at Nanosecond to Femtosecond Time Scales: Calculation of Thresholds, Absorption Coefficients, and Energy Density", IEEE Journal of Quantum Electronics, 1999, pp. 1156-1167, vol. 35, No. 8, IEEE.
Pratsos, A., "The use of Laser for the treatment of coronary artery disease", Bryn Mawr Hospital, 2010.
Li, Xian-Dong, et al. "Influence of deposited energy on shock wave induced by underwater pulsed current discharge", Physics of Plasmas, 2016, vol. 23, American Institute of Physics.
Logunov, S., et al. "Light diffusing optical fiber illumination", Renewable Energy and the Environment Congress, 2013, Corning, NY, USA.
Maxwell, A. D., et al. "Cavitation clouds created by shock scattering from bubbles during histotripsy", Acoustical Society of America, 2011, pp. 1888-1898, vol. 130, No. 4, Acoustical Society of America.
McAteer, James A., et al. "Ultracal-30 Gypsum Artificial Stones for Research on the Mechinisms of Stone Breakage in Shock Wave Lithotripsy", 2005, pp. 429-434, Springer-Verlag.
Vogel, A., et al. "Mechanisms of Intraocular Photodisruption With Picosecond and Nanosecond Laser Pulses", Lasers in Surgery and Medicine, 1994, pp. 32-43, vol. 15, Wiley-Liss Inc., Lubeck, Germany.
Vogel, A., et al. "Mechanisms of Pulsed Laser Ablation of Biological Tissues", Chemical Reviews, 2003, pp. 577-644, vol. 103, No. 2, American Chemical Society.
Medlight, "Cylindrical light diffuser Model RD-ML", Medlight S.A., Switzerland.
Medlight, "Cylindircal light diffuser Model RD", Medlight S.A., Switzerland.
Mayo, Michael E., "Interaction of Laser Radiation with Urinary Calculi", Cranfield University Defense and Security, PhD Thesis, 2009, Cranfield University.
Vogel, A., et al. "Minimization of Cavitation Effects in Pulsed Laser Ablation Illustrated on Laser Angioplasty", Applied Physics, 1996, pp. 173-182, vol. 62, Springer-Verlag.
Mirshekari, G., et al. "Microscale Shock Tube", Journal of Microelectromechanical Systems, 2012, pp. 739-747, vol. 21, No. 3, IEEE.
"Polymicro Sculpted Silica Fiber Tips", Molex, 2013, Molex.
Zhou, J., et al. "Optical Fiber Tips and Their Applications", Polymicro Technologies a Subsidiary of Molex, Nov. 2007.
Liang, Xiao-Xuan, et al. "Multi-Rate-Equation modeling of the energy spectrum of laser-induced conduction band electrons in water", Optics Express, 2019, vol. 27, No. 4, Optical Society of America.
Nachabe, R., et al. "Diagnosis of breast cancer using diffuse optical spectroscopy from 500 to 1600 nm: comparison of classification methods", Journal of Biomedical Optics, 2011, vol. 16(8), SPIE.
Naugol'Nykh, K. A., et al. "Spark Discharges in Water", Academy of Sciences USSR Institute of Acoustics, 1971, Nauka Publishing Co., Moscow, USSR.
Van Leeuwen, Ton G., et al. "Noncontact Tissue Ablation by Holmium: YSGG Laser Pulses in Blood", Lasers in Surgery and Medicine, 1991, vol. 11, pp. 26-34, Wiley-Liss Inc.
Nyame, Yaw A., et al. "Kidney Stone Models for in Vitro Lithotripsy Research: A Comprehensive Review", Journal of Endourology, Oct. 2015, pp. 1106-1109, vol. 29, No. 10, Mary Ann Liebert Inc., Cleveland, USA.
Ohl, Siew-Wan, et al. "Bubbles with shock waves and ultrasound: a review", Interface Focus, pp. 1-15, vol. 5, The Royal Society Publishing.
Zheng, W., "Optical Lenses Manufactured on Fiber Ends", IEEE, 2015, Splicer Engineering, Duncan SC USA.
Dwyer, P. J., et al. "Optically integrating balloon device for photodynamic therapy", Lasers in Surgery and Medicine, 2000, pp. 58-66, vol. 26, Issue 1, Wiley-Liss Inc., Boston MA USA.
"The New Optiguide DCYL700 Fiber Optic Diffuser Series", Optiguide Fiber Optic Spec Sheet, Pinnacle Biologics, 2014, Pinnacle Biologics, Illinois, USA.
Van Leeuwen, Ton G., et al. "Origin of arterial wall dissections induced by pulsed excimer and mid-infared laser ablation in the pig", JACC, 1992, pp. 1610-1618, vol. 19, No. 7, American College of Cardiology.
Oshita, D., et al. "Characteristic of Cavitation Bubbles and Shock Waves Generated by Pulsed Electric Discharges with Different Voltages", IEEE, 2012, pp. 102-105, Kumamoto, Japan.
Karsch, Karl R., et al. "Percutaneous Coronary Excimer Laser Angioplasty in Patients With Stable and Unstable Angina Pectoris", Circulation, 1990, pp. 1849-1859, vol. 81, No. 6, American Heart Association, Dallas TX, USA.
Murray, A., et al. "Peripheral laser angioplasty with pulsed dye laser and ball tipped optical fibres", The Lancet, 1989, pp. 1471-1474, vol. 2, Issue 8678-8679.
Mohammadzadeh, M., et al. "Photoacoustic Shock Wave Emission and Cavitation from Structured Optical Fiber Tips", Applied Physics Letters, 2016, vol. 108, American Institute of Physics Publishing LLC.
Doukas, A. G., et al. "Physical characteristics and biological effects of laser-induced stress waves", Ultrasound in Medicine and Biology, 1996, pp. 151-164, vol. 22, Issue 2, World Federation for Ultrasound in Medicine and Biology, USA.
Doukas, A. G., et al. "Physical factors involved in stress-wave-induced cell injury: the effect of stress gradient", Ultrasound in Medicine and Biology, 1995, pp. 961-967, vol. 21, Issue 7, Elsevier Science Ltd., USA.
Piedrahita, Francisco S., "Experimental Research Work on a Sub-Millimeter Spark-Gap for Sub Nanosecond Gas Breakdown", Thesis for Universidad Nacional De Colombia, 2012, Bogota, Colombia.
Vogel, A., et al. "Plasma Formation in Water by Picosecond and Nanosecond Nd: YAG Laser Pulses—Part I: Optical Breakdown at

(56) References Cited

OTHER PUBLICATIONS

Threshold and Superthreshold Irradiance", IEEE Journal of Selected Topics in Quantum Electronics, 1996, pp. 847-859, vol. 2, No. 4, IEEE.
Park, Hee K., et al. "Pressure Generation and Measurement in the Rapid Vaporization of Water on a Pulsed-Laser-Heated Surface", Journal of Applied Physics, 1996, pp. 4072-4081, vol. 80, No. 7, American Institute of Physics.
Cummings, Joseph P., et al. "Q-Switched laser ablation of tissue: plume dynamics and the effect of tissue mechanical properties", SPIE, Laser-Tissue Interaction III, 1992, pp. 242-253, vol. 1646.
Lee, Seung H., et al. "Radial-firing optical fiber tip containing conical-shaped air-pocket for biomedical applications", Optics Express, 2015, vol. 23, No. 16, Optical Society of America.
Hui, C., et al. "Research on sound fields generated by laser-induced liquid breakdown", Optica Applicata, 2010, pp. 898-907, vol. XL, No. 4, Xi'an, China.
Riel, Louis-Philippe, et al. "Characterization of Calcified Plaques Retrieved From Occluded Arteries and Comparison with Potential Artificial Analogues", Proceedings of the ASME 2014 International Mechanical Engineering Congress and Exposition, 2014, pp. 1-11, ASME, Canada.
Roberts, Randy M., et al. "The Energy Partition of Underwater Sparks", The Journal of the Acoustical Society of America, 1996, pp. 3465-3475, vol. 99, No. 6, Acoustical Society of America.
Rocha, R., et al. "Fluorescence and Reflectance Spectroscopy for Identification of Atherosclerosis in Human Carotid Arteries Using Principal Components Analysis", Photomedicine and Lsser Surgery, 2008, pp. 329-335, vol. 26, No. 4, Mary Ann Liebert Inc.
Scepanovic, Obrad R., et al. "Multimodal spectroscopy detects features of vulnerable atherosclerotic plaque", Journal of Biomedical Optics, 2011, pp. 1-10, vol. 16, No. 1, SPIE.
Serruys, P. W., et al. "Shaking and Breaking Calcified Plaque Lithoplasty, a Breakthrough in Interventional Armamentarium?", JACC: Cardiovascular Imaging, 2017, pp. 907-911, vol. 10, No. 8, Elsevier.
Vogel, A., et al. "Shock wave emission and cavitation bubble generation by picosecond and nanosecond optical breakdown in water", The Journal of the Acoustical Society of America, 1996, pp. 148-165, vol. 100, No. 1, Acoustical Society of America.
Vogel, A., et al. "Shock-Wave Energy and Acoustic Energy Dissipation After Laser-induced Breakdown", SPIE, 1998, pp. 180-189, vol. 3254, SPIE.
Stelzle, F., et al. "Diffuse Reflectance Spectroscopy for Optical Soft Tissue Differentiation as Remote Feedback Control for Tissue-Specific Laser Surgery", Lasers in Surgery and Medicine, 2010, pp. 319-325, vol. 42, Wiley-Liss Inc.
Stelzle, F., et al. Tissue Discrimination by Uncorrected Autofluorescence Spectra: A Proof-of-Principle Study for Tissue-Specific Laser Surgery, Sensors, 2013, pp. 13717-13731, vol. 13, Basel, Switzerland.
Tagawa, Y., et al. "Structure of laser-induced shock wave in water", Japan Society for the Promotion of Science, 2016.
Shen, Y., et al. "Theoretical and experimental studies of directivity of sound field generated by pulsed laser induced breakdown in liquid water", SPIE, 2013, pp. 8796141-8796148, vol. 8796, SPIE.
Preisack, M., et al. "Ultrafast imaging of tissue ablation by a XeCl excimer laser in saline", Lasers in Surgery and Medicine, 1992, pp. 520-527, vol. 12, Wiley-Liss Inc.
Versluis, M., et al. "How Snapping Shrimp Snap: Through Cavitating Bubbles", Science Mag, 2000, pp. 2114-2117, vol. 289, American Association for the Advancement of Science, Washington DC, USA.
Yan, D., et al. "Study of the Electrical Characteristics, Shock-Wave Pressure Characteristics, and Attenuation Law Based on Pulse Discharge in Water", Shock and Vibration, 2016, pp. 1-11, vol. 2016, Article ID 6412309, Hindawi Publishing Corporation.
Zhang, Q., et al. "Improved Instruments and Methods for the Photographic Study of Spark-Induced Cavitation Bubbles", Water, 2018, pp. 1-12, vol. 10, No. 1683.

"Damage threshold of fiber facets", NKT Photonics, 2012, pp. 1-4, Denmark.
Smith, A., et al. "Bulk and surface laser damage of silica by picosecond and nanosecond pulses at 1064 nm", Applied Optics, 2008, pp. 4812-4832, vol. 47, No. 26, Optical Society of America.
Smith, A., et al. "Deterministic Nanosecond Laser-Induced Breakdown Thresholds in Pure and Yb3 Doped Fused Silica", SPIE, 2007, pp. 6453171-64531712, vol. 6453, SPIE.
Sun, X., et al. "Laser Induced Damage to Large Core Optical Fiber by High Peak Power Laser", Specialty Photonics Division, 2010.
Smith, A., et al. "Nanosecond laser-induced breakdown in pure and Yb3 doped fused silica", SPIE, 2007, vol. 6403, SPIE.
Smith, A., et al. "Optical Damage Limits to Pulse Energy From Fibers", IEEE Journal of Selected Topics in Quantum Electronics, 2009, pp. 153-158, vol. 15, No. 1, IEEE.
Reichel, E., et al. "A Special Irrigation Liquid to Increase the Reliability of Laser-Induced Shockwave Lithotripsy", Lasers in Surgery and Medicine, 1992, pp. 204-209, vol. 12, Wiley-Liss Inc., Graz, Austria.
Reichel, E., et al. "Bifunctional irrigation liquid as an ideal energy converter for laser lithotripsy with nanosecond laser pulses", SPIE Lasers in Urology, Laparoscopy, and General Surgery, 1991, pp. 129-133, vol. 1421, SPIE.
Reichel, E., et al. "Laser-induced Shock Wave Lithotripsy with a Regenerative Energy Converter", Lasers in Medical Science, 1992, pp. 423-425, vol. 7, Bailliere Tindall.
Hardy, L., et al. "Cavitation Bubble Dynamics during Thulium Fiber Laser Lithotripsy", Spie BiOS, 2016, vol. 9689, SPIE.
Deckelbaum, L., "Coronary Laser Angioplasty", Lasers in Surgery and Medicine, 1994, pp. 101-110, vol. 14, Wiley-Liss Inc., Conneticuit, USA.
Shangguan, H., et al. "Effects of Material Properties on Laser-induced Bubble Formation in Absorbing Liquids and on Submerged Targets", Diagnostic and Therapeutic Cardiovascular Interventions VII, SPIE, 1997, pp. 783-791, vol. 2869, SPIE.
Van Leeuwen, T., et al. "Excimer Laser Induced Bubble: Dimensions, Theory, and Implications for Laser Angioplasty", Lasers in Surgery and Medicine, 1996, pp. 381-390, vol. 18, Wiley-Liss Inc., The Netherlands.
Vogel, A., et al. "Shock Wave Emission and Cavitation Bubble Generation by Picosecond and Nanosecond Optical Breakdown in Water", The Journal of Acoustical Society of America, 1996, pp. 148-165, vol. 100, No. 1, The Acoustical Society of America.
Varghese, B., et al. "Influence of absorption induced thermal initiation pathway on irradiance threshold for laser induced breakdown", Biomedical Optics Express, 2015, vol. 6, No. 4, Optical Society of America.
Linz, N., et al. "Wavelength dependence of nanosecond infrared laser-induced breakdown in water: Evidence for multiphoton initiation via an intermediate state", Physical Review, 2015, pp. 134114.1-1341141.10, vol. 91, American Physical Society.
International Search Report and Written Opinion dated Jun. 27, 2018, in PCT Application Serial No. PCT/US2018/027121.
International Search Report and Written Opinion dated Jul. 20, 2018, in PCT Application Serial No. PCT/US2018/027801.
International Search Report and Written Opinion dated Jul. 20, 2018, in PCT Application Serial No. PCT/US2018/027784.
European Search Report, for European Application No. 18185152, mailed Dec. 13, 2018.
International Search Report and Written Opinion dated May 22, 2019, in PCT Application Serial No. PCT/US2019/022009.
International Search Report and Written Opinion dated May 29, 2019, in PCT Application Serial No. PCT/US2019/022016.
International Search Report and Written Opinion dated Jun. 22, 2018, in Application Serial No. NL2019807, issued by the European Patent Office.
Noimark, Sacha, et al., "Carbon-Nanotube-PDMS Composite Coatings on Optical Fibers for All-Optical Ultrasound Imaging", Advanced Functional Materials, 2016, pp. 8390-8396, vol. 26, Wiley-Liss Inc.
Chen, Sung-Liang, "Review of Laser-Generated Ultrasound Transmitters and their Applications to All-Optical Ultrasound Transducers and Imaging", Appl. Sci. 2017, 7, 25.

(56) References Cited

OTHER PUBLICATIONS

Colchester, R., et al. "Laser-Generated ultrasound with optica fibres using functionalised carbon nanotube composite coatings", Appl. Phys. Lett., 2014, vol. 104, 173504, American Institute of Physics.
Poduval, R., et al. "Optical fiber ultrasound transmitter with electrospun carbon nanotube-polymer composite", Appl. Phys. Lett., 2017, vol. 110, 223701, American Institute of Physics.
Tian, J., et al. "Distributed fiber-optic laser-ultrasound generation based on ghost-mode of tilted fiber Bragg gratings", Optics Express, Mar. 2013, pp. 6109-6114, vol. 21, No. 5, Optical Society of America.
Kim, J., et al. "Optical Fiber Laser-Generated-Focused-Ultrasound Transducers for Intravascular Therapies", IEEE, 2017.
Kang, H., et al. "Enhanced photocoagulation with catheter-based diffusing optical device", Journal of Biomedical Optics, 2012, vol. 17, Issue 11, 118001, SPIE.
International Search Report and Written Opinion dated Jan. 3, 2020, in PCT Application Serial No. PCT/US2019/056579.
Communication Pursuant to Article 94(3) EPC, for European Patent Application No. 18185152.8, mailed Jan. 16, 2019.
"Custom Medical Skived Tubing", Duke Extrusion, 2025. https://www.dukeextrusion.com/tubing-options/skived-tubing.

\* cited by examiner

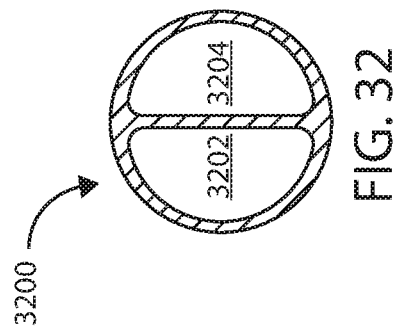
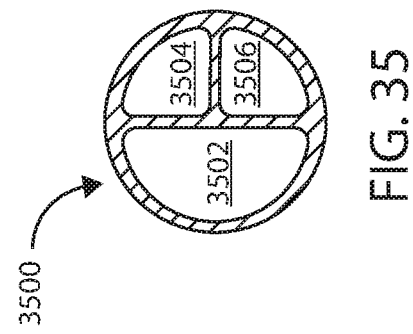
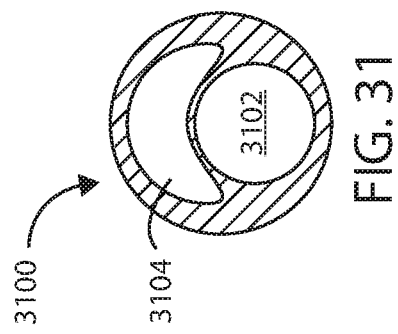
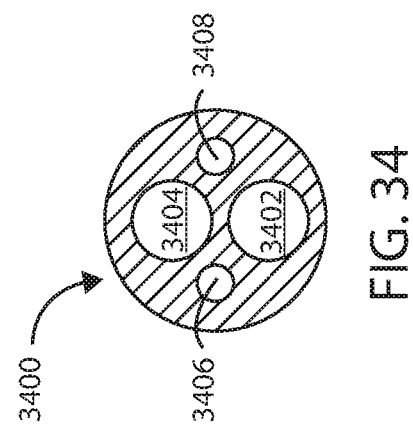
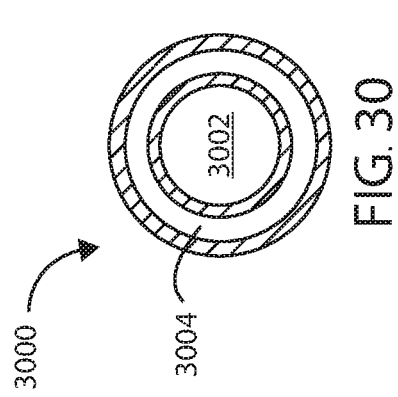
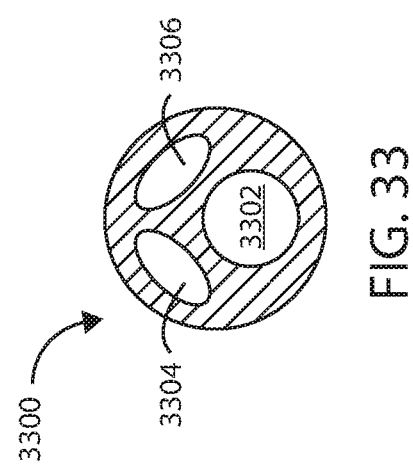

FOCUSING ELEMENT FOR PLASMA SYSTEM TO DISRUPT VASCULAR LESIONS

RELATED APPLICATIONS

This application claims priority on U.S. Provisional Application Ser. No. 62/866,981, filed on Jun. 26, 2019, and entitled "SIDE LIGHT DIRECTION PLASMA SYSTEM TO DISRUPT VASCULAR LESIONS", on U.S. Provisional Application No. 62/867,009, filed on Jun. 26, 2019, entitled, "LIGHT GUIDE PROTECTION STRUCTURES FOR PLASMA SYSTEM TO DISRUPT VASCULAR LESIONS", on U.S. Provisional Application No. 62/867,026, filed on Jun. 26, 2019, entitled, "FORTIFIED BALLOON INFLATION FLUID FOR PLASMA SYSTEM TO DISRUPT VASCULAR LESIONS", and on U.S. Provisional Application No. 62/867,034, filed on Jun. 26, 2019, entitled, "FOCUSING ELEMENT FOR PLASMA SYSTEM TO DISRUPT VASCULAR LESIONS", the contents of which for each application are herein incorporated by reference in their entirety to the extent permitted.

BACKGROUND

Vascular lesions within vessels in the body can be associated with an increased risk for major adverse events, such as myocardial infarction, embolism, deep vein thrombosis, stroke, and the like. Severe vascular lesions can be difficult to treat and achieve patency for a physician in a clinical setting.

Vascular lesions may be treated using interventions such as drug therapy, balloon angioplasty, atherectomy, stent placement, vascular graft bypass, to name a few. Such interventions may not always be ideal or may require subsequent treatment to address the lesion.

SUMMARY

In a first aspect, a catheter system for imparting pressure to induce fractures in a vascular lesion within or adjacent a blood vessel wall is included. The catheter system can include a catheter configured to advance to the vascular lesion located within or adjacent a blood vessel. The catheter can include an elongate shaft, and a balloon coupled to the elongate shaft, where the balloon can include a balloon wall and can be configured to expand from a collapsed configuration suitable for advancing the catheter through a patient's vasculature to a first expanded configuration suitable for anchoring the catheter in position relative to a vascular lesion. The catheter can include a first light guide disposed along the elongate shaft and within a balloon, where the first light guide can be configured to be placed in optical communication with a light source and a balloon fluid. The catheter can include at least a first focusing element located at a distal portion of the first light guide and in optical communication with the light source. The first focusing element can be configured to direct light from within the first light guide to a first location at a first distance away from the distal portion of the first light guide to initiate plasma formation in the balloon fluid away from the distal portion and to cause rapid bubble formation, thereby imparting pressure waves upon the vascular lesion.

In a second aspect, in addition to one or more of the preceding or following aspects, or in the alternative to some aspects, the catheter system further can include a second focusing element located at a distal portion of the first light guide, the second focusing element configured to direct light from within the first light guide to a second location at a second distance away from the distal portion of the first light guide to initiate plasma formation in the balloon fluid away from the distal portion and to cause rapid bubble formation, thereby imparting pressure waves upon the vascular lesion.

In a third aspect, in addition to one or more of the preceding or following aspects, or in the alternative to some aspects, where the first focusing element includes a convex lens, a convex mirror, or a gradient-index (GRIN) lens.

In a fourth aspect, in addition to one or more of the preceding or following aspects, or in the alternative to some aspects, where the first focusing element is located at a distal tip of the first light guide.

In a fifth aspect, in addition to one or more of the preceding or following aspects, or in the alternative to some aspects, where the first location is spaced away from the distal tip and is centered on a longitudinal axis of the first light guide.

In a sixth aspect, in addition to one or more of the preceding or following aspects, or in the alternative to some aspects, where the first distance is at least 1 µm and at most 3 mm away from the distal tip of the first light guide.

In a seventh aspect, in addition to one or more of the preceding or following aspects, or in the alternative to some aspects, the catheter systems further can include a second light guide coupled to the elongate shaft, where the second light guide is in optical communication with the light source and the balloon fluid. The catheter system can include a focusing element of the second light guide located at a distal portion of the second light guide and in optical communication with the light source, where the focusing element of the second light guide configured to direct light from within the second light guide to a second location at a second distance from the distal portion of the second light guide to initiate plasma formation in the balloon fluid away from the distal portion and to cause rapid bubble formation, thereby imparting pressure waves upon the vascular lesion.

In an eighth aspect, in addition to one or more of the preceding or following aspects, or in the alternative to some aspects, where the first light guide is an optical fiber and the light source is a laser.

In a ninth aspect, in addition to one or more of the preceding or following aspects, or in the alternative to some aspects, where the elongate shaft defines an inflation lumen, and where the inflation lumen is in fluid communication with the balloon at a distal portion of the elongate shaft.

In a tenth aspect, in addition to one or more of the preceding or following aspects, or in the alternative to some aspects, where the first light guide further includes a first diverting feature located at a distal portion of the first light guide and can be configured to direct light from within the first light guide toward the first focusing element and toward the balloon wall, and where the first location is spaced away from a longitudinal axis of the first light guide.

In an eleventh aspect, a catheter system for imparting pressure to induce fractures in a vascular lesion within or adjacent a blood vessel wall is included. The catheter system can include a catheter configured to advance to the vascular lesion located within or adjacent a blood vessel, the catheter can include an elongate shaft, and a balloon coupled to the elongate shaft. The balloon can include a balloon wall and can be configured to expand from a collapsed configuration suitable for advancing the catheter through a patient's vasculature to a first expanded configuration suitable for anchoring the catheter in position relative to a vascular lesion. The catheter can include a first light guide disposed along the elongate shaft and within a balloon. The first light guide can be configured to be placed in optical communication with a light source and a balloon fluid. The first light guide can include a first diverting feature located at a distal portion of the first light guide and can be configured to direct light from within the first light guide toward a first focusing element. The first light guide can include a first focusing element located at a distal portion of the first light guide, where the first diverting feature can be in optical communication with the first focusing element. The first focusing element can be configured to direct light from within the first light guide to a first location at a first distance from the distal portion of the first light guide and toward the balloon wall to initiate plasma formation in the balloon fluid away from the distal portion and to cause rapid bubble formation, thereby imparting pressure waves upon the vascular lesion. The first location can be spaced away from a longitudinal axis of the first light guide.

In a twelfth aspect, in addition to one or more of the preceding or following aspects, or in the alternative to some aspects, where the first light guide has a longitudinal axis, and where the first focusing element is configured to direct light from within the first light guide to a location in the balloon fluid spaced away from the longitudinal axis.

In a thirteenth aspect, in addition to one or more of the preceding or following aspects, or in the alternative to some aspects, where the first light guide further includes a second diverting feature located at a distal portion of the first light guide and configured to direct light from within the first light guide toward a second focusing element.

In a fourteenth aspect, in addition to one or more of the preceding or following aspects, or in the alternative to some aspects, where the catheter system further can include a second light guide coupled to the elongate shaft, where the second light guide is in optical communication with the light source and the balloon fluid.

In a fifteenth aspect, in addition to one or more of the preceding or following aspects, or in the alternative to some aspects, where the first diverting feature is a fiber diffuser.

In a sixteenth aspect, in addition to one or more of the preceding or following aspects, or in the alternative to some aspects, where the first focusing element includes a convex lens, a convex mirror, or a gradient-index (GRIN) lens.

In a seventeenth aspect, in addition to one or more of the preceding or following aspects, or in the alternative to some aspects, where the first focusing element includes a GRIN lens.

In an eighteenth aspect, in addition to one or more of the preceding or following aspects, or in the alternative to some aspects, where the GRIN lens is adhered to a side surface portion of the first light guide.

In a nineteenth aspect, a method for generating pressure waves to induce fractures in a vascular lesion within or adjacent a vessel wall of a blood vessel is included. The method can include advancing a catheter to a vascular lesion within the blood vessel. The catheter can include an elongate shaft and a balloon coupled to the elongate shaft. The catheter can include at least a first light guide disposed along the elongate shaft within the balloon, where the first light guide configured to be placed in optical communication with a light source and a balloon fluid. The first light guide can include a first focusing element located at a distal portion of the first light guide. The method can include expanding the balloon from a collapsed configuration suitable for advancing the catheter through a patient's vasculature to a first expanded configuration suitable for anchoring the catheter in position relative to a vascular lesion. The method can include, after expanding the balloon, activating a light source in optical communication with the first light guide to direct light from within the first light guide to a first location at a first distance away from the distal portion of the first light guide to initiate plasma formation in the balloon fluid away from the distal portion and to cause rapid bubble formation, thereby imparting pressure waves upon the vascular lesion. The first location can be spaced away from the distal tip and can be centered on a longitudinal axis of the first light guide.

In a twentieth aspect, in addition to one or more of the preceding or following aspects, or in the alternative to some aspects, the method further can include, after activating the light source, further expanding the balloon from the first expanded configuration to a second further expanded configuration.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE DRAWINGS

The novel features of this invention, as well as the invention itself, both as to its structure and its operation, will be best understood from the accompanying drawings, taken in conjunction with the accompanying description, and in which:

FIG. 30-41 are schematic cross-sectional views of additional embodiments of an elongate shaft of a catheter in accordance with various embodiments herein While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DESCRIPTION

Treatment of vascular lesions can reduce major adverse events or death in affected subjects. A major adverse event is one that can occur anywhere within the body due to the presence of a vascular lesion. Major adverse events can include, but are not limited to major adverse cardiac events, major adverse events in the peripheral or central vasculature, major adverse events in the brain, major adverse events in the musculature, or major adverse events in any of the internal organs.

The systems and methods disclosed herein describe the use of a catheter systems including any number of light guides for generating pressure waves within a balloon for disrupting intervascular lesions at a treatment site. The catheter systems herein utilize light energy to generate a plasma at or near a light guide disposed in a balloon located at a treatment site, where the treatment site can include a vascular lesion such as a calcified vascular lesion or a fibrous vascular lesion. The plasma formation can initiate a shockwave and can initiate the rapid formation of one or more bubbles that can rapidly expand to a maximum size and then dissipate through a cavitation event that can launch a shockwave upon collapse. The rapid expansion of the plasma-induced bubbles can generate one or more pressure waves within a balloon fluid and thereby impart pressure waves upon the treatment site. The pressure waves can transfer mechanical energy through an incompressible balloon fluid to a treatment site to impart a fracture force on an intravascular lesion. Without wishing to be bound by any particular theory, it is believed that the rapid change in balloon fluid momentum upon a balloon wall that is in contact with an intravascular lesion is transferred to the intravascular lesion to induce fractures to the lesion.

The catheter systems herein are configured to impart pressure to induce fractures in a vascular lesion within or adjacent a blood vessel wall. The catheter systems can include a catheter configured to advance to the vascular lesion located within or adjacent a blood vessel, where the catheters include an elongate shaft. The catheters also include one or more light guides disposed along the elongate shaft and within a balloon. Each light guide can be configured to be placed in optical communication with a light source.

Figure 1:
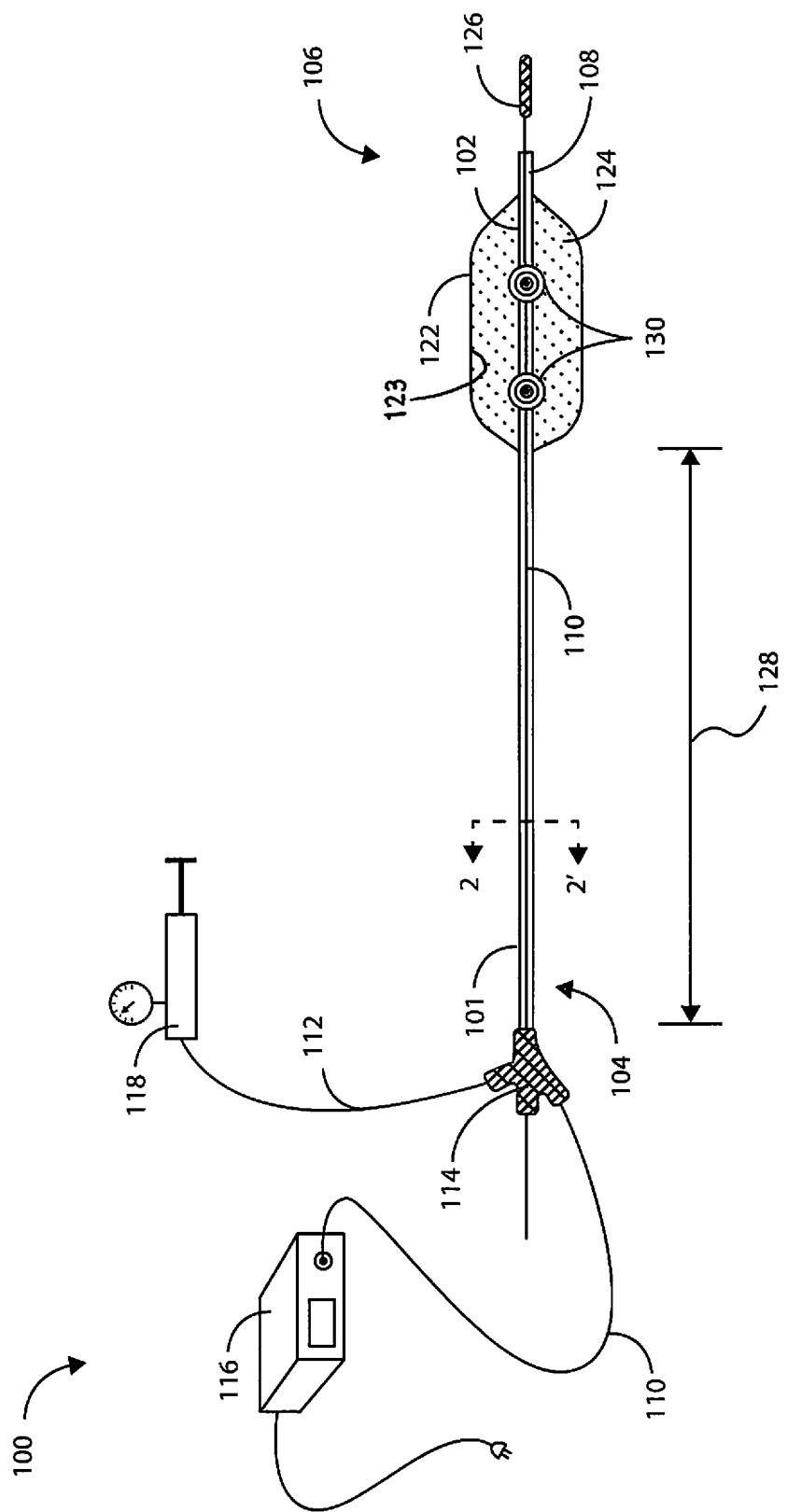
FIG. 1 is a schematic cross-sectional view of a catheter in accordance with various embodiments herein.

Light Directed Toward a Balloon Wall (FIG. 1)

The light guides herein can be configured to include one or more diverting features configured to direct light to exit from the light guide toward a side surface portion of the light guide and toward the balloon wall. The diverting features direct light to exit in a direction away from the axis of the light guide, or in an off-axis direction. The light guides can each include one or more light windows disposed along the longitudinal or radial surfaces of each light guide and in optical communication with a diverting feature. The light windows can include a portion of the light guide that allows light to exit the light guide from within the light guide, such as a portion of the light guide lacking a cladding material on or about the light guide. The balloons herein can be coupled to the elongate shaft and can be inflated with a balloon fluid.

The balloons herein can include a balloon wall and can be configured to expand from a collapsed configuration suitable for advancing the catheter through a patient's vasculature to a first expanded configuration suitable for anchoring the catheter in position relative to a treatment site. The light source can be configured to provide sub-millisecond pulses of a light from the light source to one or more light windows, and thereby initiate plasma formation in a balloon fluid at or near the light windows to cause rapid bubble formation and to impart pressure waves upon the treatment site.

As used herein, the terms "treatment site", "intravascular lesion" and "vascular lesion" are used interchangeably unless otherwise noted.

It is appreciated that the catheter systems herein can include many different forms. Referring now to FIG. 1, a schematic cross-sectional view is shown of a catheter in accordance with various embodiments herein. Catheter system 100 is suitable for imparting pressure to induce fractures in a vascular lesion within or adjacent a vessel wall of a blood vessel. Catheter system 100 includes a catheter 101. Catheter 101 can be configured to advance to a treatment site within or adjacent a blood vessel. In some embodiments, the treatment site includes a vascular lesion such as a calcified vascular lesion. In other embodiments, the treatment site includes a vascular lesion such as a fibrous vascular lesion.

The catheter 101 can include an elongate shaft 102 and a balloon 122 coupled to the elongate shaft 102. The elongate shaft 102 can extend from a proximal portion 104 to a distal portion 106, and can also include a lumen 108. The catheter 101 can include a guidewire 126. In some embodiments, the catheter 101 includes a guidewire lumen. The elongate shaft 102 can further include an inflation lumen. Various lumen configurations and their uses will be discussed in more detail below. In some embodiments, the catheter 101 can have a distal end opening and can accommodate and be tracked over guidewire 126 to a treatment site. In some embodiments, the catheter 101 does not include a guidewire lumen. In embodiments where the elongate shaft 102 does not include a lumen to be accessed by a caregiver, the elongate shaft 102 can be configured to allow the catheter to be steered through a patient's vasculature.

The elongate shaft 102 of catheter 101 can be coupled to a first light guide 110 and a second light guide (not shown) in optical communication with a light source 116. The first light guide and second light guide can be disposed along the elongate shaft and within the balloon. It is appreciated that the second light guide of catheter 101 can be offset from first light guide 110 by 180 degrees about the elongate shaft 102 such that it is obstructed from view by first light guide 110 in FIG. 1. In some embodiments, the first light guide 110 and second light guide can be optical fibers and the light source can be a laser. The light source 116 can be in optical communication with the first light guide 110 and second light guide at a proximal portion 104 of the elongate shaft 102. In some embodiments, the elongate shaft can be coupled to multiple light guides such as a third light guide and a fourth light guide. The light source 116 can be in optical communication with the third light guide and the fourth light guide at a proximal portion 104 of the elongate shaft 102. In some embodiments, the elongate shaft can be coupled to more than a fourth light guide.

The balloon 122 of catheter 101 can include a balloon wall 123 and can expand from a collapsed configuration suitable for advancing the catheter through a patient's vasculature to a first expanded configuration suitable for anchoring the catheter in position relative to a treatment site. Expansion of the balloons herein to various expanded configurations will be discussed in more detail below. The light source 116 of catheter system 100 can be configured to provide sub-millisecond pulses of light from the light source through the at least first light window and second light window, thereby inducing plasma formation in a balloon fluid, causing rapid bubble formation, and imparting pressure waves upon the treatment site. Exemplary plasma-induced bubbles are shown as bubbles 130 in FIG. 1. In some embodiments, the balloon fluid can be a liquid. Suitable balloon fluids for use herein will be discussed in more detail below. In an embodiment, a catheter herein can include a single light guide. The single light guide can include one or more light windows to direct light out the side of the light guide and toward the balloon wall 123. In one embodiment, the single light guide can include two light windows that can direct light toward the balloon wall 123 in unison.

The sub-millisecond pulses of light can be delivered to a treatment site at a frequency of from at least 1 hertz (Hz) to 5000 Hz. In some embodiments, the sub-millisecond pulses of light can be delivered to a treatment site at a frequency from at least 30 Hz to 1000 Hz. In other embodiments, the sub-millisecond pulses of light can be delivered to a treatment site at a frequency from at least 10 Hz to 100 Hz. In yet other embodiments, the sub-millisecond pulses of light can be delivered to a treatment site at a frequency from at least 1 Hz to 30 Hz. In some embodiments, the sub-millisecond pulses of light can be delivered to a treatment site at a frequency that can be greater than or equal to 1 Hz, 2 Hz, 3 Hz, 4 Hz, 5 Hz, 6 Hz, 7 Hz, 8 Hz, or 9 Hz, 10 Hz, 20 Hz, 30 Hz, 40 Hz, 50 Hz, 60 Hz, 70 Hz, 80 Hz, 90 Hz, 100 Hz, 200 Hz, 300 Hz, 400 Hz, 500 Hz, 600 Hz, 700 Hz, 800 Hz, 900 Hz, 1000 Hz, 1250 Hz, 1500 Hz, 1750 Hz, 2000 Hz, 2250 Hz, 2500 Hz, 2750 Hz, 3000 Hz, 3250 Hz, 3500 Hz, 3750 Hz, 4000 Hz, 4250 Hz, 4500 Hz, 4750 Hz, or 5000 Hz or can be an amount falling within a range between any of the foregoing.

It is appreciated that the catheters herein can include any number of light guides in optical communication with the light source 116 at the proximal portion 104 and a balloon fluid 124 within balloon 122 at the distal portion 106. For example, in some embodiments, the catheters herein can include from one light guide to five light guides. In other embodiments, the catheters herein can include from five light guides to fifteen light guides. In yet other embodiments, the catheters herein can include from ten light guides to thirty light guides. The catheters herein can include one, two, three, four, five, six, seven, eight, nine, or ten light guides. The catheters can include 11, 12, 13, 14, 15, 16, 17, 18, 19, 20, 21, 22, 23, 24, 25, 26, 27, 28, 29, or 30 light guides. It is appreciated that catheters herein can include any number of light guides that can fall within a range, wherein any of the forgoing numbers can serve as the lower or upper bound of the range, provided that the lower bound of the range is a value less than the upper bound of the range. In some embodiments, the catheters herein can include more than 30 light guides. The catheter 101 can further include a manifold 114 at the proximal portion 104 that include one or more proximal end openings that can accommodate one or more light guides, such as first light guide 110, a guidewire 126, and/or an inflation conduit 112. The catheter system 100 can include an inflator 118 configured to provide inflation of the balloon 122. Suitable balloon inflation pressures for balloon 122 will be described in more detail elsewhere herein.

Catheter 101 can include a longitudinal length 128. The catheters herein will have a longitudinal axis along the elongate shaft and short axis about its circumference. The length of the catheters herein can include those having a length of from 50 cm to 175 cm. In some embodiments, the length of the catheters herein can include those having a length of from 100-160 cm. In some embodiments, the length of the catheters herein can include those having a length of 50 cm, 60 cm, 70 cm, 80 cm, 90 cm, 100 cm, 110 cm, 120 cm, 125 cm, 130 cm, 140 cm, 150 cm, 160 cm, 170 cm, or 175 cm. It is appreciated that the catheters herein can have a usable length that can fall within a range, wherein any of the forgoing lengths can serve as the lower or upper bound of the range, provided that the lower bound of the range is a value less than the upper bound of the range.

Figure 2:
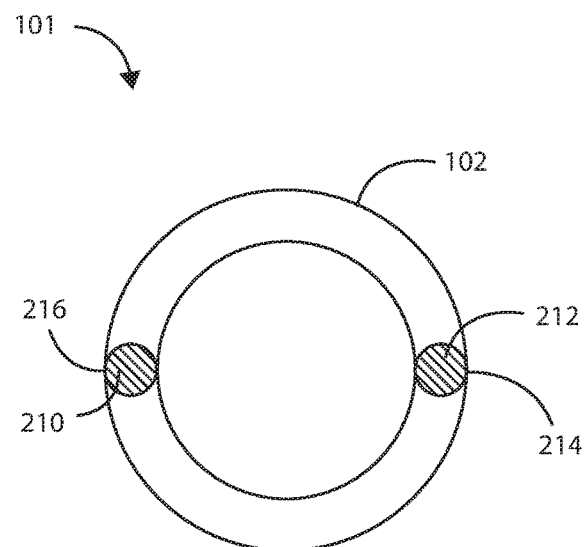
FIG. 2 is a schematic cross-sectional view of an elongate shaft and multiple light guides of a catheter along line 2-2' in FIG. 1 in accordance with various embodiments herein.

Examples of the catheters in accordance with the various embodiments herein include those having multiple light guides disposed about the elongate shaft at different positions around the circumference, as shown in FIGS. 2-5. Referring now to FIG. 2, a schematic cross-sectional view of a catheter 101 of FIG. 1 along line 2-2' in FIG. 1 is shown in accordance with various embodiments herein. Catheter 101 includes an elongate shaft 102, a first light guide 210 and a second light guide 212 separated by about 180 degrees around the circumference. The first light guide 210 includes a side surface portion 216 that can include any surface portion about the circumference of the first light guide. The second light guide 212 includes a side surface portion 214 that can include any surface portion about the circumference of the second light guide. In some examples, the side surface portion 214 spans a portion of the circumference of the light guides herein, such that it is less than 360 degrees around the circumference of the light guides, e.g. less than a fully cylindrical side surface portion 214. In other examples, the side surface portion 214 can span the entire circumference (a full 360 degrees) of the light guides herein such that it is cylindrical. It is appreciated that any light guide described herein can include a side surface portion about a portion or a full circumference of the light guide.

Figure 3:
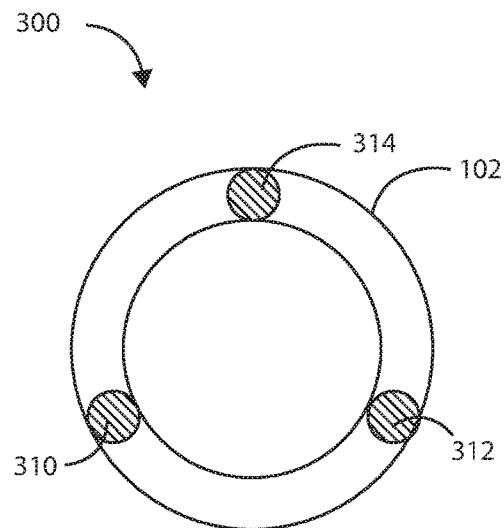
FIGS. 3-5 are schematic cross-sectional views of additional configurations for an elongate shaft and multiple light guides of a catheter along line 2-2' in FIG. 1 in accordance with various embodiments herein.
Figure 4:
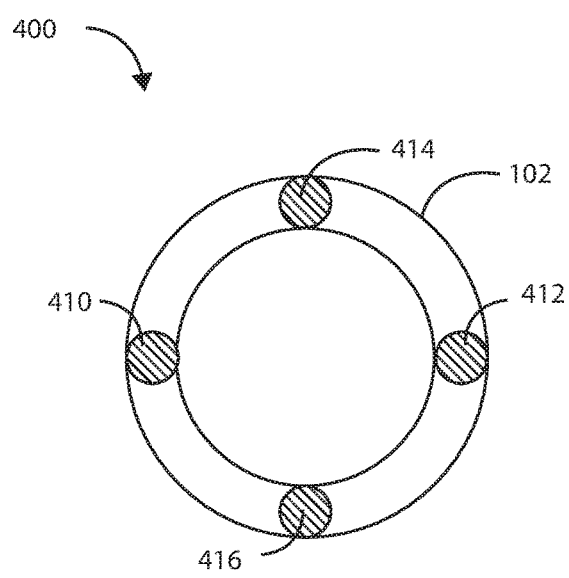
Figure 5:
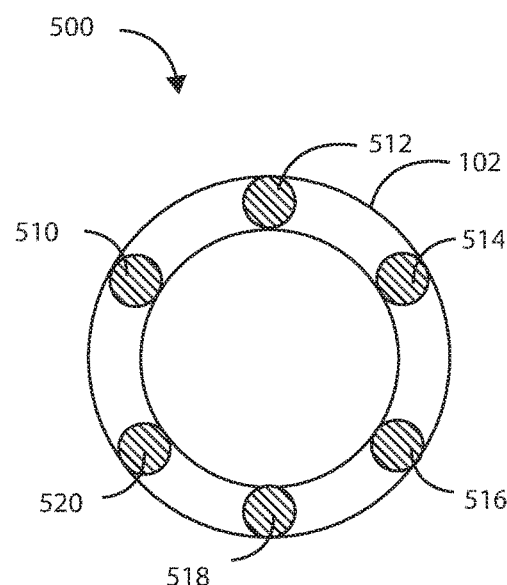

Referring now to FIGS. 3-5, schematic cross-sectional views of additional configurations for catheters having multiple light guides are shown in accordance with various embodiments herein. The configuration of catheter 300 in FIG. 3 includes an elongate shaft 102, a first light guide 310, a second light guide 312, and a third light guide 314 separated by about 120 degrees around the circumference. The configuration of catheter 400 in FIG. 4 includes an elongate shaft 102, a first light guide 410, a second light guide 412, a third light guide 414, and a fourth light guide 416 separated by about 90 degrees around the circumference. The configuration of catheter 500 shown in FIG. 5 includes an elongate shaft 102, a first light guide 510, a second light guide 512, a third light guide 514, a fourth light guide 516, a fifth light guide 518, and a sixth light guide 520 separated by about 60 degrees around the circumference. It is appreciated that more than six light guides can be used in the embodiments herein. It will be further appreciated that the light guides can be disposed uniformly or nonuniformly about the elongate shaft.

The light guides described herein can further include one or more diverting features (not shown in FIG. 1) within the light guide to direct light toward a side surface portion of the distal portion of the light guide and toward the balloon wall 123. A diverting feature can include any feature of the system herein that diverts light from the light guide away from its axial path toward a side surface portion of the light guide. It is appreciated that a light guide, such as first light guide 110 of FIG. 1, can include a first diverting feature configured to direct light to exit from the first light guide 110 toward a side surface portion of the distal portion 106 of the first light guide 110 and toward the balloon wall 123. The first light guide 110 can further define at least a first light window (not shown in FIG. 1) disposed along the first light guide and in optical communication with the first fiber diffuser. A catheter having a second light guide can include a second diverting feature within the second light guide that is configured to direct light to exit from the second light guide toward a side surface portion of the distal portion of the second light guide and toward the balloon wall. The second light guide can further define at least a second light window disposed along the second light guide and in optical communication with the second fiber diffuser.

In some embodiments herein, the light guides can include multiple diverting features. By way of example, each light guide herein can include a first diverting feature, a second diverting feature, a third diverting feature or a fourth diverting feature. In other embodiments, each light guide can include more than four diverting features. The diverting features can be configured to direct light to exit a light guide at a side surface portion thereof toward the balloon wall. In some examples, the diverting feature directs light toward the balloon surface closest to the diverting feature, so that the light does not cross the longitudinal axis of the catheter on its path to the balloon surface. It is appreciated that the diverting features can be in optical communication with corresponding light window.

The diverting features herein can be configured to direct light in the light guide toward a side surface portion of the distal portion, where the side surface portion is in optical communication with a light window. It is appreciated that the light guides herein can each include multiple diverting features and multiple light windows. Examples of the diverting features suitable for use herein include a reflecting element, a refracting element, and a fiber diffuser, and will be discussed in more detail below. In some embodiments, the diverting feature can be a reflecting element. In some embodiments, the diverting feature can be a refracting element. In some embodiments, the diverting feature can be a fiber diffuser. Diverting features will be discussed in more detail below and in reference to FIGS. 6-9.

Catheter Embodiments (FIGS. 6-9

Figure 6:
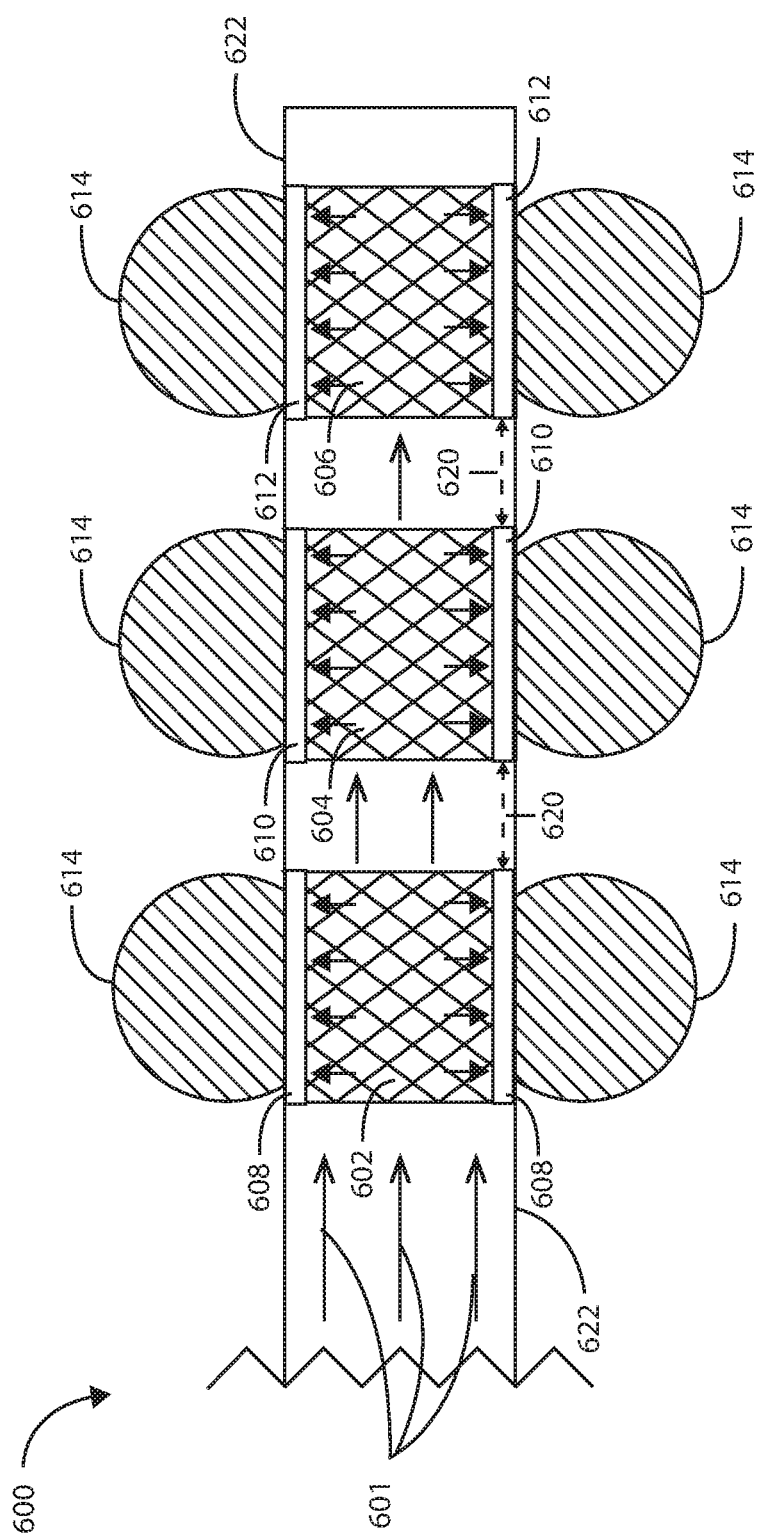
FIG. 6 is a schematic cross-sectional view of a light guide in accordance with various embodiments herein.

In some embodiments, the diverting features within the catheters herein can be included within the light guide at one or more regions of the distal portion. Referring now to FIG. 6 a schematic cross-sectional view of light guide 600 is shown in accordance with various embodiments herein. Light guide 600 includes a plurality of diverting features, such as fiber diffusers including first, second, and third fiber diffusers 602, 604, and 606, respectively, positioned along the elongate shaft of the distal portion of the light guide 600. Each fiber diffuser directs light 601 from the light guide 600 to exit the light guide 600 at a side surface portion 622 thereof. Any side surface portion of the light guide 600 can be in optical communication with one or more light windows, such that the fiber diffusers and the light windows are in optical communication with one another.

By way of example, light guide 600 includes a plurality of light windows including first, second, and third light windows 608, 610, and 612, respectively, positioned along the elongate shaft of the light guide 600. The first, second, and third light windows 608, 610, and 612, respectively, can be in optical communication with the first, second, and third fiber diffusers 602, 604, and 606, respectively, at a side surface portion 622 of light guide 600. Light 601 within each of the first, second, and third fiber diffusers 602, 604, and 606 is directed to exit the light guide 600 at a side surface portion 622 and out the light guides via the first, second, and third light windows 608, 610, and 612, respectively. The light windows 608, 610, and 612 of light guide 600 can be axially spaced apart with at least one intervening non-emitting portion 620 of the light guide 600 disposed between the plurality of light windows. The side surface portion 622 of the light guide 600 can be a cylindrical side surface portion.

The light can exit the light windows to provide sub-millisecond pulses of light from the light source through the at least the first, second, and third light windows 608, 610, and 612, thereby inducing plasma formation in a balloon fluid, causing rapid bubble formation, and imparting pressure waves upon the treatment site. Plasma and bubble formation is depicted in FIG. 6 as bubbles 614 in proximity to the light windows 608, 610, and 612. It is appreciated that bubbles 614 can form around the entire circumferences of the light guide within a volume of the balloon fluid at or adjacent to the light windows 608, 610, and 612.

The fiber diffusers and light windows shown in FIG. 6 include those having a cylindrical shape. By way of example, the fiber diffusers 602, 604, and 606 are configured to span the entire circumference (360 degrees) of light guide 600, and as such, the fiber diffusers 602, 604, and 606 are cylindrical fiber diffusers. The light windows 608, 610, and 612 are configured to span the entire circumference of light guide 600, and as such, light windows 608, 610, and 612 are cylindrical plasma generators. It is appreciated that the cylindrical fiber diffusers 602, 604, and 606 and cylindrical light windows 608, 610, and 612 can generate a plasma within a volume of the balloon fluid at or adjacent to each of the light windows 608, 610, and 612, and thus induce bubble formation and collapse, about the circumference of the light guide 600.

It is appreciated that multiple light guides, each having one or more diverting features, such as fiber diffusers, and one or more light windows can be used with the catheters herein. In some embodiments, the catheters can include a first light guide, a second light guide, a third light guide, and a fourth light guide. In other embodiments, the catheters can include more than four light guides. In an embodiment having four light guides, the distal portion of a first light guide can include a plurality of light windows including a first light window, and a plurality of fiber diffusers including a first fiber diffuser. The distal portion of a second light guide can include a plurality of light windows including a second light window, and a plurality of fiber diffusers including the second fiber diffuser. The distal portion of a third light guide can include a plurality of light windows including a third light window, and a plurality of fiber diffusers including a third fiber diffuser. The distal portion of a fourth light guide can include a plurality of light windows including a fourth light window, and a plurality of fiber diffusers including the fourth fiber diffuser. Each fiber diffuser can direct light from each light guide to exit the light guide at a side surface portion of the light guide toward the balloon wall.

The plurality of light windows can be spaced apart along the longitudinal axis of the light guides or radially along the short axis about the circumference of the light guides. In some embodiments, the plurality of light windows can be radially spaced apart with at least one intervening non-emitting portion of the light guide disposed between each of the plurality of light windows. In some embodiments, the plurality of light windows can be longitudinally spaced apart with at least one intervening non-emitting portion of the light guide disposed between each of the plurality of light windows. In yet other embodiments, the light window can span the length of the vascular lesion to be treated.

Figure 7:
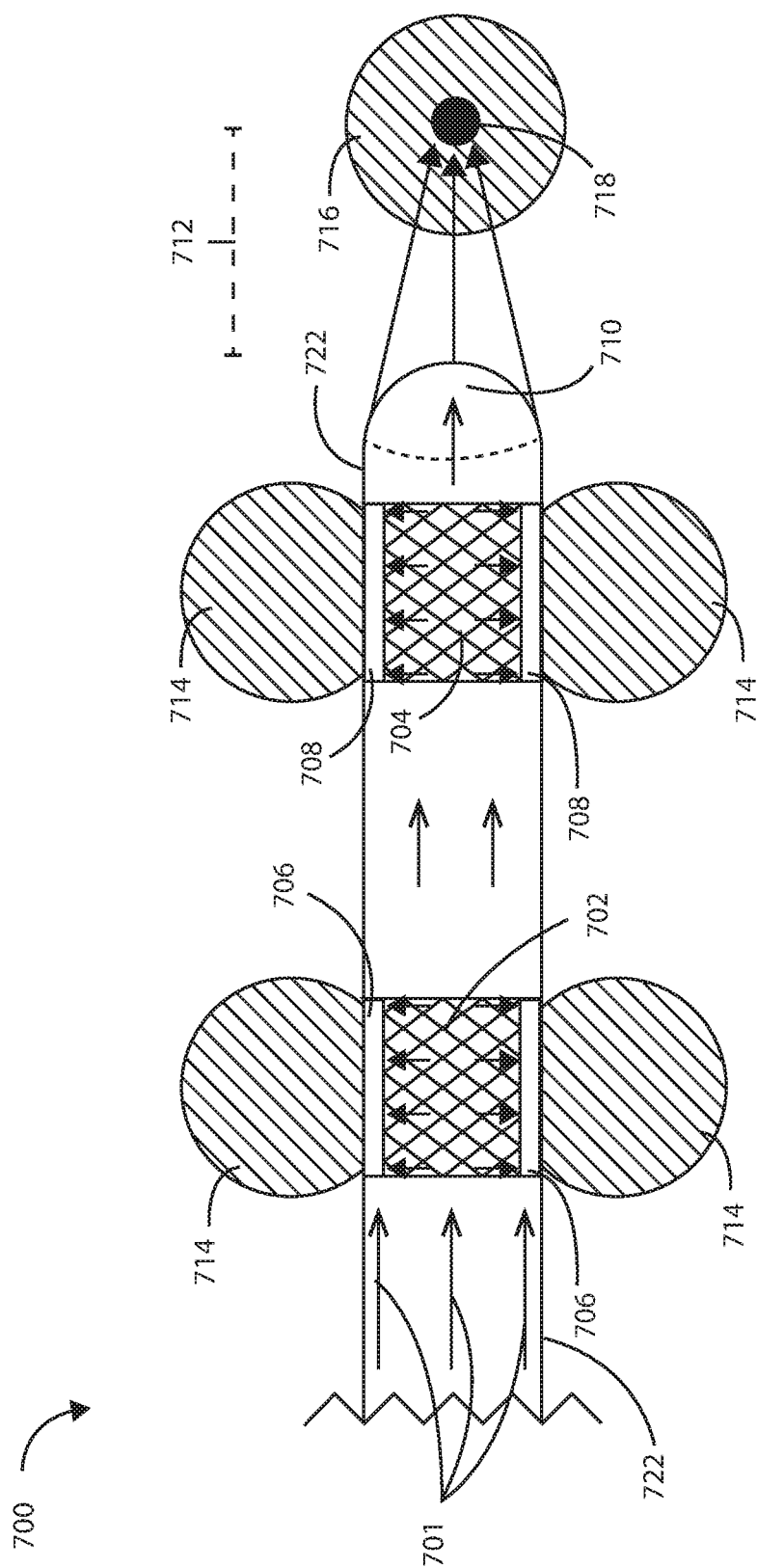
FIG. 7 is a schematic cross-sectional view of a light guide in accordance with various embodiments herein.

In some embodiments, the catheters herein can include diverting features, such as fiber diffusers, in combination with one or more focusing elements included within the light guide at one or more regions of the distal portion. Referring now to FIG. 7 a schematic cross-sectional view of light guide 700 is shown in accordance with various embodiments herein. Light guide 700 includes a plurality of fiber diffusers including a first fiber diffuser 702 and a second fiber diffuser 704 positioned along the longitudinal axis of the distal portion of the light guide 700. Each fiber diffuser directs light 701 from the light guide 700 to exit the light guide 700 at a side surface portion 722 thereof. The side surface portion 722 of the light guide 700 can be a cylindrical side surface portion.

The first fiber diffuser 702 can be in optical communication with a first light window 706, and the second fiber diffuser 704 can be in optical communication with a second light window 708. The light guide 700 can further include a refracting element 710 configured to focus the light 701 away from the distal tip of the light guide 700 such that the induced plasma formation occurs at a distance 712 away from the distal tip of the light guide 700 and within the balloon fluid, causing rapid bubble formation and imparting pressure waves at a treatment site. The light 701 within light guide 700 can exit the first light window 706 and the second light window 708 to deliver sub-millisecond pulses of light from the light source thereby inducing plasma formation in a volume of balloon fluid at or near the first light window 706 and second light window 708, causing rapid bubble formation, and imparting pressure waves upon the treatment site. Plasma and bubble formation is depicted in FIG. 7 as bubbles 714 in proximity to the light windows 706 and 708.

The fiber diffusers and light windows shown in FIG. 7 include those having a cylindrical shape. By way of example, the fiber diffusers 702 and 704 are configured to span the entire circumference (360 degrees) of light guide 700, and as such, the fiber diffusers 702 and 704 are therefore cylindrical fiber diffusers. The light windows 706 and 708 can be configured to span the entire circumference (360 degrees) of light guide 700, and as such, light windows 706 and 708 would be cylindrical plasma generators. It is appreciated that the cylindrical fiber diffusers 702 and 704 and cylindrical light windows 706 and 708 can generate plasma, and thus bubble formation, about the circumference, or a portion of the circumference, of the light guide 700.

The light guide 700 shown in FIG. 7 also includes a diverting feature, such as a refracting element 710 having a convex surface configured to refract the light 701 a distance 712 away from the distal portion of the light guide 700 and to a first location 718. In some embodiments, the first location 718 is spaced away from the distal tip and is centered on a longitudinal axis of the first light guide. In other embodiments, the first location 718 is spaced away from the longitudinal axis of the first light guide, or off of the longitudinal axis. The diverting feature suitable for focusing light away from the tip of the light guides herein can include, but are not to be limited to, those having a convex surface, a gradient-index (GRIN) lens, and a mirror focus lens. Focused plasma formation is depicted in FIG. 7 as focal bubble 716 at a distance 712 from the distal portion of the light guide 700.

Figure 8:
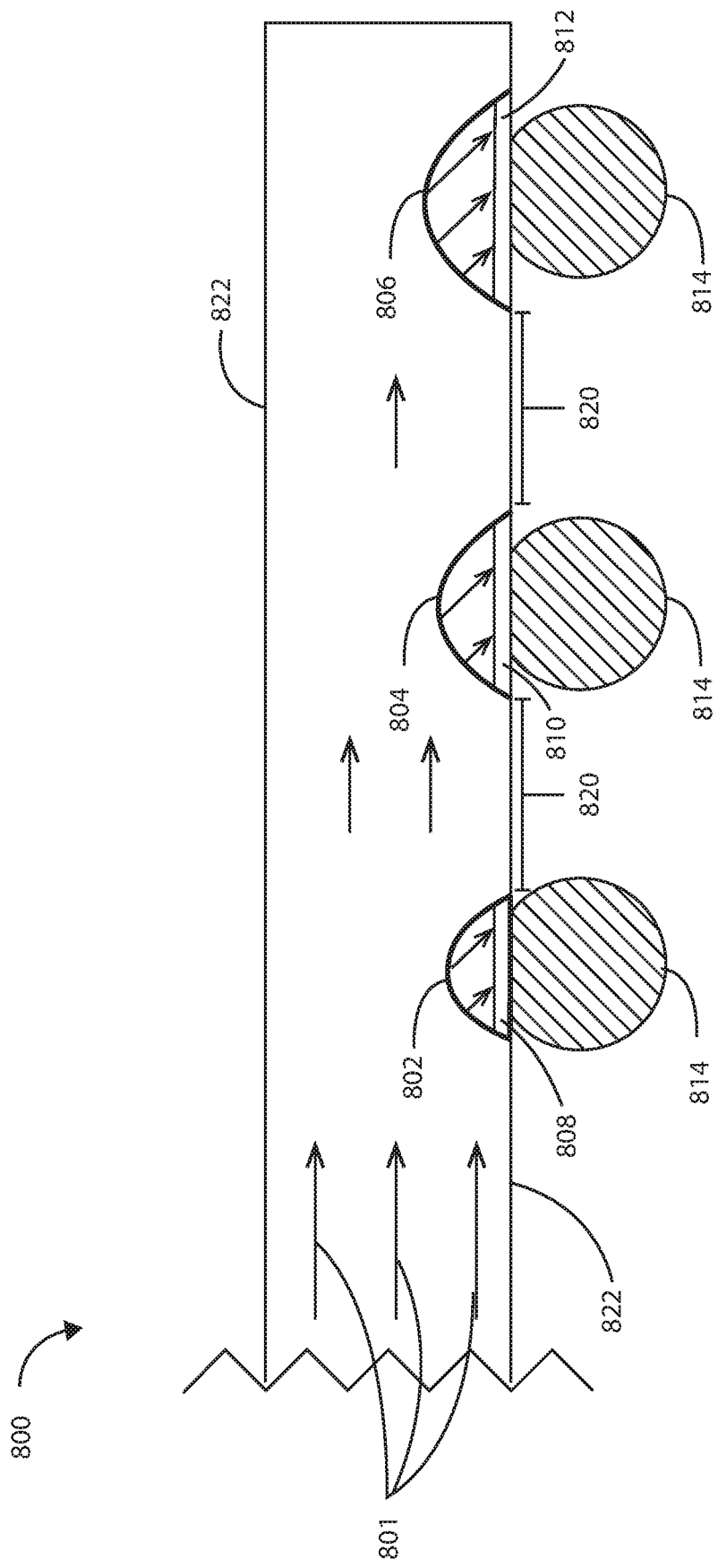
FIG. 8 is a schematic cross-sectional view of a light guide in accordance with various embodiments herein.

The light guides herein can include one or more diverting features disposed on one side portion of the distal portion to provide multiple selected regions within the light guide for the generation of pressure waves. A diverting feature can be included as a part of the light guide that diverts light away from its axial path through the light guide and to a side surface portion and toward a vessel wall. Referring now to FIG. 8 a schematic cross-sectional view of light guide 800 is shown in accordance with various embodiments herein. Light guide 800 includes a plurality of diverting features including a first, second, and third diverting features 802, 804, and 806 positioned along a portion of the elongate shaft of the distal portion of the light guide 800. Each diverting feature directs light 801 from the light guide 800 to exit the light guide 800 at a side surface portion 822 thereof. The side surface portion 822 of the light guide 800 can be in optical communication with one or more diverting features and one or more light windows, such that the diverting features and one or more light windows are in optical communication with one another.

By way of example, light guide 800 includes a plurality of light windows including a first, second, and third light windows 808, 810, and 812 positioned along the elongate shaft of the light guide 800. The first, second, and third light windows 808, 810, and 812 can be in optical communication with the first, second, and third diverting features 802, 804, and 806, respectively, at a side surface portion 822 of light guide 800. Light within each of the first, second, and third diverting features 802, 804, and 806 is directed to exit the light guide 800 at a side surface portion 822 and pass through first, second, and third light windows 808, 810, and 812, respectively. The light can exit the light windows to provide sub-millisecond pulses of light from the light source through the at least first light window and second light window, thereby inducing plasma formation in a balloon fluid, causing rapid bubble formation, and imparting pressure waves upon the treatment site. Plasma and bubble formation is depicted in FIG. 8 as bubbles 814 in proximity to the light windows 808, 810, and 812. The light windows 808, 810, and 812 of light guide 800 can be longitudinally spaced apart with at least one intervening non-emitting portion 820 of the light guide 800 disposed between the plurality of light windows.

In various examples, the light windows, diverting features, or both can vary in size and shape along the length of the catheter. In various examples, the light windows, diverting features, or both can be dome-shaped, square, triangular, circular, rectangular, and the like, and can increase in size moving toward the distal portion. In the example of FIG. 8, the most proximal first diverting feature 802 is smaller than the second diverting feature 804, and the third diverting feature 806 is larger than the second diverting feature 804. In the example of FIG. 8, the most proximal first light window 808 is smaller in surface area than the second light window 810, and the third light window 812 is larger in surface area than the second light window 810.

Figure 9:
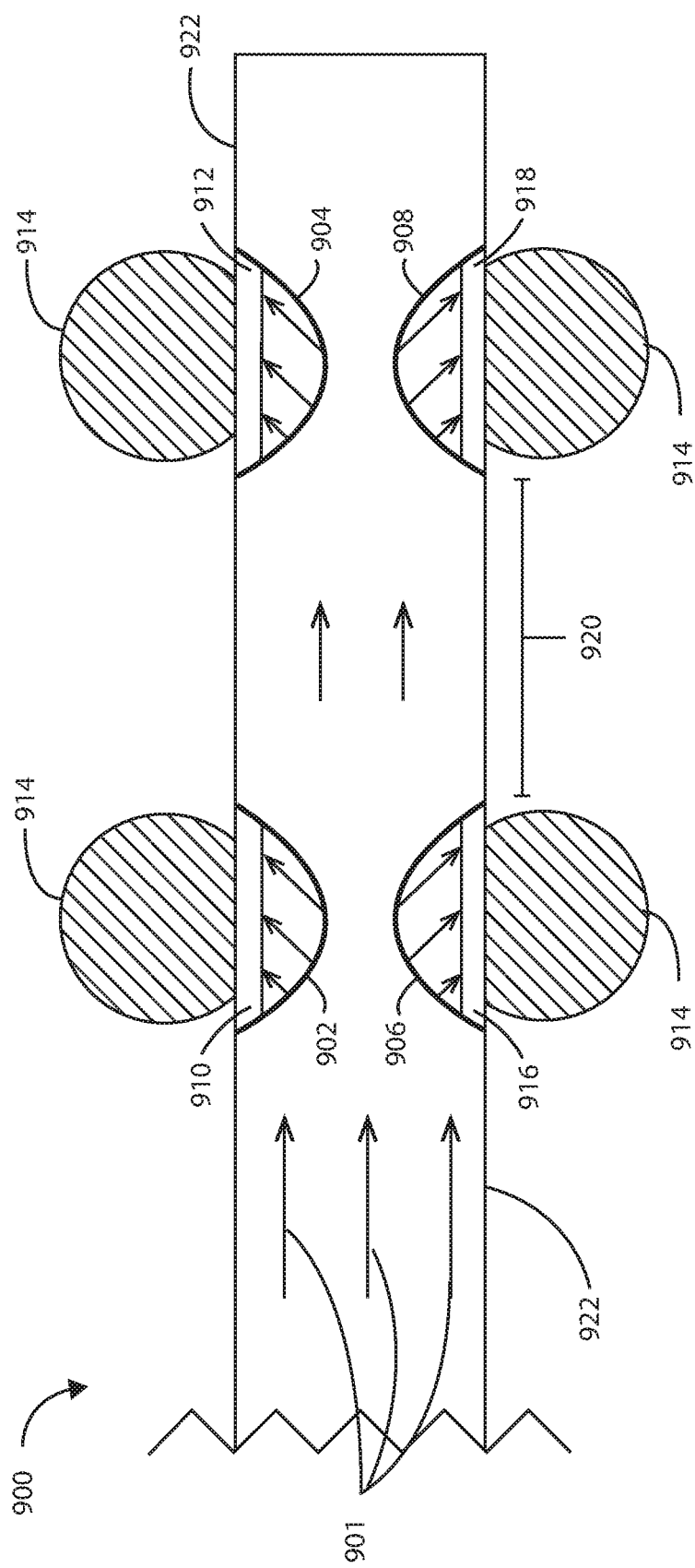
FIG. 9 is a schematic cross-sectional view of a light guide in accordance with various embodiments herein.

While the light windows and diverting features of light guide 800 are shown disposed on one side portion of light guide 800, it is appreciated that the light windows and diverting features can be disposed in many different positions along the elongate shaft. In various examples, light windows and diverting features can be disposed opposite one another along the elongate shaft of the light guide. Referring now to FIG. 9, a schematic cross-sectional view of light guide 900 is shown in accordance with various embodiments herein. Light guide 900 includes diverting features 902, 904, 906, and 908. Each diverting feature directs light 901 from the light guide 900 to exit the light guide 900 at a side surface portion 922 thereof. The side surface portion 922 of the light guide 900 can be a cylindrical side surface portion. The side surface portion 922 of the light guide 900 can be in optical communication with one or more diverting features and one or more light windows, such that the diverting features and light windows are in optical communication with one another.

By way of example, light guide 900 includes a plurality of light windows including a first, second, third, and fourth light windows 910, 912, 916, and 918, respectively, positioned along the elongate shaft of the light guide 900. The first, second, third, and fourth light windows 910, 912, 916, and 918, respectively, can be in optical communication with the first, second, third, and fourth diverting features 902, 904, 906, and 908, respectively, at a plurality of side surface portion 922 of light guide 900. Light within each of the first, second, third, and fourth diverting features 902, 904, 906, and 908 is directed to exit the light guide 900 at a side surface portion 922 and exits through the first, second, third, and fourth light windows 910, 912, 916, and 918, respectively. Light energy can exit light windows 910, 912, 916, and 918 and induce plasma formation in a volume of balloon fluid at or near the light windows 910, 912, 916, and 918, causing rapid bubble formation, and imparting pressure waves upon the treatment site. Plasma and bubble formation is depicted in FIG. 9 as bubbles 914 in proximity to the light windows 910, 912, 916, and 918. The light windows 910, 912, 916, and 918 of light guide 900 can be longitudinally spaced apart with at least one intervening non-emitting portion 920 of the light guide 900 disposed between the plurality of light windows.

Figure 10:
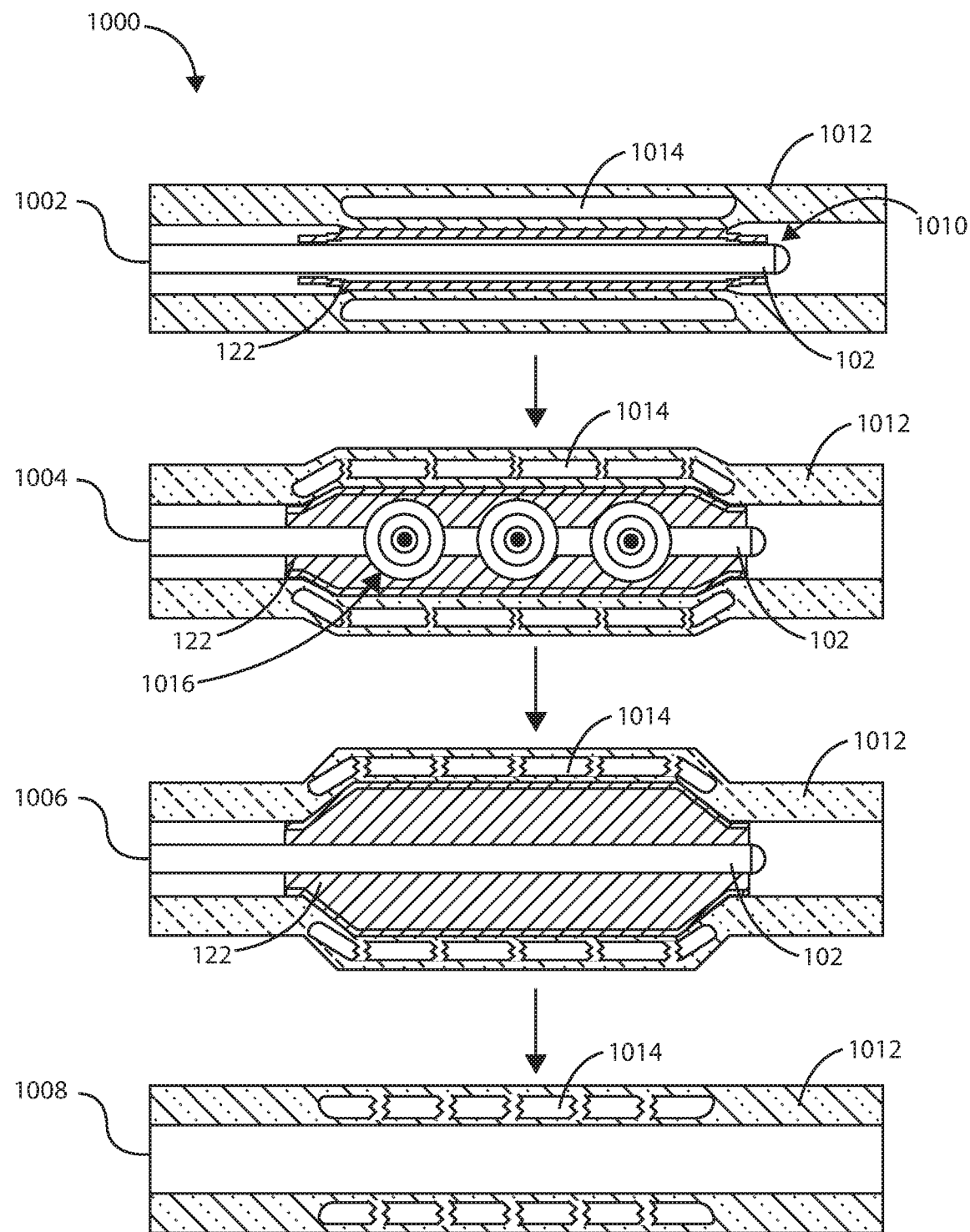
FIG. 10 is a schematic flow diagram for a method in accordance with the various embodiments herein.

The catheters described herein can be used in one or more methods for generating pressure waves to induce fractures in a vascular lesion within or adjacent a vessel wall of a blood vessel. Referring now to FIG. 10, a schematic flow diagram for a method 1000 is shown in accordance with the various embodiments herein. Method 1000 includes advancing a catheter 1010 to a treatment site 1014 within the blood vessel 1012, the catheter 1010 including an elongate shaft 102, and a balloon 122 coupled to the elongate shaft 102 at 1002. In some embodiments, the treatment site 1014 can include a vascular lesion location within a patient's vasculature. In some embodiments, the vascular lesion can include a calcified vascular lesion or a fibrous vascular lesion.

The method 1000 includes expanding the balloon 122 from a collapsed configuration suitable for advancing the catheter 1010 through a patient's vasculature to a first expanded configuration suitable for anchoring the catheter in position relative to the treatment site 1014 at 1004. The method 1000 includes, after expanding the balloon 122, activating a light source in optical communication with each of the first light guide and the second light guide to provide sub-millisecond pulses of light from the light source to the at least first diverting feature and second diverting feature, thereby initiating plasma formation in a balloon fluid, causing rapid bubble formation, and imparting pressure waves 1016 upon the treatment site 1014 at 1004.

In some embodiments, the method 1000 includes a first light guide having a first diverting feature configured to direct light to exit from the first light guide toward a side surface portion of the distal portion of the first light guide and toward the balloon wall, where the first light guide defines a first light window in optical communication with the first diverting feature.

In some embodiments, the method 1000 includes a second light guide having a second diverting feature configured to direct light to exit from the second light guide toward a side surface portion of the distal portion of the second light guide and toward the balloon wall, where the second light guide defines a second light window in optical communication with the second diverting feature.

In some embodiments, the method 1000 includes a third light guide having a third diverting feature configured to direct light to exit from the third light guide toward a side surface portion of the distal portion of the third light guide and toward the balloon wall, where the third light guide defines a third light window in optical communication with the third diverting feature.

In some embodiments, the method 1000 includes a fourth light guide having a fourth diverting feature configured to direct light to exit from the fourth light guide toward a side surface portion of the distal portion of the fourth light guide and toward the balloon wall, where the fourth light guide defines a fourth light window in optical communication with the fourth diverting feature. In some embodiments, the method 1000 includes more than four light guides.

The method 1000 can also include further expanding the balloon 122 from the first expanded configuration to a second further expanded configuration at 1006. The method can include completely removing the catheter 1010 from the patient's vasculature at 1008.

The light guides and components associated therewith that are suitable to be used in the methods herein can be activated in various ways to provide a treatment to a treatment site. In some embodiments, each light guide can be activated simultaneously. In some embodiments, each light guide can be activated sequentially. By way of example, if two light guides are present, they can each be activated at the same time, they can be activated one after the other sequentially, or they can be activated in alternating pairs, semi-randomly, randomly or in another suitable fashion. The light guides can be activated once or multiple times during the course of a treatment. In an embodiment with four light guides, each of the four light guides can be activated at the same time, sequentially, in pairs, or in alternating pairs. By way of example, if four light guides are present, each with one light window, the first and third light guide and their respective light windows can form a pair that can be activated followed by activation of the second and fourth light guide and their respective light windows that can form a pair, either once each or in an ongoing alternating fashion. It is appreciated that many configurations exist for activating multiple light guides and their respective light windows in accordance with the embodiments herein.

Vascular lesions can be present within or about a vessel wall of a blood vessel in various configurations, including surrounding the entire lumen of the vessel or surrounding a portion of the lumen of a vessel. Vascular lesions can also be present in various shapes and sizes. To provide targeted therapy to a vascular lesion, the light guides herein can be configured to be activated depending on the vascular lesion location, shape, and size. By way of example, if a vascular lesion is located partially about the circumference of a blood vessel, the light guides can be activated partially about the circumference of the catheter to match the location, size, and shape of the vascular lesion. In some embodiments, where the vascular lesion spans the entire circumference of the blood vessel, the light guides herein can be activated about the entire circumference of the blood vessel. In various embodiments, the light guides can additionally be activated to match the length and width of the vascular lesion.

The duration of the methods herein can vary according to the specific treatment site and size of a vascular lesion. In some embodiments, the total treatment time can be from one second to one-hundred twenty seconds. In some embodiments, the total treatment time can be from five seconds to twenty seconds. In other embodiments, the total treatment time can be from five seconds to ten seconds. Still alternatively, the total treatment time can fall within or outside of the foregoing ranges, which are not intended to be limiting.

The sub-millisecond pulses of light can be delivered to a treatment site at a frequency of from at least 1 hertz (Hz) to 5000 Hz. In some embodiments, the sub-millisecond pulses of light can be delivered to a treatment site at a frequency from at least 30 Hz to 1000 Hz. In other embodiments, the sub-millisecond pulses of light can be delivered to a treatment site at a frequency from at least 10 Hz to 100 Hz. In yet other embodiments, the sub-millisecond pulses of light can be delivered to a treatment site at a frequency from at least 1 Hz to 30 Hz. In some embodiments, the sub-millisecond pulses of light can be delivered to a treatment site at a frequency that can be greater than or equal to 1 Hz, 2 Hz, 3 Hz, 4 Hz, 5 Hz, 6 Hz, 7 Hz, 8 Hz, or 9 Hz, 10 Hz, 20 Hz, 30 Hz, 40 Hz, 50 Hz, 60 Hz, 70 Hz, 80 Hz, 90 Hz, 100 Hz, 200 Hz, 300 Hz, 400 Hz, 500 Hz, 600 Hz, 700 Hz, 800 Hz, 900 Hz, 1000 Hz, 1250 Hz, 1500 Hz, 1750 Hz, 2000 Hz, 2250 Hz, 2500 Hz, 2750 Hz, 3000 Hz, 3250 Hz, 3500 Hz, 3750 Hz, 4000 Hz, 4250 Hz, 4500 Hz, 4750 Hz, or 5000 Hz or can be an amount falling within a range between any of the foregoing.

Optical Fiber Protection Configurations (FIGS. 11-18)

Figure 11:
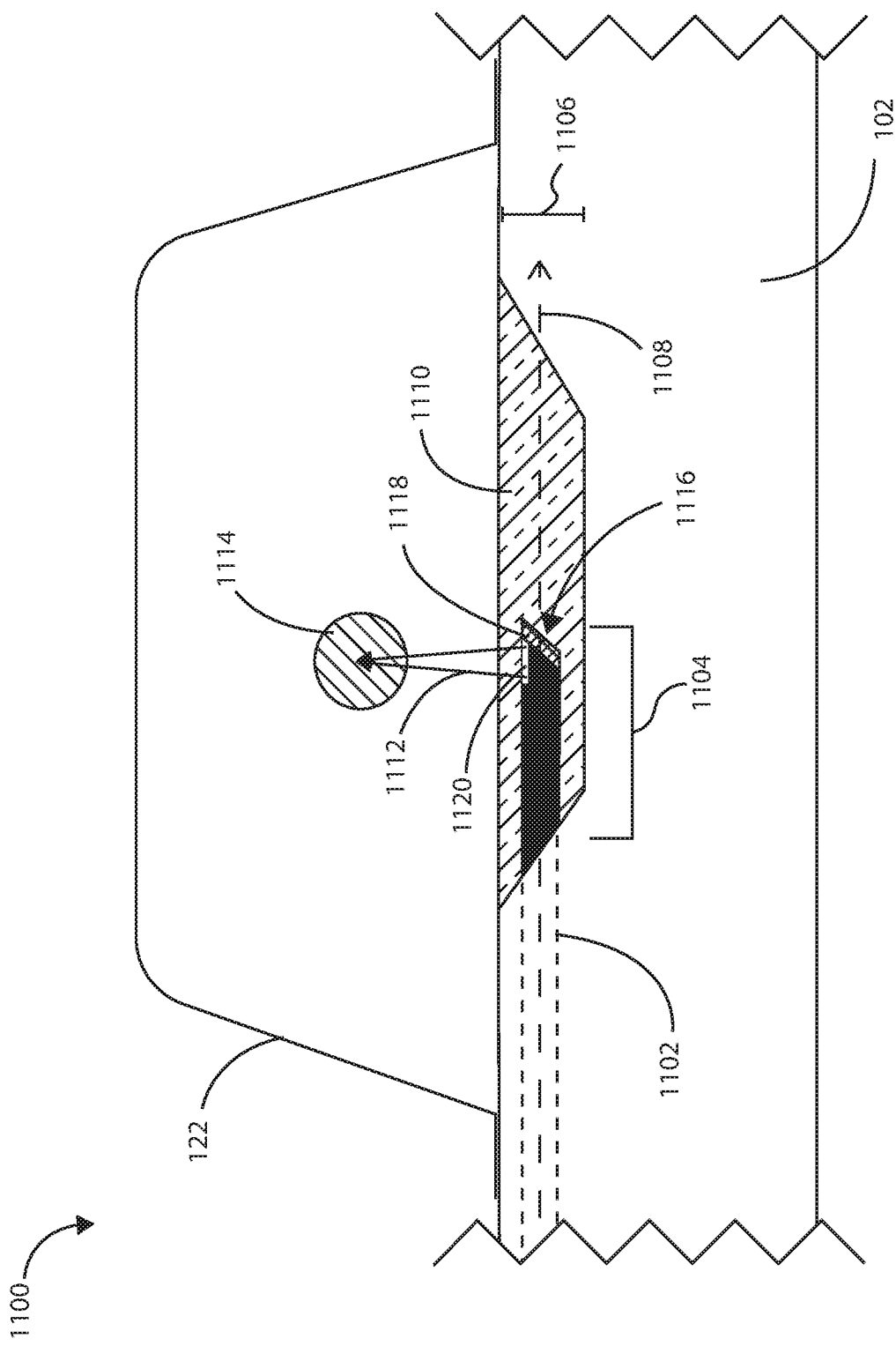
FIG. 11 is a schematic side-view of a catheter, with a partial longitudinal cross-sectional view of a balloon, in accordance with various embodiments herein.

The catheter systems herein can include various configurations that include one or more protection structures configured to provide structural protection to one or more portions of the light guides herein when in the presence of the pressure waves. The catheter systems utilizing protection structures can be suitable for imparting pressure to induce fractures in a vascular lesion within or adjacent a blood vessel wall. Such catheter systems can include a catheter configured to advance to the vascular lesion located within or adjacent a blood vessel. In various configurations the catheters can include an elongate shaft and a balloon coupled to the elongate shaft. The balloon can be configured to be filled with balloon fluid and configured to expand from a collapsed configuration suitable for advancing the catheter through a patient's vasculature to a first expanded configuration suitable for anchoring the catheter in position relative to a treatment site. In the embodiments described herein, the elongate shaft can define a first recess. In some embodiments, the first recess can include a longitudinal recess along a longitudinal surface of the elongate shaft. In some embodiments, the first recess can include a distal tip recess along a longitudinal surface of the elongate shaft. Referring now to FIG. 11, a schematic side-view of a catheter 1100 including a protection structure, with a partial longitudinal cross-sectional view of a balloon 122, is shown in accordance with various embodiments herein.

The catheter 1100 can include a first light guide 1102 disposed along the elongate shaft 102 and within the balloon 122. The first light guide 1102 can be configured to be placed in optical communication with a light source and a balloon fluid. It is appreciated that the first light guide 1102 can include an optical fiber and the light source can include a laser, both of which are described in more detail elsewhere herein. The light source in communication with the light guides herein can be configured to provide pulses of light 1112 to the balloon fluid, thereby initiating plasma formation in the balloon fluid, causing rapid bubble formation of bubble 1114, and imparting pressure waves upon the vascular lesion. The first light guide 1102 can include a longitudinal axis 1108.

A first portion 1104 of the first light guide 1102 can extend into the first recess 1106. In some embodiments, the first portion 1104 includes a distal tip 1116 of the first light guide 1102. The catheter 1100 can include a first protection structure 1110 disposed within the first recess 1106 of the elongate shaft 102 and in contact with the first portion 1104 of the light guide 1102. The first protection structure 1110 can be configured to provide structural protection to the first portion 1104 of the first light guide 1102. In some embodiments, the first protection structure 1110 can be configured to provide structural protection to the first portion 1104, when the first portion 1104 is a distal tip 1116 of a light guide. In other embodiments, the first protection structure 1110 can be configured to provide structural protection to the first portion 1104, when the first portion 1104 is a longitudinal portion of a light guide. The first protection structure 1110 can be configured to provide structural protection to the first portion 1104 of the first light guide 1102 in the presence of the pressure waves. In some examples, the first protection structure 1110 includes a potting material filling the first recess 1106, where the potting material is optically matched to the first light guide 1102. It is appreciated that in some embodiments, the potting material filling the first recess 1106 is not optically matched and can serve as a diverting feature.

As the term is used herein, two materials are "optically matched" if those materials have indices of refraction that are the same when expressed to two decimal places. In other embodiments herein, two materials are not optically matched, or are "optically mismatched", when the two materials that have indices of refraction that are different when expressed to two decimal places.

The light guide 1102 of catheter 1100 can further include a first diverting feature 1118 selected from the group including at least one of a reflecting element, a refracting element, or a fiber diffuser, as will be discussed elsewhere herein. In various embodiments, the diverting feature can include a fiber diffuser selected from a group including of a machined portion of the light guide, a laser-machined portion of the light guide, fiber Bragg gratings, a fused splicing forming at least one internal mirror, and a splicing of two or more diffuse regions. In some embodiments, diverting feature 1118 of catheter 1100 can include a fused splicing forming at least one internal mirror, where the first light guide can include a first longitudinal light window 1120 disposed along a longitudinal length of light guide and in optical communication with the first diverting feature 1118.

It is appreciated that the first portion of the light guides herein that extend into the recess defined by the elongate shaft can include a part of the light guide that extends into the recess, the entire portion of the light guide that extends into recess, or any portion that overlaps with or is present within the recess. In some examples, multiple portions of the light guides herein can extend into more than one recess along the elongate shaft to form a second portion, a third portion, a fourth portion, and the like, of the light guide present within a second recess, a third recess, a fourth recess, and the like.

Figure 12:
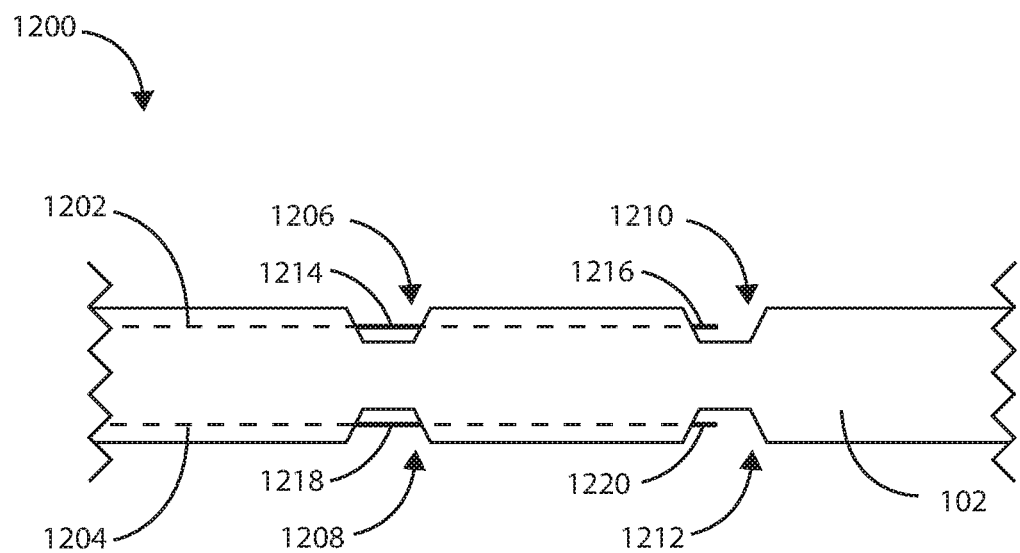
FIGS. 12-13 are schematic side views of an elongate shaft in accordance with various embodiments herein.
Figure 13:
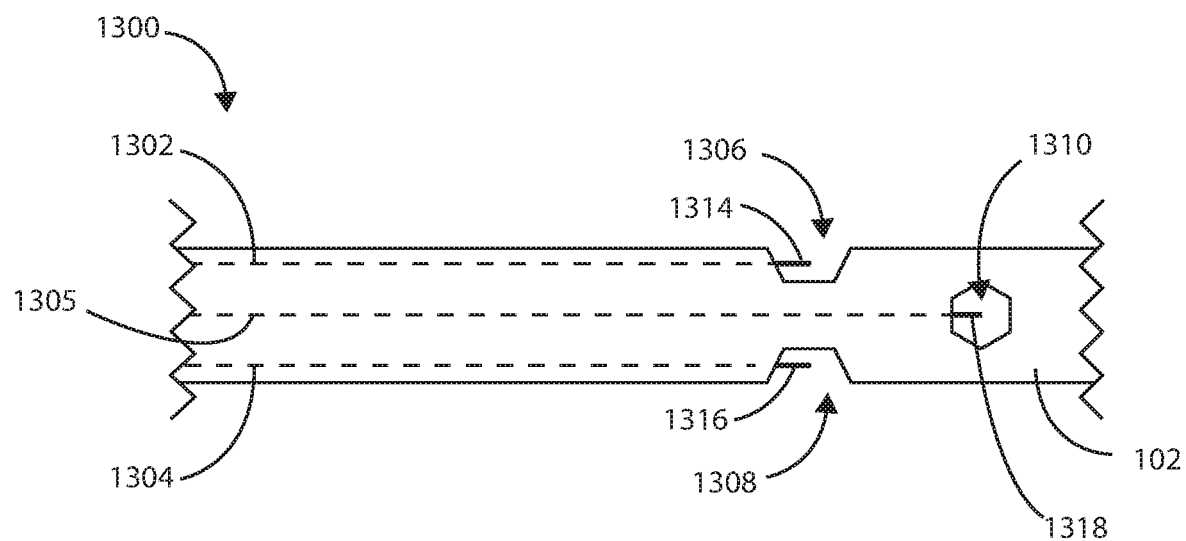
Figure 14:
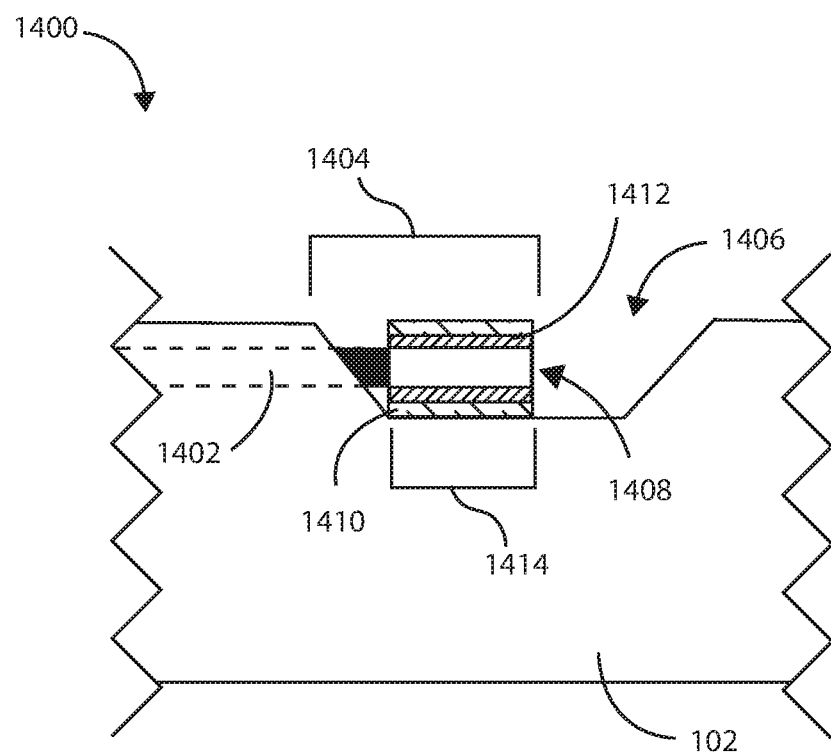
FIGS. 14-15 are schematic cross-sectional views of various distal tip protection structures in accordance with various embodiments herein.

Multiple recesses defined along the longitudinal length of the catheters herein can be suitable for use with one or more light guides disposed along the length of the elongate shaft to provide multiple locations where light can be directed from the light guides. Referring now to FIGS. 12 and 13, schematic side-views of a portion of the elongate shaft of catheters 1200 and 1300 are shown in accordance to various embodiments herein. In the configuration shown in FIG. 12, elongate shaft 102 of catheter 1200 includes a first light guide 1202 and a second light guide 1204. The elongate shaft 102 defines first recesses 1210 and 1212, and second recesses 1206 and 1208, along the longitudinal length. First light guide 1202 extends into second recess 1206 and first recess 1210, such that a first portion 1216 of the first light guide 1202 extends into first recess 1210 and a second portion 1214 of the first light guide 1202 extends into second recess 1206. Second light guide 1204 extends into first recess 1212 and second recess 1208, such that a first portion 1220 of the second light guide 1204 extends into first recess 1212 and a second portion 1218 of the second light guide 1204 extends into second recess 1208.

The second portion 1214 of the first light guide 1202 and the second portion 1218 of the second light guide 1204 each extend through the entire length of the respective second recesses 1206 and 1208. The first light guide 1202 and the second light guide 1204 each extend into multiple recesses. By way of example, the first portion 1216 of the first light guide 1202 and the first portion 1220 of the second light guide 1204 each extend partially into the recesses first 1210 and 1212 such that the first portion 1216 of the first light guide 1202 includes a distal tip of the first light guide 1202 and the first portion 1220 of the second light guide 1204 includes a distal tip of the second light guide 1204. It is appreciated that the first light guide 1202 and the second light guide 1204 are depicted as being disposed 180 degrees about the circumference of the elongate shaft, however, the first light guide 1202 and the second light guide 1204 can be disposed about the elongate shaft in many configurations as discussed elsewhere herein.

In the configuration in FIG. 13, elongate shaft 102 of catheter 1300 includes a first light guide 1302, a second light guide 1304, and a third light guide 1305. While not shown in FIG. 13, it is appreciated that catheter 1300 can further include a fourth light guide disposed 180 degrees about the circumference of the elongate shaft 102 and opposite the third light guide 1305. In various embodiments, catheter 1300 can include more than four light guides. The elongate shaft 102 of catheter 1300 defines recesses 1306, 1308, and 1310, along the longitudinal length. First light guide 1302 extends into first recess 1306 such that a first portion 1314 of the first light guide 1302 extends into first recess 1306. Second light guide 1304 extends into second recess 1308 such that a first portion 1316 of the second light guide 1304 extends into second recess 1308. Third light guide 1305 extends into third recess 1310 such that a first portion 1318 of the third light guide 1305 extends into third recess 1310. The first portions 1314, 1316, and 1318 of the first, second, and third light guide each extend partially into their respective recesses 1306, 1308, and 1310. Each of the first portions 1314, 1316, and 1318 of the first, second, and third light guides 1302, 1304, and 1305 includes a distal tip portion within each recess.

The protection structures suitable for use herein can be tailored to various configurations dependent on if the portion of the light guide to be protected is a distal tip or a longitudinal portion. Referring now to the embodiments in FIGS. 14-18, examples of several side views of an elongate shaft, with longitudinal cross-sectional views of the protection structures, are shown in accordance with various embodiments herein. In the configuration in FIG. 14, catheter 1400 includes a first portion 1404 of a first light guide 1402 that extends into a first recess 1406 defined by the elongate shaft 102 (illustrated in FIG. 1). The catheter 1400 can include a first protection structure 1410 disposed within the first recess 1406 of the elongate shaft 102 and in contact with the first portion 1404 of the light guide 1402. The first protection structure 1410 can be an end cap disposed about the distal portion 1414 of the first portion 1404 of the light guide 1402. The end cap can be flush with a distal tip 1408 of the light guide 1402. The first protection structure 1410 can be adhered to an outer surface of the distal portion 1414 of the first portion 1404 of the light guide 1402 with an adhesive 1412, where the adhesive 1412 and the end cap protection structure 1410 are optically matched to the first light guide 1402. It is appreciated that in some embodiments, the end cap protection structure is not optically matched.

Figure 15:
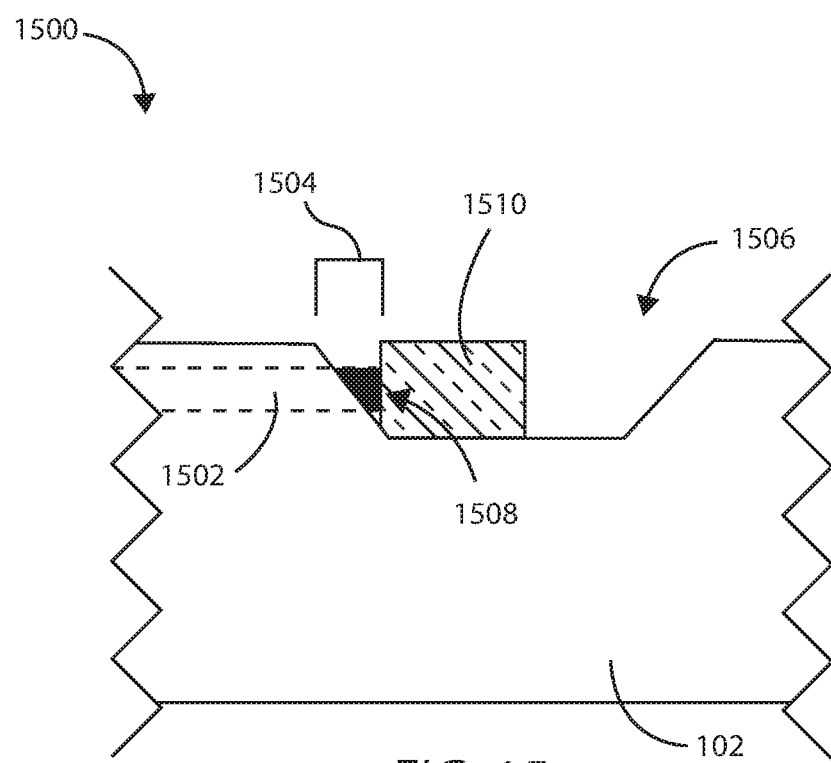

In the configuration in FIG. 15, catheter 1500 includes a first portion 1504 of a first light guide 1502 that extends into a first recess 1506 defined by the elongate shaft 102 (illustrated in FIG. 1). The catheter 1500 can include a first protection structure 1510 disposed within the first recess 1506 of the elongate shaft 102 and in contact with the first portion 1504 of the light guide 1502. The first protection structure 1510 can be a first component that is abutted against and fused to the distal tip 1508 of the first light guide 1502, where the first component protection structure 1510 is optically matched to the first light guide 1502. In various embodiments, the first component protection structure can be made from glass, quartz, sapphire, diamond, and the like. It is appreciated that in some embodiments, the first component protection structure is not optically matched.

Figure 16:
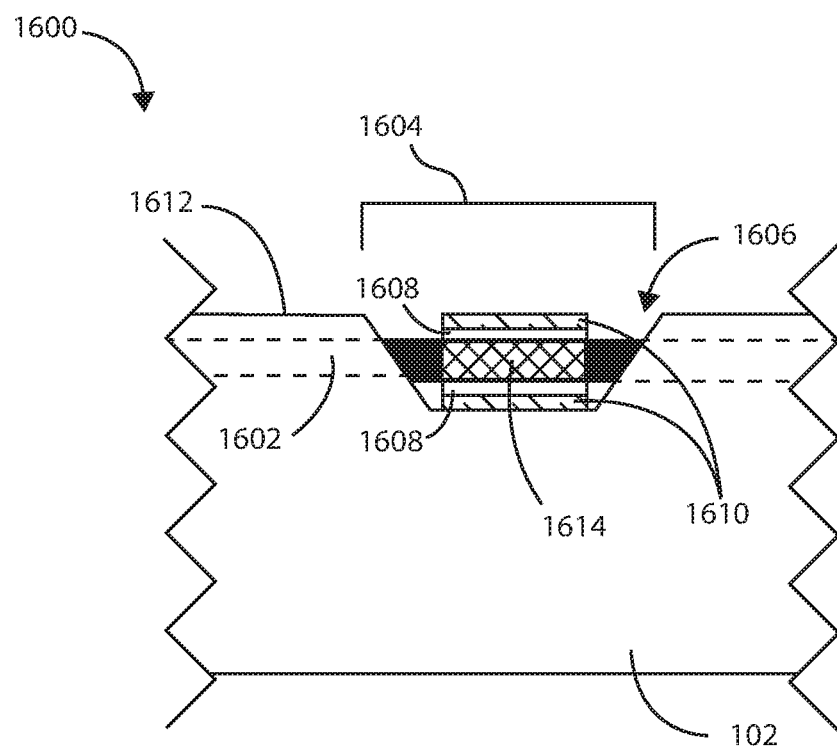
FIGS. 16-18 are schematic cross-sectional views of various longitudinal protection structures in accordance with various embodiments herein.

In the configuration in FIG. 16, catheter 1600 includes a second portion 1604 of a first light guide 1602 that extends into a second recess 1606 defined by the elongate shaft 102 (illustrated in FIG. 1). The second recess 1606 can be disposed within the balloon along a longitudinal surface 1612 of the elongate shaft 102. A second portion 1604 of the first light guide 1602 can extend into or through the second recess 1606, where the second portion 1604 can define a longitudinal light window 1608 disposed along a longitudinal length of the second portion 1604 and in optical communication with a first diverting feature 1614. The catheter 1600 can further include a longitudinal protection structure 1610 in contact with the second portion 1604 of the first light guide 1602 and configured to provide structural protection to the second portion 1604 in the presence of pressure waves. The longitudinal protection structure 1610 can be a sleeve disposed about the longitudinal light window 1608 and can be adhered to the longitudinal surface of the second portion 1604 of the first light guide 1602 with an adhesive (not shown), where the adhesive and the sleeve longitudinal protection structure 1610 are optically matched to the first light guide 1602. In some embodiments, the longitudinal protection structure 1610 and the adhesive are not optically matched.

Figure 17:
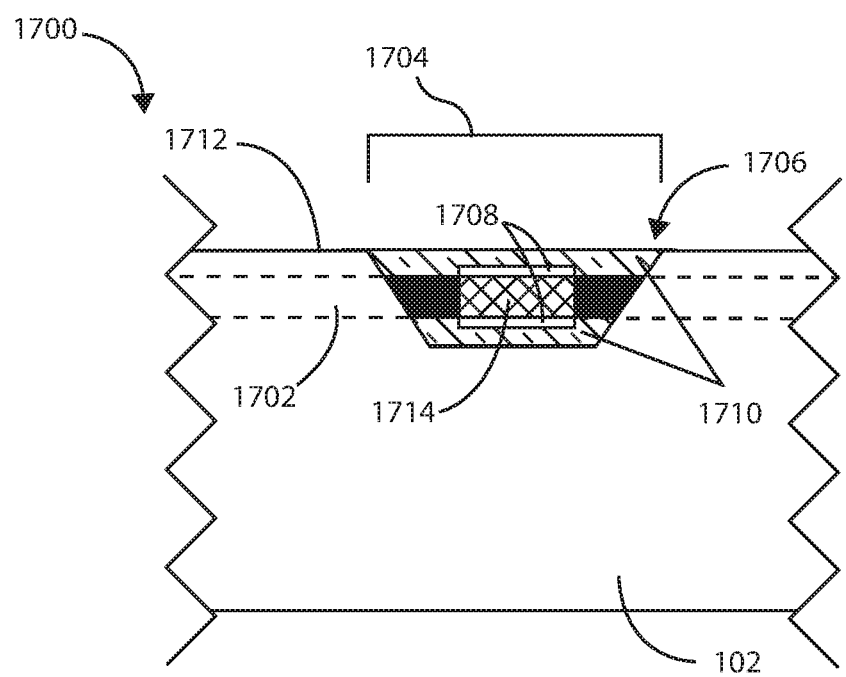

In the configuration in FIG. 17, catheter 1700 includes a second portion 1704 of a first light guide 1702 that extends into or through a second recess 1706 defined by the elongate shaft 102. The second recess 1706 can be disposed within a balloon along a longitudinal surface 1712 of the elongate shaft 102. A second portion 1704 of the first light guide 1702 can extend into or through the second recess 1706, where the second portion 1704 can define a longitudinal light window 1708 disposed along a longitudinal length of the second portion 1704 and in optical communication with a first diverting feature 1714. The catheter 1700 can further include a longitudinal protection structure 1710 in contact with the second portion 1704 of the first light guide 1702 and configured to provide structural protection to the second portion 1704 in the presence of pressure waves. The longitudinal protection structure 1710 can be a potting material disposed within the second recess 1706 and around the second portion 1704 of the first light guide 1702, where the potting material longitudinal protection structure 1710 is optically matched to the first light guide 1702. It is appreciated that in some embodiments, the potting material of the longitudinal protection structure 1710 is not optically matched and can serve as a diverting feature.

Figure 18:
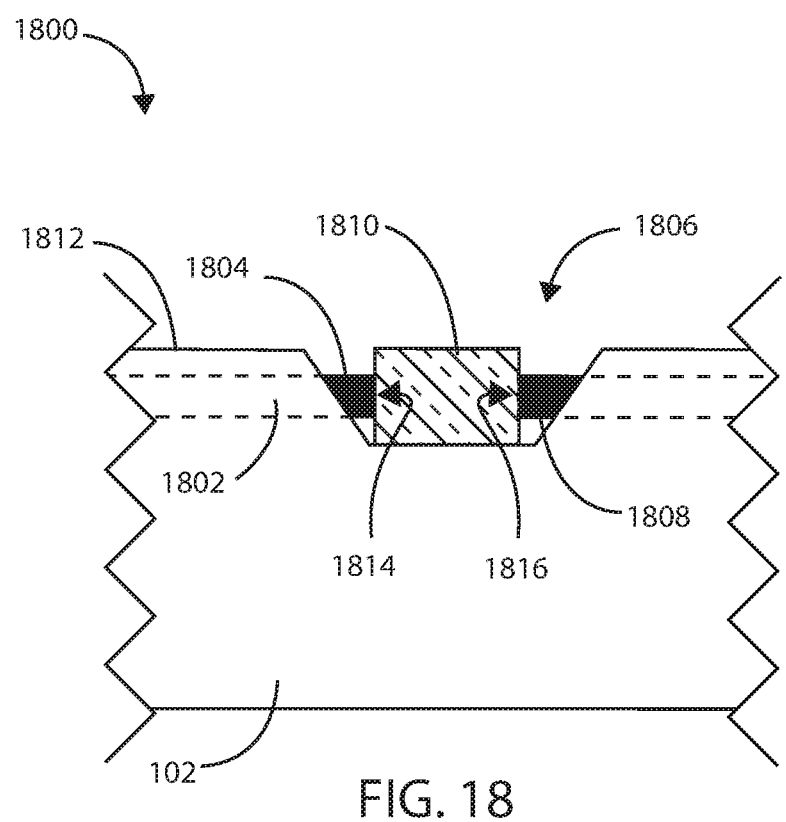

In the configuration in FIG. 18, catheter 1800 includes a proximal portion 1804 of a first light guide 1802 that extends into a proximal recess 1806 defined by the elongate shaft 102, and also includes a proximal tip 1816 of a continuation of the first light guide 1808. The proximal recess 1806 can be disposed within a balloon along a longitudinal surface 1812 of the elongate shaft 102. The catheter 1800 can include a longitudinal protection structure 1810 in contact with the distal tip 1814 of a proximal portion 1804 of the first light guide 1802 and the proximal tip 1816 of the continuation of the first light guide 1808. The longitudinal protection structure 1810 can be a first component fused between the distal tip 1814 of the proximal portion 1804 of the first light guide 1802 and the proximal tip 1816 of the continuation of the first light guide 1808. The fused component longitudinal protection structure 1810 can be configured to provide structural protection to the distal tip 1814 of the proximal portion 1804 of the first light guide 1802 and the proximal tip 1816 of the continuation of the first light guide 1808 in the presence of pressure waves. The first component longitudinal protection structure 1810 can be abutted against and fused to the proximal tip 1816 of the continuation of the first light guide 1808 and the distal tip 1814 of the proximal portion 1804 of the first light guide 1802, where the first component is optically matched to the first and continuation of the first light guides, 1802 and 1808. It is appreciated that in some embodiments, the first component is not optically matched and can serve as a diverting feature.

It is appreciated that the balloons, light guides, and elongate shafts suitable for use with the protection structures can include any of those described elsewhere herein. In various embodiments, the elongate shaft defines an inflation lumen, where the inflation lumen is in fluid communication with the balloon at a distal portion of the elongate shaft.

In an example, a catheter system for imparting pressure to induce fractures in a vascular lesion within or adjacent a blood vessel wall is provided. The catheter system can include a catheter configured to advance to the vascular lesion located within or adjacent a blood vessel. The catheter can include an elongate shaft and a balloon coupled to the elongate shaft. The balloon can be configured to be filled with balloon fluid and configured to expand from a collapsed configuration suitable for advancing the catheter through a patient's vasculature to a first expanded configuration suitable for anchoring the catheter in position relative to a treatment site. The elongate shaft can define a first recess within the balloon. The catheter can include a first light guide disposed along the elongate shaft and within the balloon, the first light guide configured to be placed in optical communication with a light source and a balloon fluid. A first portion of the first light guide can extend into the first recess and can include a distal tip of the first light guide. The catheter can also include a first protection structure disposed within the first recess of the elongate shaft and in contact with the first portion of the light guide, where the first protection structure includes a potting material filling the first recess, where the potting material is optically matched to the first light guide. It is appreciated that in some embodiments, the first protection structure is not optically matched.

The catheter system can include a light source that is configured to provide pulses of light to the balloon fluid, thereby initiating plasma formation in the balloon fluid, causing rapid bubble formation, and imparting pressure waves upon the vascular lesion. The first protection structure can be configured to provide structural protection to the first portion and distal tip of the first light guide in the presence of the pressure waves. In some embodiments, the first protection structure can include a potting material that fills the first recess and includes a potting material outer surface that is flush with an outer surface of the elongate shaft. In some embodiments, the first protection structure can include a potting material that partially fills the first recess and includes a potting material outer surface that is not flush with the outer surface of the elongate shaft. In yet other embodiments, the first protection structure can include a potting material that over fills the first recess and includes a potting material outer surface that forms a dome-shaped surface that extends past an outer surface of the elongate shaft, and in some embodiments the dome-shaped surface of the potting material can act as a focusing element.

The various protection structures described herein can include, but are not to be limited to, end cap protection structures, sleeve protection structures, potting material protection structures, and fused component protection structures. The protection structures can be configured to protect a portion of a light guide that can include a distal tip, a longitudinal portion, or both. In one embodiment for protection of a distal tip, an end cap protection structure can include an annular cylinder shape about a distal tip of a light guide. In one embodiment, the distal tip of the first light guide can be flush with a distal tip of the end cap and not obstructed by the end cap. In other embodiments, the distal tip of the first light guide can be flush with a distal tip of the end cap and covered by an optically matched material. In another embodiment for protection of a distal tip, a protection structures that includes potting material can be used to cover the entire outer surface of a distal tip. In various embodiments, the potting material can fill the recess so that an outer surface of the potting material is continuous with an outer surface of the elongate shaft. In some embodiments, a potting material can completely surround a distal tip of the first light guide. In other embodiments, a potting material can partially surround a distal tip of the first light guide. In yet another embodiment for protecting a distal tip, the protection structures can include fused components, where the fused component can include a solid cylindrical shape. In some embodiments, the fused component material can be harder and more durable than the material of the light guides herein. In some embodiments, the fused component can include a material such as a glass, sapphire, diamond, and the like.

Various examples of protection structures suitable for protecting a longitudinal portion of a light guide disposed in a recess can include a sleeve, a potting material, and a fused component. In one embodiment for protection of longitudinal portion of a light guide, a sleeve protection structure can include an annular cylinder shape disposed about a longitudinal portion of a light guide. In various embodiments, the potting material can fill the recess so that an outer surface of the potting material is continuous with an outer surface of the elongate shaft. In some embodiments, a potting material can completely surround a longitudinal portion of the first light guide. In other embodiments, a potting material can partially surround a longitudinal portion of the first light guide. In some embodiments, the potting material can fill a recess and include a potting material outer surface that is flush with the outer surface of the elongate shaft. In some embodiments, the potting material can partially fill a recess and include a potting material outer surface that is not flush with the outer surface of the elongate shaft. In yet other embodiments, the potting material can over fill a recess and include a potting material outer surface that forms a dome-shaped surface that extends past an outer surface of the elongate shaft, and in some embodiments the dome-shaped surface can act as a focusing element. In yet another embodiment for protecting a longitudinal portion, the protection structures can include fused components, where the fused component can include a solid cylindrical shape disposed between two light guides. In some embodiments, the fused component material can be harder and more durable than the material of the light guides herein. In some embodiments, the fused component can include a material such as a glass, sapphire, diamond, and the like. In some examples, the first longitudinal protection structure is completely within the first longitudinal recess. In some examples, the first longitudinal protection structure protrudes from the first longitudinal recess.

The light guides including protection structures as described can be used in various methods for generating pressure waves to induce fractures in a vascular lesion within or adjacent a vessel wall of a blood vessel. In one embodiment, the method can include advancing a catheter to a vascular lesion within the blood vessel, where the catheter includes an elongate shaft, a balloon coupled to the elongate shaft, and at least a first light guide disposed along the elongate shaft within the balloon. The first light guide can be configured to be placed in optical communication with a light source and a balloon fluid. A first portion of the first light guide can be disposed within a first recess defined by the elongate shaft, where the first portion of the first light guide can be in contact with a first light guide protection structure. The method can include expanding the balloon from a collapsed configuration suitable for advancing the catheter through a patient's vasculature to a first expanded configuration suitable for anchoring the catheter in position relative to a vascular lesion. The method can include, after expanding the balloon, activating a light source in optical communication with the first light guide to direct light from within the first light guide to initiate plasma formation in the balloon fluid and to cause rapid bubble formation, thereby imparting pressure waves upon the vascular lesion, wherein the first light guide protection structure is configured to provide structural protection to the distal tip in the presence of the pressure waves. In some embodiments, the method can include catheters where the first portion includes a distal tip of the first light guide, and where the first protection structure can be configured to provide structural protection to the distal tip of the first light guide. In various embodiments, the method can include, after activating the light source, further expanding the balloon from the first expanded configuration to a second further expanded configuration.

Figure 19:
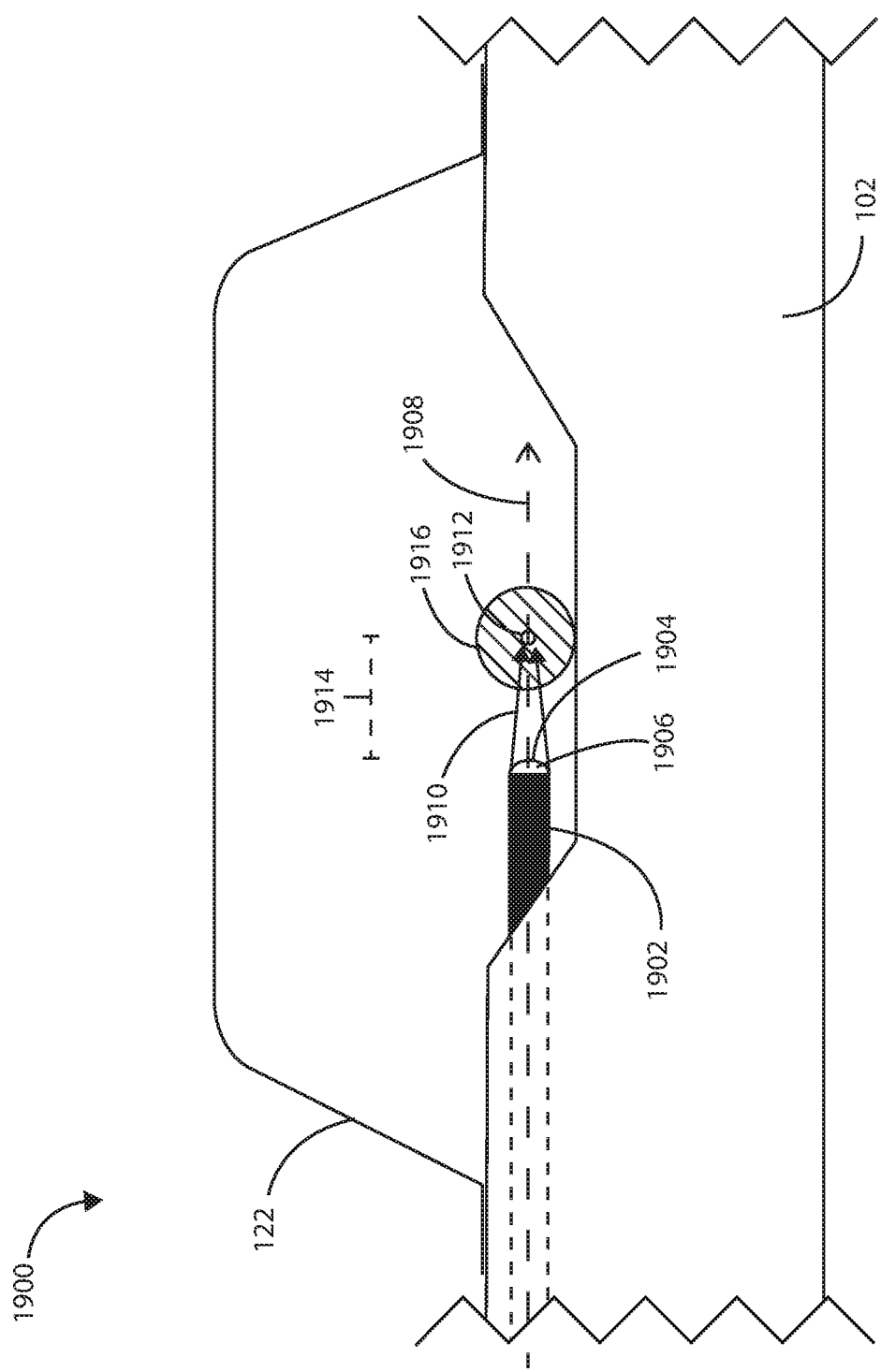
FIG. 19 is a schematic side-view of a catheter, with a partial longitudinal cross-sectional view of a balloon, in accordance with various embodiments herein.
Figure 20:
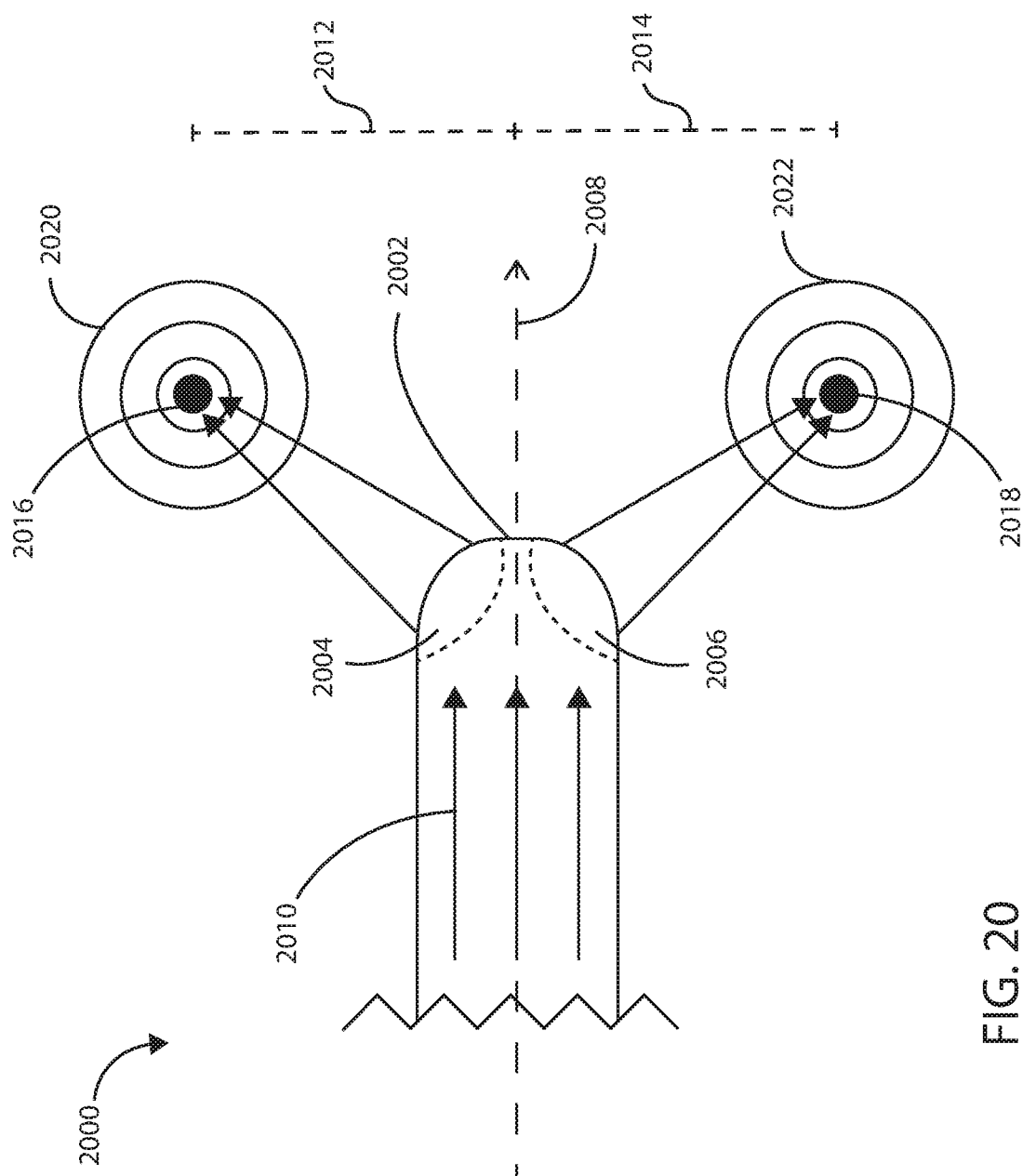
FIGS. 20-21 are schematic cross-sectional views of various light guides having multiple focusing elements in accordance with various embodiments herein.
Figure 21:
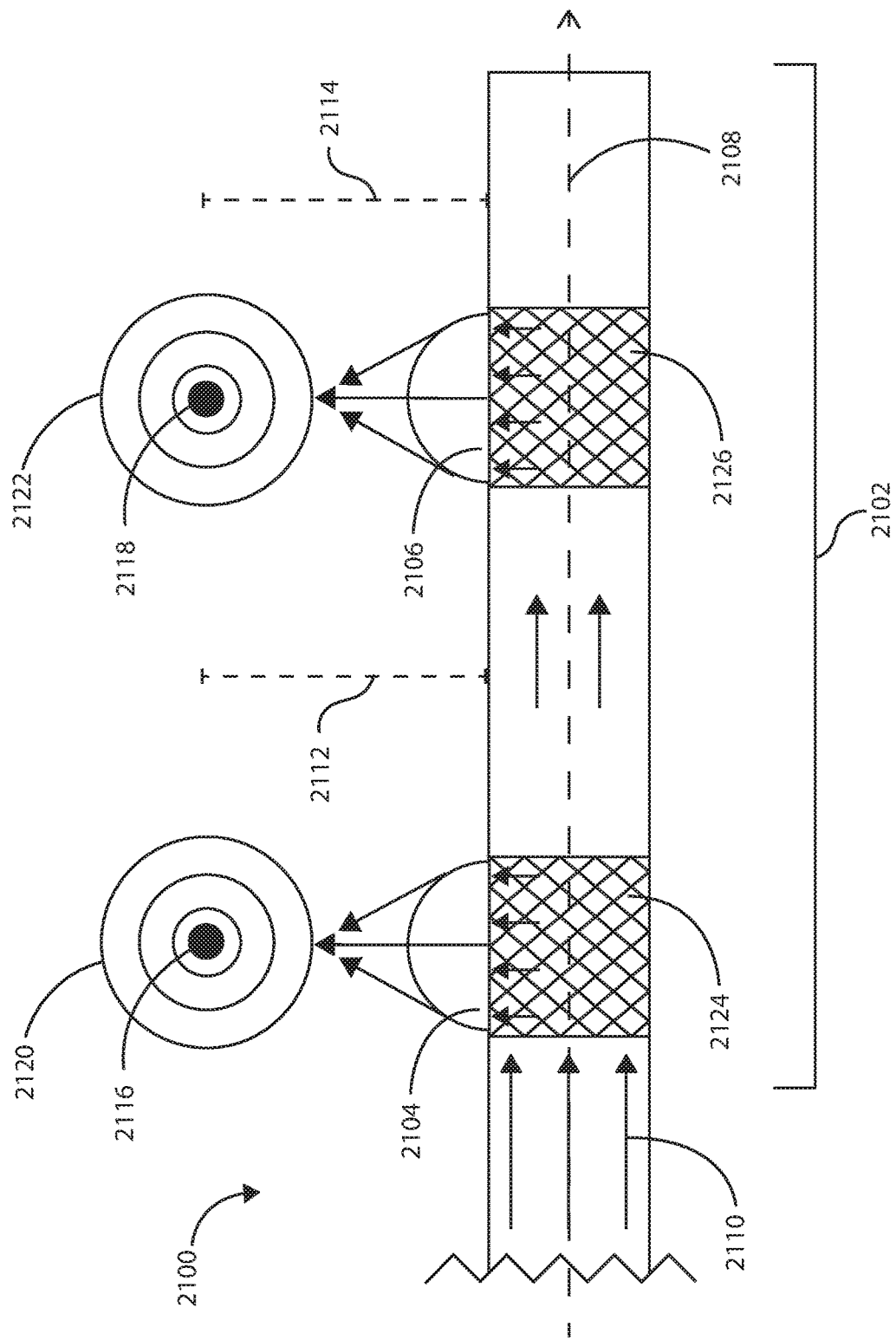

Focusing Element Configurations (FIGS. 19-21)

The catheter systems herein can include various focusing elements to direct light from within a light guide to a location away from the light guide. Light directed to a location away from the light guide can initiate a plasma formation within a balloon fluid at the location. The catheter systems including focusing elements are designed to impart pressure to induce fractures in a vascular lesion within or adjacent a blood vessel wall. Beneficial therapy effects may be enjoyed by initiating the plasma formation at a location away from the light guide instead of immediately adjacent to the light guide. The light guide may be less likely to be damaged by the plasma initiation event, the resulting pressure, or the resulting bubble dynamics if the plasma formation location is at a location away from the light guide rather than immediately adjacent to the light guide.

As discussed elsewhere herein, the catheter systems can include a catheter that can be configured to advance to the vascular lesion located within or adjacent a blood vessel. The catheter can include an elongate shaft and a balloon coupled to the elongate shaft. The balloon can include a balloon wall and it can be configured to expand from a collapsed configuration suitable for advancing the catheter through a patient's vasculature to a first expanded configuration suitable for anchoring the catheter in position relative to a vascular lesion. The catheters herein can include a first light guide disposed along the elongate shaft and within the balloon, where the first light guide can be configured to be placed in optical communication with a light source and a balloon fluid. It is appreciated that the first light guide can include an optical fiber and the light source can include a laser, both of which are described in more detail elsewhere herein.

The first light guide can include at least a first focusing element located at a distal portion of the first light guide within a balloon and in optical communication with the light source. Referring now to FIG. 19, a schematic side-view of a catheter 1900, with a partial longitudinal cross-sectional view of a balloon, is shown in accordance with various embodiments herein. Catheter 1900 includes an elongate shaft 102, a balloon 122, and a first light guide 1902 disposed along the elongate shaft 102 and within the balloon 122. The first light guide 1902 can be configured to be in optical communication with a light source at its proximal end and with a balloon fluid at its distal end. In some embodiments, the distal portion of the first light guide can include a distal tip of the first light guide. In other embodiments, the distal portion of the first light guide can include a longitudinal portion thereof. The elongate shaft 102 of catheter 1900 can define an inflation lumen (not shown), where the inflation lumen can be in fluid communication with the balloon 122 at a distal portion of the elongate shaft 102.

In the configuration shown in FIG. 19, the first light guide 1902 includes a distal tip 1904, and a first focusing element 1906 disposed at the distal tip 1904. The first light guide 1902 can include a longitudinal axis 1908. The first focusing element 1906 can be configured to direct light 1910 from within the first light guide 1902 to a first location 1912 at a first distance 1914 away from the distal tip 1904 of the first light guide 1902. Light directed to the first location 1912 can initiate plasma formation in the balloon fluid away from the distal tip 1904 and to cause rapid bubble formation, thereby imparting pressure waves upon the vascular lesion. The first location 1912 can be spaced away from the distal tip 1904 and centered on a longitudinal axis 1908 of the first light guide 1902. The formation of plasma and bubble 1916 within the balloon fluid can originate at the first location 1912 at a first distance 1914 spaced away from the distal tip 1904 and centered on a longitudinal axis 1908 of the first light guide 1902. The first light guide 1902 can also include a first diverting feature (not shown) in optical communication with the focusing element and located at a distal portion of the first light guide, where the diverting feature is configured to direct light from within the first light guide toward a first focusing element and toward the balloon wall away from, or off of, the longitudinal axis.

In some embodiments, the first light guide 1902 can include a second focusing element located at a distal portion of the first light guide, where the second focusing element can be configured to direct light from within the first light guide to a second location at a second distance away from the distal portion of the first light guide to initiate plasma formation in the balloon fluid away from the distal portion and to cause rapid bubble formation, thereby imparting pressure waves upon the vascular lesion. The second focusing element may also be located on the distal tip along with the first focusing element 1906, such as the embodiment described with respect to FIG. 20. The second focusing element may also be located along a longitudinal surface of the light guide, similar to one of the focusing elements shown in the embodiment of FIG. 21.

In addition or alternatively, in other embodiments, catheter 1900 can include a second light guide coupled to the elongate shaft. The second light guide can be in optical communication with a light source and a balloon inflation fluid, where the second light guide can be in optical communication with the light source and the balloon inflation fluid. The second light guide can include a focusing element of the second light guide located at a distal portion of the second light guide and in optical communication with the light source. The focusing element of the second light guide can be configured to direct light from within the second light guide to a second location at a second distance from the distal portion of the second light guide to initiate plasma formation in the balloon fluid away from the distal portion and to cause rapid bubble formation, thereby imparting pressure waves upon the vascular lesion. It is appreciated that multiple light guides, each having multiple focusing elements, can be used in the catheter systems herein.

The focusing elements herein can direct light from within a light guide to one or more locations at a distance of at least 1 micrometers (μm) and at most 5 millimeters (mm) away from the distal tip of the first light guide. In an embodiment, the focusing elements herein can direct light from within a light guide to one or more locations at a distance of at least 10 μm and at most 5 mm away from the distal tip of the first light guide. In some embodiments, the focusing elements herein can direct light from within a light guide to a distance of greater than or equal to 1 μm, 2 μm, 3 μm, 4 μm, 5 μm, 6 μm, 7 μm, 8 μm, 9 μm, 10 μm, 20 μm, 30 μm, 40 μm, 50 μm, 60 μm, 70 μm, 80 μm, 90 μm, 100 μm, 200 μm, 300 μm, 400 μm, 500 μm, 600 μm, 700 μm, 800 μm, 900 μm, 1 mm, 2 mm, 3 mm, 4 mm, or 5 mm, away from the distal tip of the first light guide, or can be an amount falling within a range between any of the foregoing. In some embodiments, the focusing elements herein can direct light from within a light guide to one or more locations at a distance greater than 1 mm.

The light guides suitable for use in the catheter systems herein can include multiple focusing elements in a distal portion, as will be discussed in reference to FIGS. 20 and 21. In the configuration in FIG. 20, a longitudinal cross-sectional view of light guide 2000 is shown in accordance with various embodiments herein. The light guide 2000 can be disposed along an elongate shaft of a catheter and placed in optical communication with a light source and a balloon fluid. The light guide 2000 can include a distal portion, where the distal portion can be a distal tip 2002. Light guide 2000 can further include a first focusing element 2004 and a second focusing element 2006. In the example of FIG. 20, both the first focusing element 2004 and the second focusing element 2006 are located at the distal tip 2002 of the light guide 2000. The first focusing element 2004 can be configured to direct light 2010 from within the light guide 2000 to a first location 2016 at a first distance 2012 spaced away from the longitudinal axis 2008 of the light guide 2000 to initiate plasma formation in the balloon fluid at the first location 2016. Formation of plasma at the first location 2016 can cause rapid bubble formation of bubble 2020, thereby imparting pressure waves upon the vascular lesion. The second focusing element 2006 can be configured to direct light 2010 from within the light guide 2000 to a second location 2018 at a second distance 2014 spaced away from the longitudinal axis 2008 of the light guide 2000 to initiate plasma formation in the balloon fluid away at the second location 2018. Formation of plasma at the second location 2018 can cause rapid bubble 2022 formation, thereby imparting pressure waves upon the vascular lesion. In the embodiment shown in FIG. 20, the first distance 2012 is equal to or approximately equal to the second distance 2014, the first location 2016 is off-axis in one direction, and the second location 2018 is off-axis in a different direction. In some embodiment, the first distance 2012 is not equal to the second distance 2014.

In the configuration in FIG. 21, a longitudinal cross-sectional view of light guide 2100 is shown in accordance with various embodiments herein. The light guide 2100 can be disposed along an elongate shaft of a catheter and placed in optical communication with a light source and a balloon fluid. The light guide 2100 can include a distal portion, such as a longitudinal distal portion 2102. The light guide 2100 can include a first diverting feature 2124 located at a distal portion of the first light guide and configured to direct light from within the first light guide toward a first focusing element 2104. In some examples, the first focusing element 2104 can be configured to direct light from within the light guide 2100 to a location in the balloon fluid away from a longitudinal axis 2108 of the first light guide 2100. In some examples, the light guide 2100 can include a second diverting feature 2126, where the second diverting feature is located at a distal portion of the first light guide and configured to direct light from within the first light guide toward a second focusing element 2106. In some examples, the second focusing element 2106 can be configured to direct light from within the light guide 2100 to a location in the balloon fluid away from a longitudinal axis 2108 of the elongate shaft.

The first focusing element 2104 can be configured to direct light 2110 from within the light guide 2100 to a first location 2116 at a first distance 2112 from the first light guide 2100, which is spaced away from the longitudinal axis 2108 of the light guide 2100 to initiate plasma formation in the balloon fluid at the first location 2116 and to cause rapid bubble 2120 formation, thereby imparting pressure waves upon the vascular lesion. The second focusing element 2106 can be configured to direct light 2110 from within the light guide 2100 to a second location 2118 at a second distance 2114 from the first light guide 2100, which is spaced away from the longitudinal axis 2108 of the light guide 2100 to initiate plasma formation in the balloon fluid away at the second location 2118 and to cause rapid bubble 2122 formation, thereby imparting pressure waves upon the vascular lesion. In the embodiment shown in FIG. 21, the first distance 2112 and second distance 2114 are the same. In some embodiments, the first distance 2112 and second distance 2114 can be different. It is appreciated that the diverting features can be tailored to increase or decrease the distance that the light from within the light guide is focused at a location spaced away from the longitudinal axis.

Diverting features suitable for use with the focusing elements herein such as the embodiment of FIG. 21, can include, but are not to be limited to, any feature of the system herein that diverts light from the light guide away from its axial path toward a side surface portion of the light guide. Examples include a reflector, a refracting element, and a fiber diffuser, as will be discussed in more detail below. It is appreciated that the light guides used in the catheter systems herein can include a second, third, fourth, fifth, or sixth focusing element. In some embodiments, the light guides herein can include more than six focusing elements. The focusing elements suitable for use herein can include one or more structures such as a convex lens, a convex mirror, or a gradient-index (GRIN) lens. In some examples, the focusing elements utilized in the light guides herein can be a GRIN lens. In other examples, the focusing elements utilized in the light guides herein can include convex lenses. In yet other embodiments, the focusing elements utilized in the light guides herein can include convex mirrors. In various embodiments, a GRIN lens, convex lens, or convex mirror can be adhered to or fused to a side surface portion or distal tip of the light guides herein with an optically matched adhesive. Adhesives suitable for use with the focusing elements herein can include optically matched or optically mismatched adhesives.

The focusing elements can be located at a distal tip of the light guides herein or disposed along the longitudinal axis of the light guides. The focusing elements described herein can be present in a distal tip of the light guides or along one or more locations along a longitudinal portion of the light guides.

The light guides including focusing elements as described can be used in various methods for generating pressure waves to induce fractures in a vascular lesion within or adjacent a vessel wall of a blood vessel. In one embodiment, the method can include advancing a catheter to a vascular lesion within the blood vessel, where the catheter includes an elongate shaft, a balloon coupled to the elongate shaft, and at least a first light guide disposed along the elongate shaft within the balloon. The first light guide can be configured to be placed in optical communication with a light source and a balloon fluid. The method can include expanding the balloon from a collapsed configuration suitable for advancing the catheter through a patient's vasculature to a first expanded configuration suitable for anchoring the catheter in position relative to a vascular lesion. The method can further include, after expanding the balloon, activating a light source in optical communication with the first light guide to direct light from within the first light guide to a first location at a first distance away from the distal portion of the first light guide to initiate plasma formation in the balloon fluid away from the distal portion and to cause rapid bubble formation, thereby imparting pressure waves upon the vascular lesion. The first location is spaced away from the distal tip and is centered on a longitudinal axis of the first light guide. In various embodiments, the first location can be spaced away from the distal end of the light guide such that it is off-axis from the longitudinal axis of the light guide, or away from the longitudinal axis of the light guide. The method can further include, after activating the light source, further expanding the balloon from the first expanded configuration to a second further expanded configuration.

Figure 22:
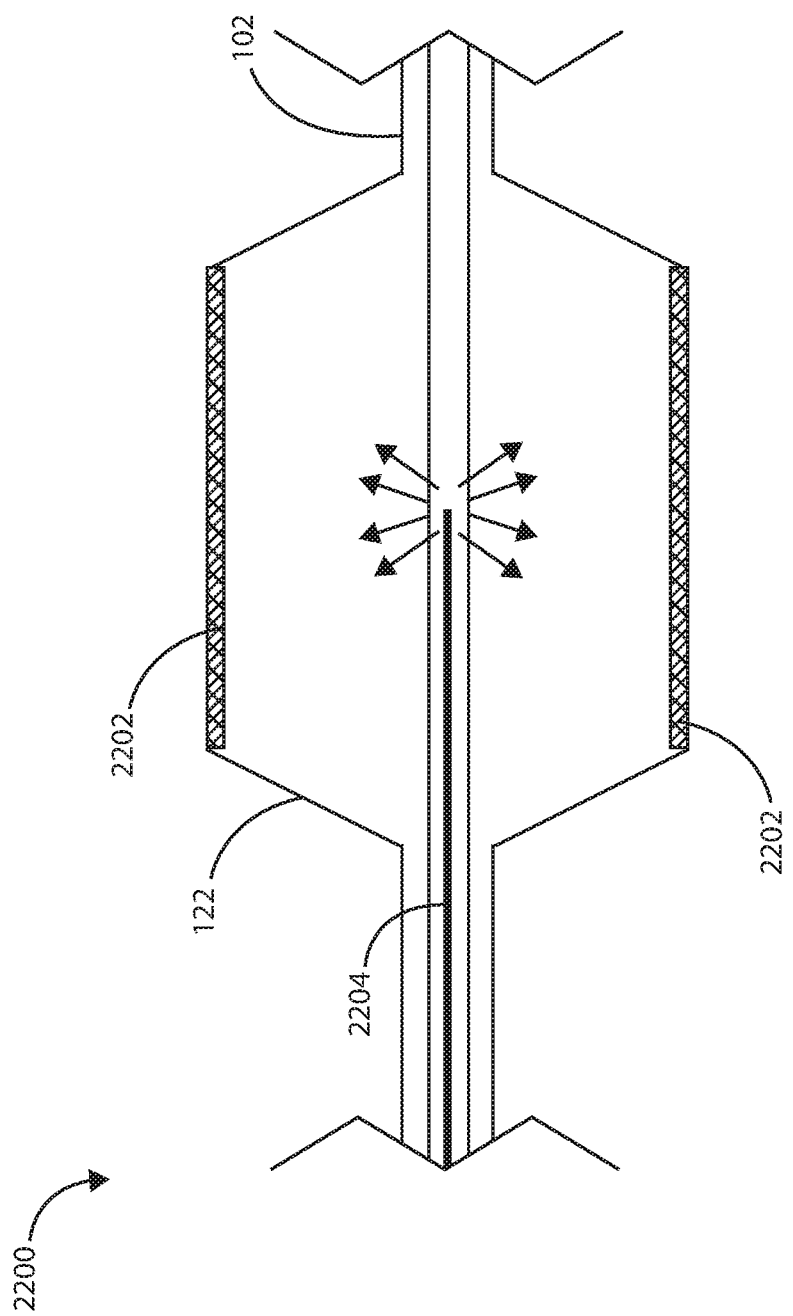
FIGS. 22-23 are cross-sectional views of various catheters including a fortification component coating on a surface within a balloon.
Figure 23:
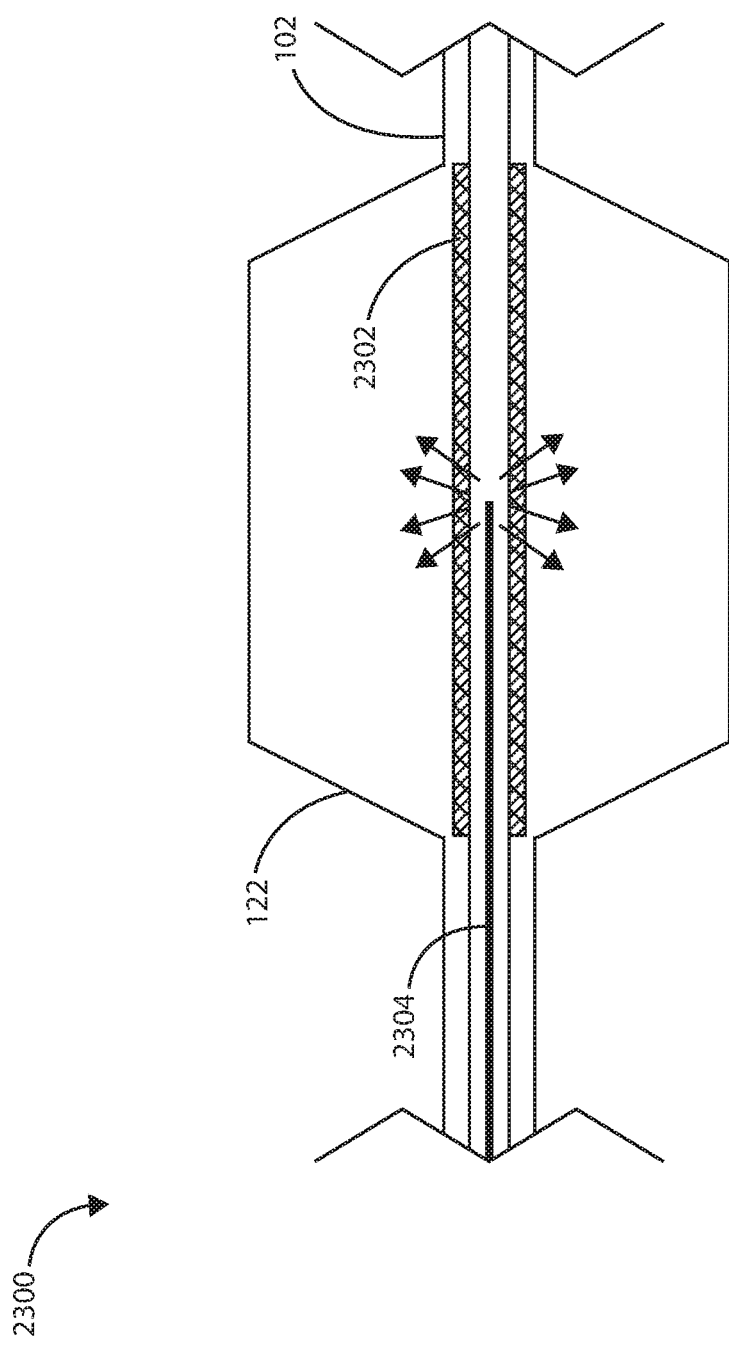

Fortified Balloon Inflation Fluids (FIGS. 22 and 23)

The balloons herein can be inflated with a fortified balloon inflation fluid that is configured to reduce a threshold for inducing plasma formation in the fortified balloon inflation fluid when compared to a base inflation fluid. The fortified balloon inflation fluid can be used in the catheter systems embodied herein. Briefly, the fortified balloon inflation fluid can be used in a catheter system for imparting pressure to induce fractures in a vascular lesion within or adjacent a blood vessel wall. The catheter systems can include a catheter that can be configured to advance to the vascular lesion located within or adjacent a blood vessel. The catheter can include an elongate shaft, where a balloon can be coupled to the elongate shaft, and where the balloon includes a balloon wall. The elongate shaft can define an inflation lumen, where the inflation lumen can be in fluid communication with the balloon at a distal portion of the elongate shaft and in fluid communication with a fluid source at a proximal end of the elongate shaft. The balloon can be configured to expand from a collapsed configuration suitable for advancing the catheter through a patient's vasculature to a first expanded configuration suitable for anchoring the catheter in position relative to a vascular lesion. The balloon can also be configured to expand to a second further expanded configuration. The catheter suitable for use with the fortified balloon inflation fluid can assume many configurations as discussed elsewhere herein.

The fortified balloon inflation fluids described herein can include a base inflation fluid and a fortification component. The fortification component can reduce a threshold for inducing plasma formation in the fortified balloon inflation fluid compared to the base inflation fluid. In some embodiments, the fortification component can include carbon or iron. In some embodiments the fortification element can include iron dextran. In other embodiments, the fortification component can include carbon. In yet other embodiments, the fortification component can include nanoparticles. Various examples of fortification components suitable for use herein include, but are not to be limited to, iron nanoparticles, gold nanoparticles, copper nanoparticles, carbon nanoparticles, carbon nanotubes, including, but not to be limited to single walled carbon nanotubes or double walled carbon nanotubes or mixtures thereof, gold-coated carbon nanotubes, or copper-coated carbon nanotubes. The fortification component can modify various physical parameters of the fortified balloon inflation fluid, such as, but not limited to, viscosity, density, or surface tension. The fortification component can be configured to increase or decrease one or more the viscosity, density, or surface tension of the fortified balloon inflation fluid compared to the base inflation fluid.

The base inflation fluids herein can include those having a mixture of saline and contrast medium. The ratios of the saline and contrast medium can be tailored for treatment at vascular lesion within a vessel wall. In some embodiment, the saline and contrast medium can be present within the base inflation fluid in a ratio of saline to contrast medium of 25:75 volume percent to 75:25 volume percent. In some examples, the ratio of saline to contrast medium within the base inflation fluid can be 25:75 volume percent. In other examples, the ratio of saline to contrast medium within the base inflation fluid can be 50:50 volume percent. In yet other examples, the ratio of saline to contrast medium within the base inflation fluid can be 75:25 volume percent.

Fortified balloon inflation fluids having iron dextran as the fortification component can include a concentration of iron dextran from at least 0.0001 (millimole per liter) mmol/L to 1.0 mmol/L. In some embodiments, the concentration of iron dextran can be greater than or equal to 0.0001 mmol/L, 0.0002 mmol/L, 0.0003 mmol/L, 0.0004 mmol/L, 0.0005 mmol/L, 0.0006 mmol/L, 0.0007 mmol/L, 0.0008 mmol/L, 0.0009 mmol/L, 0.001 mmol/L, 0.002 mmol/L, 0.003 mmol/L, 0.004 mmol/L, 0.005 mmol/L, 0.006 mmol/L, 0.007 mmol/L, 0.008 mmol/L, 0.009 mmol/L, 0.01 mmol/L, 0.02 mmol/L, 0.03 mmol/L, 0.04 mmol/L, 0.05 mmol/L, 0.06 mmol/L, 0.07 mmol/L, 0.08 mmol/L, 0.09 mmol/L, 0.1 mmol/L, 0.2 mmol/L, 0.3 mmol/L, 0.4 mmol/L, 0.5 mmol/L, 0.6 mmol/L, 0.7 mmol/L, 0.8 mmol/L, 0.9 mmol/L, or 1.0 mmol/L or can be an amount falling within a range including any of the foregoing.

Fortified balloon inflation fluids having nanoparticles as the fortification component can include a concentration of nanoparticles from at least 0.01 weight per volume percent (w/v %) to 15 w/v %. In some embodiments, the concentration of nanoparticles present in the fortified balloon inflation fluids can be greater than or equal to 0.01 w/v %, 0.02 w/v %, 0.03 w/v %, 0.04 w/v %, 0.05 w/v %, 0.06 w/v %, 0.07 w/v %, 0.08 w/v %, 0.09 w/v %, 0.10 w/v %, 0.2 w/v %, 0.3 w/v %, 0.4 w/v %, 0.5 w/v %, 0.6 w/v %, 0.7 w/v %, 0.8 w/v %, 0.9 w/v %, 1 w/v %, 2 w/v %, 3 w/v %, 4 w/v %, 5 w/v %, 6 w/v %, 7 w/v %, 8 w/v %, 9 w/v %, 10 w/v %, 11 w/v %, 12 w/v %, 13 w/v %, 14 w/v %, or 15 w/v %, or can be an amount falling within a range including any of the foregoing.

The fortified balloon inflation fluid can be used in catheter systems herein that include a first light guide disposed along the elongate shaft and within the balloon, where the first light guide can be configured to be placed in optical communication with a light source and the fortified balloon inflation fluid. The fortified balloon inflation fluid can be used in catheter systems herein that include a second light guide, a third light guide, a fourth light guide, or more than four light guides. The light guides suitable for use with the fortified balloon inflation fluid can include any of the light guides configured as described elsewhere herein. The light source used with the fortified balloon inflation fluid can be configured to provide sub-millisecond pulses of a light from the light source to at least the first light guide, thereby initiating plasma formation in the fortified balloon inflation fluid, causing rapid bubble formation, and imparting pressure waves upon the vascular lesion.

The fortification component can be included as a coating on one or more surfaces of the catheter systems herein, where it can be solvated by a base inflation fluid prior to use in treatment at a vascular lesions. Referring now to FIG. 22, a longitudinal cross section of a catheter 2200 is shown in accordance with various embodiments herein. The catheter 2200 can be used in a catheter system for imparting pressure to induce fractures in a vascular lesion within or adjacent a blood vessel wall. The catheter 2200 can be configured to advance to the vascular lesion located within or adjacent a blood vessel. The catheter 2200 can include an elongate shaft 102 and a balloon 122 coupled to the elongate shaft 102. The balloon 122 can include a balloon wall. The catheter 2200 can include a fortification component coating 2202 disposed on an inside surface of the balloon wall and in fluid communication with a base inflation fluid. The fortification component coating 2202 can include a fortification component that comprises carbon or iron, as discussed herein.

The balloon 122 of catheter 2200 can be configured to expand from a collapsed configuration suitable for advancing the catheter 2200 through a patient's vasculature to a first expanded configuration suitable for anchoring the catheter 2200 in position relative to a vascular lesion. The balloon 122 of catheter 2200 can be inflated with a base inflation fluid, where the base inflation fluid is configured to solvate the fortification component coating 2202 on the inside surface of the balloon wall to form a fortified balloon inflation fluid. The fortification component of the fortified balloon inflation fluid can be configured to reduce a threshold for inducing plasma formation in the fortified balloon inflation fluid compared to the base inflation fluid.

The catheter 2200 can include a first light guide 2204 disposed along the elongate shaft 102 and within the balloon 122, the first light guide 2204 can be configured to be placed in optical communication with a light source and the fortified balloon inflation fluid. The catheter 2200 can also include a second light guide coupled to the elongate shaft, where the second light guide can be in optical communication with the light source and the fortified balloon inflation fluid. The light source can be configured to provide sub-millisecond pulses of light from the light source to at least the first light guide 2204, and if present any additional light guides, thereby initiating plasma formation in the fortified balloon inflation fluid, causing rapid bubble formation, and imparting pressure waves upon the vascular lesion. The first light guide 2204 can be an optical fiber and the light source can be a laser, both of which are described in more detail elsewhere herein.

The catheters herein can also include a fortification component within a fortification component coating disposed along the elongate shaft. Referring now to FIG. 23, a longitudinal cross section of a catheter 2300 is shown in accordance with various embodiments herein. Catheter 2300 is similar to catheter 2200 of FIG. 22, in that it has similar components including an elongate shaft 102 and a balloon 122 coupled to the elongate shaft 102. The balloon 122 can include a balloon wall. The catheter 2300 can include a fortification component coating 2302 disposed on a surface of the elongate shaft 102 and in fluid communication with the base inflation fluid. The fortification component coating 2302 can include a fortification component that comprises carbon or iron, as discussed herein.

The balloon 122 of catheter 2300 can be configured to expand from a collapsed configuration suitable for advancing the catheter 2300 through a patient's vasculature to a first expanded configuration suitable for anchoring the catheter 2300 in position relative to a vascular lesion. The balloon 122 of catheter 2300 can be inflated with a base inflation fluid, where the base inflation fluid is configured to solvate the fortification component coating 2302 disposed on a surface of the elongate shaft to form a fortified balloon inflation fluid. The fortification component of the fortified balloon inflation fluid can be configured to reduce a threshold for inducing plasma formation in the fortified balloon inflation fluid compared to the base inflation fluid.

The catheter 2300 can include a first light guide 2304 disposed along the elongate shaft 102 and within the balloon 122, the first light guide 2304 can be configured to be placed in optical communication with a light source and the fortified balloon inflation fluid. The catheter 2300 can also include a second light guide coupled to the elongate shaft, where the second light guide can be in optical communication with the light source and the fortified balloon inflation fluid. The light source can be configured to provide sub-millisecond pulses of light from the light source to at least the first light guide 2304, and if present any additional light guides, thereby initiating plasma formation in the fortified balloon inflation fluid, causing rapid bubble formation, and imparting pressure waves upon the vascular lesion. The first light guide 2304 can be an optical fiber and the light source can be a laser, both of which are described in more detail elsewhere herein.

The fortified balloon inflation media described can be used in various methods for generating pressure waves to induce fractures in a vascular lesion within or adjacent a vessel wall of a blood vessel. In one embodiment, the method can include advancing a catheter to a vascular lesion within the blood vessel, where the catheter includes an elongate shaft, a balloon coupled to the elongate shaft, and at least a first light guide disposed along the elongate shaft within the balloon. The method can include expanding the balloon from a collapsed configuration suitable for advancing the catheter through a patient's vasculature to a first expanded configuration suitable for anchoring the catheter in position relative to a vascular lesion. The step of expanding the balloon can include expanding the balloon with a fortified balloon inflation fluid including a base inflation fluid and a fortification component, where the fortification component can be configured to reduce a threshold for inducing plasma formation in the fortified balloon inflation fluid compared to the base inflation fluid. In various embodiments, the method of expanding the balloon can include providing the fortification component as a coating disposed on an inside surface of a balloon wall or on the elongate shaft, where the fortification component coating is in fluid communication with the base inflation fluid, and providing the base inflation fluid to the balloon, where the base inflation fluid solvates the fortification component coating to form the fortified balloon inflation fluid.

The fortification component can include carbon or iron, where the fortification component can include, but is not to be limited to, iron dextran or nanoparticles. Some exemplary nanoparticles include iron nanoparticles, gold nanoparticles, copper nanoparticles, carbon nanoparticles, carbon nanotubes, including, but not to be limited to single walled carbon nanotubes or double walled carbon nanotubes or mixtures thereof, gold-coated carbon nanotubes, or copper-coated carbon nanotubes. In various embodiments, after expanding the balloon, the method can include activating a light source in optical communication with the light guide and the fortified balloon inflation fluid to provide sub-millisecond pulses of light from the light source to the fortified balloon inflation fluid, thereby initiating plasma formation in a fortified balloon inflation fluid and causing rapid bubble formation, and imparting pressure waves upon the vascular lesion. In some embodiments, after activating the light source, the method can include further expanding the balloon from the first expanded configuration to a second further expanded configuration. In other embodiments, after activating the light source, the method can include further expanding the balloon from the first expanded configuration to a second further expanded configuration.

The light sources herein can be configured to generate sub-millisecond pulses of light to be delivered to a treatment site at a frequency of from at least 1 hertz (Hz) to 5000 Hz. In some embodiments, the light sources herein can be configured to generate sub-millisecond pulses of light to be delivered to a treatment site at a frequency from at least 30 Hz to 1000 Hz. In other embodiments, the light sources herein can be configured to generate the sub-millisecond pulses of light to be delivered to a treatment site at a frequency from at least 10 Hz to 100 Hz. In yet other embodiments, the light sources herein can be configured to generate sub-millisecond pulses of light to be delivered to a treatment site at a frequency from at least 1 Hz to 30 Hz. In some embodiments, the light sources herein can be configured to generate sub-millisecond pulses of light to be delivered to a treatment site at a frequency that can be greater than or equal to 1 Hz, 2 Hz, 3 Hz, 4 Hz, 5 Hz, 6 Hz, 7 Hz, 8 Hz, or 9 Hz, 10 Hz, 20 Hz, 30 Hz, 40 Hz, 50 Hz, 60 Hz, 70 Hz, 80 Hz, 90 Hz, 100 Hz, 200 Hz, 300 Hz, 400 Hz, 500 Hz, 600 Hz, 700 Hz, 800 Hz, 900 Hz, 1000 Hz, 1250 Hz, 1500 Hz, 1750 Hz, 2000 Hz, 2250 Hz, 2500 Hz, 2750 Hz, 3000 Hz, 3250 Hz, 3500 Hz, 3750 Hz, 4000 Hz, 4250 Hz, 4500 Hz, 4750 Hz, or 5000 Hz or can be an amount falling within a range between any of the foregoing.

Balloons

The balloons suitable for use in the catheter systems herein include those that can be passed through the vasculature of a patient when in a collapsed configuration. In some embodiments, the balloons herein are made from silicone. In other embodiments, the balloons herein are made from polydimethylsiloxane (PDMS), polyurethane, polymers such as PEBAX™ material available from Arkema, which has a location at King of Prussia, Pennsylvania, USA, nylon, and the like. In some embodiments, the balloons can include those having diameters ranging from 1 millimeter (mm) to 25 mm in diameter. In some embodiments, the balloons can include those having diameters ranging from at least 1.5 mm to 12 mm in diameter. In some embodiments, the balloons can include those having diameters ranging from at least 1 mm to 5 mm in diameter. In some embodiments, the diameter can be greater than or equal to 0.5 mm, 1.0 mm, 1.5 mm, 2.0 mm, 2.5 mm, 3.0 mm, 3.5 mm, 4.0 mm, 4.5 mm, 5.0 mm, 5.5 mm, 6.0 mm, 6.5 mm, 7.0 mm, 7.5 mm, 8.0 mm, 8.5 mm, 9.0 mm, 9.5 mm, 10.0 mm, 10.5 mm, 11.0 mm, 11.5 mm, 12.0 mm, 12.5 mm, 13.0 mm, 13.5 mm, 14.0 mm, 14.5 mm, 15.0 mm, 15.5 mm, 16.0 mm, 16.5 mm, 17.0 mm, 17.5 mm, 18.0 mm, 18.5 mm, 19.0 mm, 19.5 mm, or 20.0 mm, or can be an amount falling within a range between any of the foregoing.

In some embodiments, the balloons herein can include those having a length ranging from at least 5 mm to 300 mm in length. In some embodiments, the balloons herein can include those having a length ranging from at least 8 mm to 200 mm in length. In some embodiments, the length of the balloon can be greater than or equal to 5 mm, 10 mm, 20 mm, 30 mm, 40 mm, 50 mm, 60 mm, 70 mm, 80 mm, 90 mm, 100 mm, 110 mm, 120 mm, 130 mm, 140 mm, 150 mm, 160 mm, 170 mm, 180 mm, 190 mm, 200 mm, 210 mm, 220 mm, 230 mm, 240 mm, 250 mm, 260 mm, 270 mm, 280 mm, 290 mm, or 300 mm, or can be an amount falling within a range between any of the foregoing.

The balloons herein can be inflated to inflation pressures from 1 atmosphere (atm) to 70 atm. In some embodiments, the balloons herein can be inflated to inflation pressures of from at least 20 atm to 70 atm. In some embodiments, the balloons herein can be inflated to inflation pressures of from at least 6 atm to 20 atm. In some embodiments, the balloons herein can be inflated to inflation pressures of from at least 3 atm to 20 atm. In some embodiments, the balloons herein can be inflated to inflation pressures of from at least 2 atm to 10 atm. In some embodiments, the balloons herein can be inflated to inflation pressures that can be greater than or equal to 1 atm, 2 atm, 3 atm, 4 atm, 5 atm, 6 atm, 7 atm, 8 atm, 9 atm, 10 atm, 15 atm, 20 atm, 25 atm, 30 atm, 35 atm, 40 atm, 45 atm, 50 atm, 55 atm, 60 atm, 65 atm, or 70 atm, or can be an amount falling within a range between any of the foregoing.

The balloons herein can include those having various shapes, including, but not to be limited to, a conical shape, a cylindrical shape, a square shape, a rectangular shape, a spherical shape, a conical/square shape, a conical/spherical shape, an extended spherical shape, an oval shape, a tapered shape, a bone shape, a stepped diameter shape, an offset shape, or a conical offset shape. In some embodiments, the balloons herein can include a drug eluting coating or a drug eluting stent structure. The drug elution coating or drug eluting stent can include one or more therapeutic agents including anti-inflammatory agents, anti-neoplastic agents, anti-angiogenic agents, and the like.

Balloon Fluids

Exemplary balloon fluids suitable for use herein can include, but are not to be limited to one or more of water, saline, contrast medium, fluorocarbons, perfluorocarbons, gases, such as carbon dioxide, and the like. In some embodiments, the balloon fluids described can be used as base inflation fluids, discussed elsewhere herein. In some embodiments, the balloon inflation fluids include a mixture of saline to contrast medium in a volume ratio of 50:50. In some embodiments, the balloon fluids include a mixture of saline to contrast medium in a volume ratio of 25:75. In some embodiments, the balloon fluids include a mixture of saline to contrast medium in a volume ratio of 75:25. The balloon fluids suitable for use herein can be tailored on the basis of composition, viscosity, and the like in order to manipulate the rate of travel of the pressure waves therein. The balloon fluids suitable for use herein are biocompatible. A volume of balloon fluid can be tailored by the chosen light source and the type of balloon fluid used.

In some embodiments, the contrast agents used in the contrast media herein can include, but are not to be limited to, iodine-based contrast agents, such as ionic or non-ionic iodine-based contrast agents. Some non-limiting examples of ionic iodine-based contrast agents include diatrizoate, metrizoate, iothalamate, and ioxaglate. Some non-limiting examples of non-ionic iodine-based contrast agents include iopamidol, iohexol, ioxilan, iopromide, iodixanol, and ioversol. In other embodiments, non-iodine based contrast agents can be used. Suitable non-iodine containing contrast agents can include gadolinium (III)-based contrast agents. Suitable fluorocarbon and perfluorocarbon agents can include, but are not to be limited to, agents such as the perfluorocarbon dodecafluoropentane (DDFP, C5F12).

The balloon fluids herein can include those that include absorptive agents that can selectively absorb light in the ultraviolet (e.g., at least 10 nanometers (nm) to 400 nm), visible region (e.g., at least 400 nm to 780 nm), and near-infrared region of the electromagnetic spectrum (e.g., at least 780 nm to 2.5 µm), or in the far-infrared region of the electromagnetic spectrum of at least 2.5 micrometers to 10 micrometers (µm). Suitable absorptive agents can include those with absorption maxima along the spectrum from at least 10 nm to 2.5 µm. In various embodiments, the absorptive agent can be those that have an absorption maximum matched with the emission maximum of the laser used in the catheter system. By way of non-limiting examples, various lasers described herein can include neodymium:yttrium-aluminum-garnet (Nd:YAG–emission maximum=1064 nm) lasers, holmium:YAG (Ho:YAG–emission maximum=2.1 µm) lasers, or erbium:YAG (Er:YAG–emission maximum=2.94 µm). In some embodiments, the absorptive agents used herein can be water soluble. In other embodiments, the absorptive agents used herein are not water soluble. In some embodiments, the absorptive agents used in the balloon fluids herein can be tailored to match the peak emission of the light source. Various light sources having emission wavelengths of at least 10 nanometers to greater than 1 millimeter are discussed elsewhere herein.

In some embodiments, introduction of the balloon fluid causes the expansion of the balloon from a collapsed configuration to a first expanded configuration and from a first expanded configuration to a second further expanded configuration. In addition or alternatively, the expansion of the balloon can be accomplished using a shape-memory material or other means.

Light Guides (FIGS. 24-29)

The light guides herein can include an optical fiber or flexible light pipe. The light guides herein can be thin and flexible and can allow light signals to be sent with very little loss of strength. The light guides herein can include a core surrounded by a cladding about its circumference. In some embodiments, the core can be a cylindrical core or a partially cylindrical core. The core and cladding of the light guides can be formed from one or more materials, including but not limited to one or more types of glass, silica, or one or more polymers. The light guides may also include a protective coating, such as a polymer. It is appreciated that the index of refraction of the core will be greater than the index of refraction of the cladding.

Each light guide can guide light along its length to a distal portion having at least one optical window. The light guides can create a light path as portion of an optical network including a light source. The light path within the optical network allows light to travel from one part of the network to another. Both the optical fiber and/or the flexible light pipe can provide a light path within the optical networks herein.

The light guides herein can assume many configurations about the elongate shaft of the catheters described herein. In some embodiments, the light guides can run parallel to the longitudinal axis of the elongate shaft of the catheter. In some embodiments, the light guides can be disposed spirally or helically about the longitudinal axis of the elongate shaft of the catheter. In some embodiments, the light guides can be physically coupled to the elongate shaft. In other embodiments, the light guides can be disposed along the length of the outer diameter of the elongate shaft. In yet other embodiments the light guides herein can be disposed within one or more light guide lumens within the elongate shaft. Various configurations for the elongate shafts and light guide lumens will be discussed below.

Figure 24:
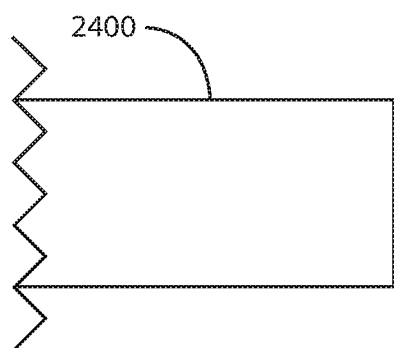
FIGS. 24-29 are schematic cross-sectional views of various embodiments of a distal portion of a light guide of a catheter in accordance with various embodiments herein.
Figure 25:
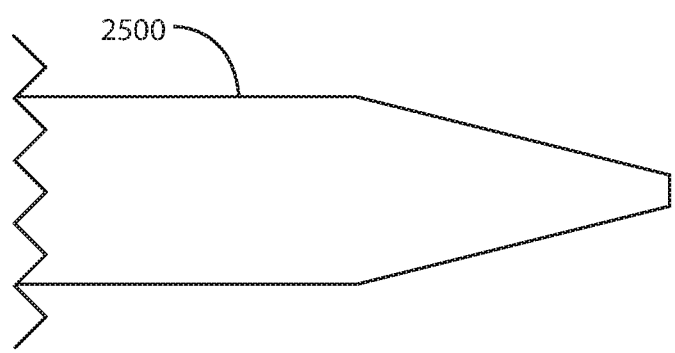
Figure 26:
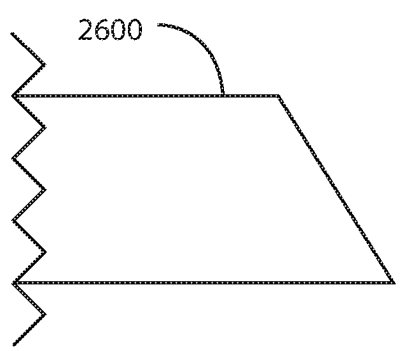
Figure 27:
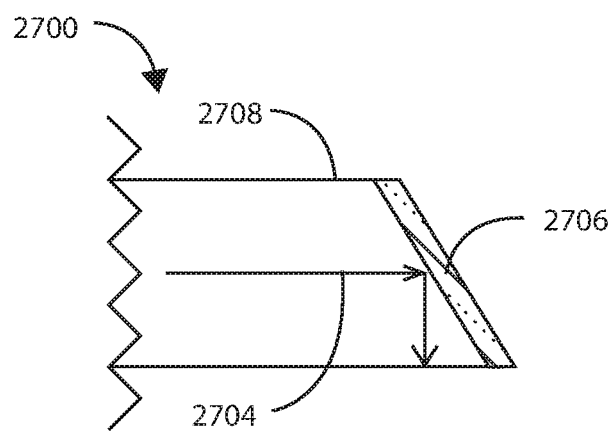
Figure 28:
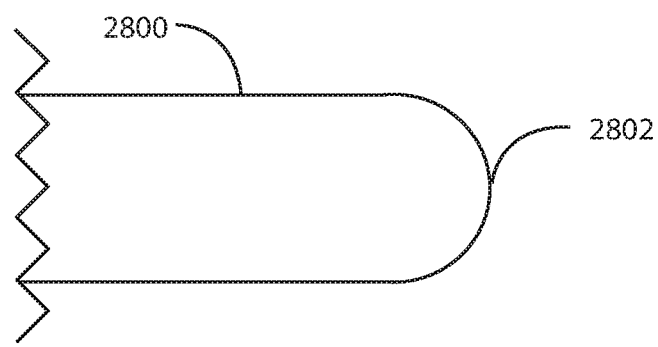
Figure 29:
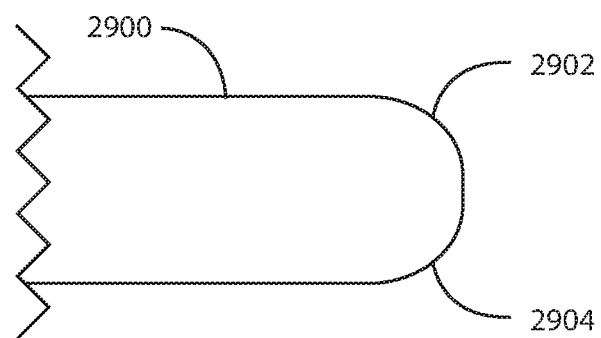
Figure 36:
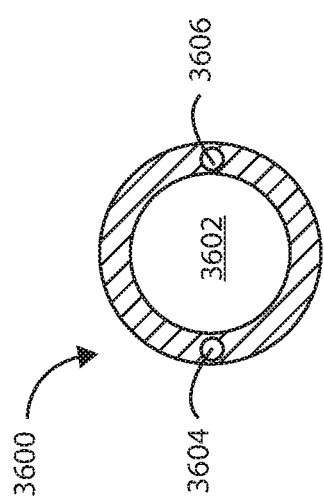
Figure 37:
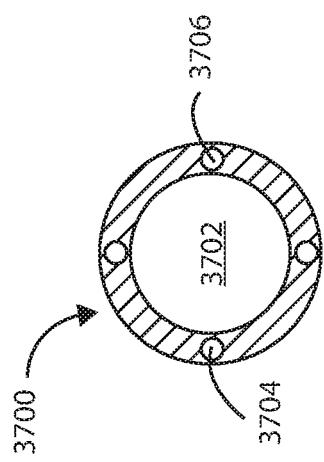
Figure 38:
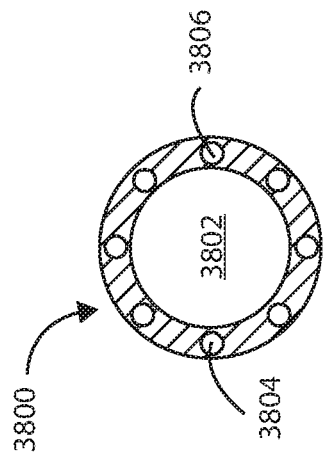
Figure 39:
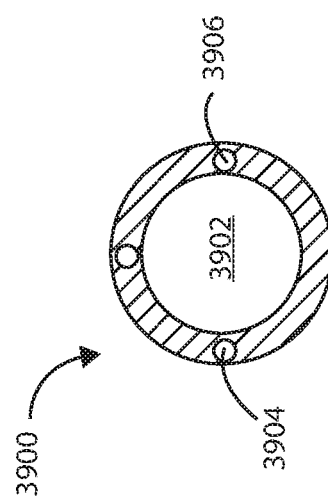
Figure 40:
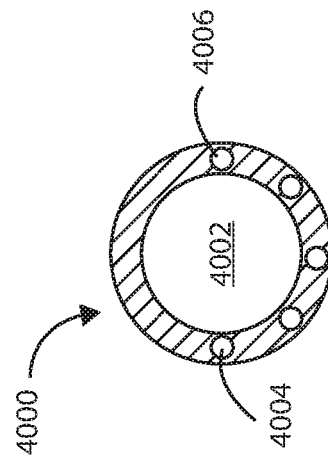
Figure 41:
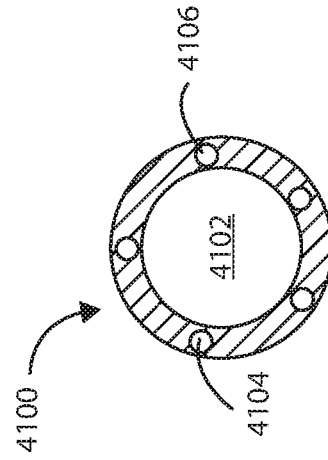

The light guides herein can include various configurations at a distal portion of the light guide. Referring now to FIGS. 24-29, schematic cross-sectional views of the distal portions of various shaped light guides are shown in accordance with various embodiments herein. In FIG. 24, a schematic cross-sectional view of a light guide 2400 is shown. Light guide 2400 includes a cylindrical end shape. In some embodiments, the end of the light guide can have a tapered shape. By way of example, in FIG. 25 a schematic cross-sectional view of a light guide 2500 having a tapered end shape is shown. In some embodiments, the end of the light guide can have an angled shape. By way of example, in FIG. 26 a schematic cross-sectional view of a light guide 2600 is shown. Light guide 2600 includes an angled end shape. In some embodiments, a light guide with an angled shape can include a diverting feature. By way of example, in FIG. 27 a schematic cross-sectional view of a light guide 2700 is shown. The light guide 2700 also includes a diverting feature 2706 at the distal portion to direct the light 2704 within the light guide toward the side surface portion 2708 of the light guide. Light guide 2700 is configured such that light 2704 travels from a light source (not shown) in the direction from the proximal portion of the light guide to the distal portion of the light guide 2700, as indicated by the arrow. Upon contact with the diverting feature 2706, the light 2704 is diverted, or reflected, within the light guide 2700.

In some embodiments, a diverting feature can be included with the light guide to direct light toward a side surface portion of the distal portion of the light guide. A diverting feature can include any feature of the system herein that diverts light from the light guide away from its axial path toward a side surface portion of the light guide. Examples include a reflector, a refracting element, and a fiber diffuser. Fiber diffusers will be discussed in more detail below.

The light guides herein can also include one or more focusing elements for directing the origin of a pressure wave away from the distal tip of the light guides. By way of example, in FIG. 28 a schematic cross-sectional view of a light guide 2800 is shown. The light guide 2800 includes a first convex surface 2802. The first convex surface 2802 is configured to direct light away from the distal tip of the light guide 2800 to generate a pressure wave having an origin point away from the surface of the distal tip. In some embodiments, the light guides in accordance with the embodiments therein can be configured to include multiple convex surfaces. By way of example, in FIG. 29 a schematic cross-sectional view of a light guide 2900 is shown. The light guide 2900 includes a first convex surface 2902 and a second convex surface 2904. The first convex surface 2902 and second convex surface 2904 can be configured to direct light away from the distal tip of the light guide to generate a plurality of pressure waves each having a plurality of origin points away from the surface of the distal tip.

In other embodiments, the light guides can form a spiral configuration about the longitudinal axis of the elongate shaft of the catheter. In some embodiments, the spiral configuration can run clockwise about the longitudinal axis of the elongate shaft of the catheter, while in other embodiments the spiral configuration can run counter-clockwise about the longitudinal axis of the elongate shaft of the catheter. In some embodiments, the light guides can form a single helix, a double helix, a triple helix, or a quadruple helix about the longitudinal axis of the elongate shaft of the catheter.

The light guides herein can come in various sizes and configurations. The light guides will have a longitudinal axis along the elongate shaft of the light guide and short axis about its circumference. In some embodiments, the light guides can have an outer diameter of about 100 μm, including the cladding and the core. In other embodiments, the light guides can include those that have an outer diameter of from 50 μm to 1000 μm including the cladding and the core. The length of the light guides can include those having a length of from 40 cm to 175 cm. In some embodiments, the length of the light guides can include those having a length of from 50-150 cm. In some embodiments, the length of the light guide can include those having a length of 40 cm, 50 cm, 60 cm, 70 cm, 80 cm, 90 cm, 100 cm, 125 cm, 150 cm, or 175 cm. It is appreciated that the light guides herein can have a usable length that can fall within a range, wherein any of the forgoing lengths can serve as the lower or upper bound of the range, provided that the lower bound of the range is a value less than the upper bound of the range.

It is appreciated that one or more light guides herein can be adhered to the outside surface of the elongate shaft of a catheter, to create a catheter. However, in other embodiments, one or more light guides can be disposed within a lumen of a catheter. In addition, the catheter may define a lumen for a guidewire having an inner diameter of about 0.014 inch (0.356 mm). In some embodiments, the catheter can include those having an inner diameter of about 0.018 inch (0.457 mm). In yet other embodiments, the catheter can include those having an inner diameter of about 0.035 inch (0.889 mm). In some embodiments the light guides herein can be integrated with a balloon catheter. In some embodiments the light guides herein can be integrated into a guidewire. In embodiments where the light guide is integrated into a guidewire, the resulting catheter can be used independently or can be used with various other balloon catheters.

Lumens of the Elongate Shaft (FIGS. 30-41)

The elongate shafts herein can include one or more lumens that span the length of the elongate shaft. Referring now to FIGS. 30-41, schematic cross-sectional views of various embodiments of an elongate shaft having multiple lumens are shown in accordance with various embodiments herein. In some embodiments, the elongate shaft can define a guidewire lumen. In some embodiments, the elongate shaft defines an inflation lumen surrounding the guidewire lumen, where the inflation lumen is in fluid communication with a balloon at a distal portion of the elongate shaft. In other embodiments, the elongate shaft defines an inflation lumen disposed alongside the guidewire lumen, where the inflation lumen is in fluid communication with a balloon at a distal portion of the elongate shaft. In yet other embodiments, the elongate shaft defines at least one control lumen, at least one light guide lumen, or at least one drug therapy lumen.

In the configuration in FIG. 30, elongate shaft 3000 includes concentrically disposed guidewire lumen 3002 and an inflation lumen 3004. In the configuration in FIG. 31, elongate shaft 3100 includes guidewire lumen 3102 and an inflation lumen 3104 disposed adjacent to and partially surrounding guidewire lumen 3102. In the configuration in FIG. 32, elongate shaft 3200 includes guidewire lumen 3202 and an inflation lumen 3204 disposed adjacent to guidewire lumen 3202. In the configuration in FIG. 33, elongate shaft 3300 includes guidewire lumen 3302 inflation lumen 3304, and a control lumen 3306. It is appreciated that the control lumens herein can be used for many purposes, including, but not to be limited to, blood flow, cooling or heating fluid flow, delivery of a diagnostic or therapeutic agent, light guides, and the like. In the configuration in FIG. 34, elongate shaft 3400 includes guidewire lumen 3402, inflation lumen 3404, and two control lumens 3406 and 3408. In the configuration in FIG. 35, elongate shaft 3500 includes guidewire lumen 3502, inflation lumen 3504, and control lumen 3506.

The light guides can be disposed within one or more light guide lumens disposed within the elongate shafts symmetrically about the circumference. In some embodiments, the lumens herein can include those that are used for blood flow, cooling or heating fluid flow, delivery of a diagnostic or therapeutic agent, and the like. In the configuration in FIG. 36, elongate shaft 3600 includes guidewire lumen 3602, light guide lumen 3604, and control lumen 3606. One or more of lumens 3602, 3604 and 3606 can serve as an inflation lumen. In the configuration in FIG. 37, elongate shaft 3700 includes guidewire lumen 3702, light guide lumen 3704, and control lumen 3706. Elongate shaft 3700 includes two additional lumens that can both be configured as light guide lumens, control lumens, or both a light guide lumen and control lumen. One or more of lumens 3702, 3704 and 3706 can serve as an inflation lumen. In the configuration in FIG. 38, elongate shaft 3800 includes guidewire lumen 3802, light guide lumen 3804, and control lumen 3806. Elongate shaft 3800 includes six additional lumens that can be configured as inflation lumens, light guide lumens, control lumens, or any combination of inflation lumens, light guide lumens and control lumens.

The light guides can be disposed within one or more light guide lumens disposed within the elongate shafts asymmetrically about the circumference. In the configuration in FIG. 39, elongate shaft 3900 includes guidewire lumen 3902, light guide lumen 3904, and control lumen 3906. Elongate shaft 3900 includes one additional lumen that can be configured as a light guide lumen 3904 or a control lumen 3906. In the configuration in FIG. 40, elongate shaft 4000 includes guidewire lumen 4002, light guide lumen 4004, and control lumen 4006. Elongate shaft 4000 includes three additional lumens that can be configured as light guide lumens, control lumens, or any combination of light guide lumens and control lumens. In the configuration in FIG. 41, elongate shaft 4100 includes guidewire lumen 4102, light guide lumen 4104, and control lumen 4106. Elongate shaft 4100 includes three additional lumens that can be configured as inflation lumens, light guide lumens, control lumens, or any combination of inflation lumens, light guide lumens, and control lumens.

It is appreciated that the lumens described in FIGS. 30-41 can assume many shapes, including, but not to be limited to, circular shape, square shape, crescent shape, triangular shape, and the like. The lumens of the elongate shafts can by symmetrically disturbed in the elongate shaft, asymmetrically distributed, or concentrically distributed. It will be further appreciated that the light guide lumens herein can be coated along the longitudinal length of the elongate shaft with a reflective material capable of propagating light along the elongate shaft from a distal light source to the proximal portion of the catheter, so that the lumen itself can act as a light guide without a separate fiber optic structure.

Diverting Features

The diverting features suitable for use herein include a reflecting element, a refracting element, and a fiber diffuser. In some embodiments, the diverting feature can be a reflecting element. In some embodiments, the diverting feature can be a refracting element. In some embodiments, the diverting feature can be a fiber diffuser.

A fiber diffuser can direct light from within a light guide to exit at a side surface portion of the light guide. The fiber diffusers described herein can be created several ways. In some embodiments, the fiber diffusers can be created by micro-machining the surface of the distal portion of a light guide with a $CO_2$ laser. In some embodiments, a fused silica coating can be applied to the distal portion of the light guide. In other embodiments, the fiber diffuser can be formed from a glass, a polymer, or a metal coating on the distal portion of the light guide. In other embodiments, the fiber diffuser can be formed by a fiber Bragg grating on the distal portion of the light guide. In some embodiments, the fiber diffuser can include a machined portion of the light guide, a laser-machined portion of the light guide, fiber Bragg gratings, a fused splicing, a fused splicing forming at least one internal mirror, and a splicing of two or more diffuse regions.

Suitable materials for a fiber diffuser can include, but are not be limited to, the materials of the light guide core or light guide cladding, ground glass, silver coated glass, gold coated glass, TiO2, and other materials that will scatter and not significantly absorbed the light wavelength of interest. One method that can be used to create a uniform diffuser in a light guide, optical component, or materials is to utilize scattering centers on the order of at least 50 nanometers to 5 micrometers in size. The scattering centers can have a distribution about 200 nanometers in size.

The diverting features suitable for focusing light away from the tip of the light guides herein can include, but are not to be limited to, those having a convex surface, a gradient-index (GRIN) lens, and a mirror focus lens.

Light Sources

The light sources suitable for use herein can include various types of light sources including lasers and lamps. Suitable lasers can include short pulse lasers on the sub-millisecond timescale. In some embodiments, the light source can include lasers on the nanosecond (ns) timescale. The lasers can also include short pulse lasers on the picosecond (ps), femtosecond (fs), and microsecond (us) timescales. It is appreciated that there are many combinations of laser wavelengths, pulse widths and energy levels that can be employed to achieve plasma in the balloon fluid of the catheters described herein. In various embodiments, the pulse widths can include those falling within a range including from at least 10 ns to 200 ns. In some embodiments, the pulse widths can include those falling within a range including from at least 20 ns to 100 ns. In another embodiment, the pulse widths can include those falling within a range including from at least 50 ns to 1500 ns. In other embodiments, the pulse widths can include those falling within a range including from at least 1 ns to 5000 ns. Still alternatively, the pulse widths can fall outside of the foregoing ranges.

Exemplary nanosecond lasers can include those within the UV to IR spectrum, spanning wavelengths of about 10 nanometers to 1 millimeter. In some embodiments, the light sources suitable for use in the catheter systems herein can include those capable of producing light at wavelengths of from at least 750 nm to 2000 nm. In some embodiments, the light sources can include those capable of producing light at wavelengths of from at least 700 nm to 3000 nm. In some embodiments, the light sources can include those capable of producing light at wavelengths of from at least 100 nm to 10 micrometers (μm). Nanosecond lasers can include those having repetition rates of up to 200 kHz. In some embodiments, the laser can include a Q-switched thulium:yttrium-aluminum-garnet (Tm:YAG) laser. In some embodiments, the laser can include a neodymium:yttrium-aluminum-garnet (Nd:YAG), holmium:yttrium-aluminum-garnet (Ho:YAG), erbium:yttrium-aluminum-garnet (Er:YAG), excimer laser, helium-neon laser, carbon dioxide laser, as well as doped, pulsed, fiber lasers.

Pressure Waves

The catheters herein can generate pressure waves having maximum pressures in the range of at least 1 megapascal (MPa) to 100 MPa. The maximum pressure generated by a particular catheter will depend on the light source, the absorbing material, the bubble expansion, the propagation medium, the balloon material, and other factors. In some embodiments, the catheters herein can generate pressure waves having maximum pressures in the range of at least 2 MPa to 50 MPa. In other embodiments, the catheters herein can generate pressure waves having maximum pressures in the range of at least 2 MPa to 30 MPa. In yet other embodiments, the catheters herein can generate pressure waves having maximum pressures in the range of at least 15 MPa to 25 MPa. In some embodiments, the catheters herein can generate pressure waves having peak pressures of greater than or equal to 1 MPa, 2 MPa, 3 MPa, 4 MPa, 5 MPa, 6 MPa, 7 MPa, 8 MPa, 9 MPa, 10 MPa, 11 MPa, 12 MPa, 13 MPa, 14 MPa, 15 MPa, 16 MPa, 17 MPa, 18 MPa, 19 MPa, 20 MPa, 21 MPa, 22 MPa, 23 MPa, 24 MPa, or 25 MPa, 26 MPa, 27 MPa, 28 MPa, 29 MPa, 30 MPa, 31 MPa, 32 MPa, 33 MPa, 34 MPa, 35 MPa, 36 MPa, 37 MPa, 38 MPa, 39 MPa, 40 MPa, 41 MPa, 42 MPa, 43 MPa, 44 MPa, 45 MPa, 46 MPa, 47 MPa, 48 MPa, 49 MPa, or 50 MPa. It is appreciated that catheters herein can generate pressure waves having operating pressures or maximum pressures that can fall within a range, wherein any of the forgoing numbers can serve as the lower or upper bound of the range, provided that the lower bound of the range is a value less than the upper bound of the range.

Therapeutic treatment can act via a fatigue mechanism or a brute force mechanism. For a fatigue mechanism, operating pressures would be about at least 0.5 MPa to 2 MPa, or about 1 MPa. For a brute force mechanism, operating pressures would be about at least 20 MPa to 30 MPa, or about 25 MPa. Pressures between the extreme ends of these two ranges may act upon a calcified lesion using a combination of a fatigue mechanism and a brute force mechanism.

The pressure waves described herein can be imparted upon the treatment site from a distance within a range from at least 0.1 millimeters (mm) to 25 mm extending radially from a longitudinal axis of a catheter placed at a treatment site. In some embodiments, the pressure waves can be imparted upon the treatment site from a distance within a range from at least 10 mm to 20 mm extending radially from a longitudinal axis of a catheter placed at a treatment site. In other embodiments, the pressure waves can be imparted upon the treatment site from a distance within a range from at least 1 mm to 10 mm extending radially from a longitudinal axis of a catheter placed at a treatment site. In yet other embodiments, the pressure waves can be imparted upon the treatment site from a distance within a range from at least 1.5 mm to 4 mm extending radially from a longitudinal axis of a catheter placed at a treatment site. In some embodiments, the pressure waves can be imparted upon the treatment site from a range of at least 2 MPa to 30 MPa at a distance from 0.1 mm to 10 mm. In some embodiments, the pressure waves can be imparted upon the treatment site from a range of at least 2 MPa to 25 MPa at a distance from 0.1 mm to 10 mm. In some embodiments, the pressure waves can be imparted upon the treatment site from a distance that can be greater than or equal to 0.1 mm, 0.2 mm, 0.3 mm, 0.4 mm, 0.5 mm, 0.6 mm, 0.7 mm, 0.8 mm, or 0.9 mm, 1 mm, 2 mm, 3 mm, 4 mm, 5 mm, 6 mm, 7 mm, 8 mm, 9 mm, or 10 mm, or can be an amount falling within a range between any of the foregoing.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, a description of a technology in the "Background" is not an admission that technology is prior art to any invention(s) in this disclosure. Neither is the "Summary" or "Abstract" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

It is understood that although a number of different embodiments of the catheter systems have been illustrated and described herein, one or more features of any one embodiment can be combined with one or more features of one or more of the other embodiments, provided that such combination satisfies the intent of the present invention.

While a number of exemplary aspects and embodiments of the catheter systems have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope, and no limitations are intended to the details of construction or design herein shown.

What is claimed is:

1. A catheter system for imparting pressure to induce fractures in a treatment site within or adjacent a vessel wall, comprising:
    a catheter configured to advance to the treatment site, the catheter comprising an elongate shaft and a balloon coupled to the elongate shaft, the balloon having a balloon wall;
    a first light guide disposed along the elongate shaft and positioned at least partially within the balloon, the first light guide being in optical communication with a light source and a balloon fluid, the first light guide including a distal portion that is positioned within the balloon fluid; and
    a first focusing element located at the distal portion of the first light guide, the first focusing element being in optical communication with the light source, the first focusing element being configured to direct light from within the first light guide to a first location at a first distance away from the distal portion of the first light guide so that plasma formation in the balloon fluid is initiated away from the distal portion of the first light guide and so that rapid bubble formation occurs, thereby imparting pressure waves upon the treatment site.

2. The catheter system of claim 1, further comprising a second focusing element located at the distal portion of the first light guide, the second focusing element being configured to direct light from within the first light guide to a second location at a second distance away from the distal portion of the first light guide so that plasma formation in the balloon fluid is initiated away from the distal portion of the first light guide and so that rapid bubble formation occurs, thereby imparting pressure waves upon the treatment site.

3. The catheter system of claim 1, wherein the first focusing element comprises a convex lens, a convex mirror, or a gradient-index (GRIN) lens.

4. The catheter system of claim 1, wherein the distal portion of the first light guide includes a distal tip of the first light guide, and wherein the first focusing element is located at the distal tip of the first light guide.

5. The catheter system of claim 4, wherein the first location is spaced away from the distal tip of the first light guide and is centered on a longitudinal axis of the first light guide.

6. The catheter system of claim 4, wherein the first distance is at least 1 µm and at most 5 mm away from the distal tip of the first light guide.

7. The catheter system of claim 1, further comprising:
a second light guide coupled to the elongate shaft, wherein the second light guide is in optical communication with the light source and the balloon fluid, the second light guide including a distal portion that is positioned within the balloon fluid; and
a second focusing element located at the distal portion of the second light guide and in optical communication with the light source, the second focusing element being configured to direct light from within the second light guide to a second location at a second distance from the distal portion of the second light guide so that plasma formation in the balloon fluid is initiated away from the distal portion of the second light guide and so that rapid bubble formation occurs, thereby imparting pressure waves upon the treatment site.

8. The catheter system of claim 1, wherein the first light guide is an optical fiber and wherein the light source is a laser.

9. The catheter system of claim 1, wherein the first light guide includes a longitudinal axis, and a first diverting feature positioned at the distal portion of the first light guide, the first diverting feature being configured to direct light from within the first light guide toward the first focusing element and toward the balloon wall, the first location being spaced away from the longitudinal axis of the first light guide.

10. The catheter system of claim 9, wherein the first diverting feature is a fiber diffuser.

11. A method for generating pressure waves to induce fractures at a treatment site within or adjacent a vessel wall, the method comprising the steps of:
advancing a catheter and a first light guide to the treatment site, the catheter comprising an elongate shaft and a balloon coupled to the elongate shaft, the first light guide being disposed along the elongate shaft at least partially within the balloon, the first light guide being in optical communication with a light source and a balloon fluid, the first light guide including a first focusing element located at a distal portion of the first light guide, the distal portion of the first light guide being positioned within the balloon fluid; and
activating the light source to direct light from within the first light guide to a first location at a first distance away from the distal portion of the first light guide so that plasma formation in the balloon fluid is initiated away from the distal portion of the first light guide and so that rapid bubble formation occurs, thereby imparting pressure waves upon the treatment site;
wherein the first location is spaced away from the distal tip and is centered on a longitudinal axis of the first light guide.

12. The method of claim 11, further comprising, after activating the light source, expanding the balloon from a first expanded configuration to a second further expanded configuration.

13. A catheter system for imparting pressure to induce fractures in a treatment site within or adjacent a vessel wall, comprising:
a catheter that is configured to advance to the treatment site, the catheter comprising an elongate shaft and a balloon that is coupled to the elongate shaft, the balloon comprising a balloon wall;
a first light guide that is disposed along the elongate shaft and at least partially within the balloon, the first light guide being in optical communication with a light source and a balloon fluid, the first light guide comprising a first diverting feature positioned at a distal portion of the first light guide, the distal portion of the first light guide being positioned within the balloon fluid; and
a first focusing element positioned at the distal portion of the first light guide so that the first diverting feature is in optical communication with the first focusing element;
wherein the first diverting feature is configured to direct light from within the first light guide toward the first focusing element, and the first focusing element is configured to direct light from within the first light guide to a first location at a first distance from the distal portion of the first light guide and toward the balloon wall so that plasma formation in the balloon fluid is initiated away from the distal portion of the first light guide and so that rapid bubble formation occurs, thereby imparting pressure waves upon the treatment site, the first location being spaced away from a longitudinal axis of the first light guide.

14. The catheter system of claim 13 wherein the first diverting feature is configured to direct light from within the first light guide to a location in the balloon fluid spaced away from the longitudinal axis.

15. The catheter system of claim 13 wherein the first light guide further comprises a second diverting feature positioned at the distal portion of the first light guide, the second diverting feature being configured to direct light from within the first light guide toward a second focusing element.

16. The catheter system of claim 13 further comprising a second light guide that is coupled to the elongate shaft, the second light guide being in optical communication with the light source and the balloon fluid, the second light guide including a distal portion that is positioned within the balloon fluid.

17. The catheter system of claim 13 wherein the first diverting feature is a fiber diffuser.

18. The catheter system of claim 13 wherein the first focusing element is selected from the group consisting of a convex lens, a convex mirror, and a gradient-index (GRIN) lens.

19. The catheter system of claim 13 wherein the first focusing element comprises a GRIN lens.

20. The catheter system of claim 19 wherein the GRIN lens is adhered to a side surface portion of the first light guide.

* * * * *